(12) United States Patent
Geva et al.

(10) Patent No.: US 7,225,013 B2
(45) Date of Patent: May 29, 2007

(54) ADAPTIVE PREDICTION OF CHANGES OF PHYSIOLOGICAL/PATHOLOGICAL STATES USING PROCESSING OF BIOMEDICAL SIGNALS

(75) Inventors: Amir Geva, Meitar (IL); Kobi Todros, Beer Sheva (IL); Baruch Levi, Nes Ziona (IL); David Solomon, Sde-Boker (IL); Dan Kerem, Haifa (IL)

(73) Assignee: Widemed Ltd., Omer (IL)

( * ) Notice: Subject to any disclaimer, the term of this patent is extended or adjusted under 35 U.S.C. 154(b) by 791 days.

(21) Appl. No.: 10/678,773

(22) Filed: Oct. 3, 2003

(65) Prior Publication Data

US 2004/0230105 A1  Nov. 18, 2004

(30) Foreign Application Priority Data

May 15, 2003  (IL) .................................... 155955

(51) Int. Cl.
 *A61B 5/04* (2006.01)
(52) U.S. Cl. ..................... 600/513; 600/481; 600/508
(58) Field of Classification Search ................ 600/300, 600/301, 481, 508, 509, 513, 544, 547
See application file for complete search history.

(56) References Cited

U.S. PATENT DOCUMENTS

| | | | |
|---|---|---|---|
| 3,863,625 | A | 2/1975 | Viglione et al. |
| 5,720,294 | A | 2/1998 | Skinner |
| 5,819,007 | A | 10/1998 | Elghazzawi |
| 5,857,978 | A | 1/1999 | Hively et al. |
| 6,070,098 | A | 5/2000 | Moore-Ede et al. |
| 6,304,775 | B1 | 10/2001 | Iasemidis et al. |
| 6,308,094 | B1 | 10/2001 | Shusterman et al. |
| 6,595,929 | B2 | 7/2003 | Stivoric et al. |
| 2004/0073098 | A1 | 4/2004 | Geva |

FOREIGN PATENT DOCUMENTS

| | | |
|---|---|---|
| WO | WO 00/10455 | 3/2000 |
| WO | WO 2003/057025 | 7/2003 |

OTHER PUBLICATIONS

Lempel et al., "A Universal Algorithm for Sequential Data Compression," IEEE Transactions on Information Theory, IT-23:3 (1977), pp. 337-349.

(Continued)

*Primary Examiner*—Charles A. Marmor, II
*Assistant Examiner*—Zoe E. Baxter
(74) *Attorney, Agent, or Firm*—Marsteller & Associates, P.C.

(57) ABSTRACT

A method and system predicts changes of physiological/pathological states in a patient, based on sampling, processing and analyzing a plurality of aggregated noisy biomedical signals. A reference database of raw data streams or features is generated by aggregating one or more raw data streams. The features are derived from the raw data streams and represent physiological/pathological states. Each feature consists of biomedical signals of a plurality of patients, wherein several patients have one or more of the physiological/pathological states. A path, which is an individual dynamics, between physiological/pathological states is obtained according to their order of appearance. Then, a prediction of being in physiological/pathological states, or transitions to physiological/pathological states in the patient, is obtained by comparing the individual dynamics with known dynamics, obtained from prior knowledge.

46 Claims, 43 Drawing Sheets

OTHER PUBLICATIONS

Akselrod et al., Power Spectrum Analysis of Heart Rate Fluctuation: A Quantitative Probe of Beat-to-Beat Cardiovascular Control,: Science 213 (1981), pp. 220-222.

Eamonn Keough, et al., "An Online Algorithm for Segmenting Time Series," pp. 289-296, 2001.

Penzel, et al., "Computer Based Sleep Recording and Analysis," Sleep Medicine Review 4:2 (2000), pp. 131-148.

Tesler, et al., "Can One Detect Sleep Stage Transitions for On-Line Sleep Scoring by Monitoring the Heat Rate Variability?" Somnologie 8 (2004), pp. 33-41.

A.K. Jain, et al., "Data Clustering: A Review," ACM Computing Surveys, vol. 31, No. 3, Sep. 1999.

http://www.sleepdisorderchannel.net, 2004.

M.G. Terzano, et al., :Atlas, rules, and recording techniques for the scoring of cyclic alternating pattern (CAP) in human sleep, Sleep Medicine 2 (2001), pp. 537-553.

http://www.cs.ubc.ca/~murphyk/Software/HMM/hmm.html.

Sackellares, Iasemidis, et al., "Epilepsy—When Chaos Fails," in "Chaos in the brain," Eds. K. Lehnertz & C.E. Elger, World Scientific, 1999.

Xu-Sheng Zhang, et al., "EEG complexity as a measure of depth of anesthesia for patients," IEEE Transactions on Biomedical Engineering, vol. 48, No. 12, Dec. 2001.

"Sleep related breathing disorders in adults: recommendation for sndrome definition and measurement techniques in clinical research," The Report of an American Academy of Sleep Medicine Task Force, Sleep vol. 22, No. 5, 1999, pp. 667-689.

ADAPTIVE PREDICTION OF CHANGES OF PHYSIOLOGICAL/PATHOLOGICAL STATES USING PROCESSING OF BIOMEDICAL SIGNALS

FIELD OF THE INVENTION

The present invention relates to the field of biomedical diagnosis/prognosis systems. More particularly, the present invention relates to a method for predicting physiological/pathological disorders in a patient, based on sampling, processing and analyzing a plurality of aggregated noisy biomedical signals.

BACKGROUND OF THE INVENTION

Several prevalence pathologies are characterized by prolonged periods of apparent well being, interspersed (or at times, terminated) by sudden, acute and often life-threatening events, such as epilepsy, heart attack and psychotic attacks. Chronic pharmacological therapy, aimed at preventing such events, may compromise life quality during the interim periods. Ability to automatically predict such events on time, for example minutes to hours before these events occur, would open a way to an automated preventing therapy, administered specifically during the pre-event time periods.

Description of Prior Cardiac Arrhythmias Prediction Systems

Cardiac arrhythmias result from abnormal electrical conduction, with or without pacing by multiple abnormal foci. Arrhythmias may vary in severity from mild, in which case no treatment is require, to those that are catastrophic and life threatening. Most life-threatening cardiac arrhythmias (LTCA) involve ventricular fibrillations. Atrial fibrillations are usually not life threatening.

Cardiac rhythm monitoring is mainly performed to prevent death due to LTCA. However, current technologies provide little more than detection and recognition of LTCA once it has started. This leaves very little intervention time; the rhythm must be drastically terminated within minutes by defibrillation ("cardioversion"), or permanent neurological damage, or even death, may occur.

Currently, only one method is in common use to predict an impending LTCA, namely, the frequency and complexity of premature ventricular complexes (PVCs). Existing studies suggest that this method is unreliable, because, in the majority of patients, changes in frequency or complexity of PVCs are not specific to the periods that precede initiation of LTCA, and, therefore, these changes have only poor and unreliable predictive capability.

Methods in general clinical use include simple heart rate detection and, in some cases, repetitiveness of premature ventricular complexes (PVCs). The heart rate detector is set at high and low thresholds by the operator, and an alarm sounds if these thresholds are exceeded. More advanced instruments also alarm when target thresholds for PVC frequency are exceeded. However, these instruments are rather simple, primitive, inaccurate and ineffective. Currently, there is no system for predicting LTCA, only detection once they are in progress. Moreover, the specificity for detection of significant arrhythmias is poor.

Recent research demonstrated that changes in RR-interval (RRI) series might be a more accurate predictor of imminent LTCA than PVCs. However, the complexity and variability of RR-changes in different patients, and even in the same patient in different periods of monitoring, obscured application of this method for prediction of LTCA. Previous studies were focused on the detection of a single type of changes in the RR-series and did not allow identifying both linear and nonlinear changes. This diminished the accuracy of analysis, and made the results applicable to a small number of patients. Frequency components of the RR-series contain physiological/pathologically important information about the activity of autonomic nervous system, which, in turn, plays a major role in the initiation of LTCA. However, the non-stationarity of the signal and the fact that it is not uniformly sampled affects the accuracy of spectral techniques. To overcome this problem, analysis based on Fast Fourier transform (FFT) or autoregressive modeling is usually employed on short and relatively stationary parts, or segments, of the signal. Another approach uses the wavelet transform to decompose the signal into predefined frequency elements. However, neither method allows reliable identification of the frequency elements that exhibit changes before LTCA. The analysis of short time windows requires stationarity of each portion of the signal, whereas the RR-series exhibits pronounced changes preceding LTCA. The wavelet transform decomposes the signal into constant frequency ranges, while individual RR-signals have highly variable frequency content.

The linear changes before LTCA in the majority of patients (80–90%) are not different from those during the arrhythmia-free periods. Because these changes are not specifically associated with LTCA, in the majority of patients they cannot be used for the short-term prediction of arrhythmias. Conventional heart rate variability analysis in the frequency domain has revealed a complex pattern of changes but fails to identify specific changes that might predict LTCA as well. Moreover, the standard time (mean and standard deviation) and frequency (power spectrum) domain representations of a signal do not reveal the non-linear changes that may precede LTCA. Several studies show that utilization of non-linear measures, or features, derived from biomedical signals, significantly enhances the prediction capability, (a reference to an exemplary study may be made to "A reduction in the correlation dimension of heartbeat intervals precedes imminent ventricular fibrillation in human subjects.", J. E. Skinner, C. M. Pratt and T. Vybiral, Am. Heart J. vol. 125, pp. 731–743, 1993).

RR-changes are highly variable, with respect to different persons, and even with respect to the same person over different periods of time, state of sleep, emotional state and degree of exertion, all contribute person-specific changes and perturbations to the classical HRV characteristic of the resting, awake and relaxed state.

It should be appreciated that most LTCAs are expected in patients with very sick hearts. Their "baseline" cardiac activity is very pathological and the transition to the LTCA may be obscured. LTCAs are foremost a result of cardiac pathology rather than a pathology of the neural systems which modulate the cardiac rhythm. The latter may however influence arrhythmogenesis by presenting the sick ventricle with a physiological/pathological rhythm variability that occasionally may induce a LTCA. The system may be viewed as a variable signal passing through a variable filter, with some combinations proving disastrous.

Several important conclusions from previous studies:
1) Since single aberrations as well as physiological/pathological RRI variability information may be important for prediction, the use of constant length segments or windows from which to extract features and perform analysis actually defeats the purpose. For RRI information (especially of very low frequencies), one would wish for the longest possible semi-stationary segments, while for ectopies, the shortest may be desirable, or else, the effect of rare ones would be "diluted" by the prevailing rhythms.

2) A single extracted signal feature may not suffice for obtaining all the relevant cardiac and extra-cardiac information pertinent for prediction.

3) It is almost inevitable that any successful prediction system should be trained on records that were known to be pre-LTCA in the patient who's LTCAs it is trying to predict (i.e., the last hour before a serious VT in a patient's 24 h Holter record). Only that way could a true pre-LTCA state be differentiated from the pathological non-LTCA-related background.

U.S. Pat. No. 5,720,294, of Skinner J E, discloses an electrophysiological analyzer. The system disclosed in U.S. Pat. No. 5,720,294 is based on an "improved" point correlation dimension in which the conventional algorithm is tailored to be insensitive to non-stationarities in the signal. According to this system, correlation dimensions are determined for quasi-stationary sub-epochs of the signal and a dimension <1.2 in the RRI signal predicts fatal arrhythmias. However, this system is more adapted for future risk assessment than for predicting an event in an individual patient, who, during his daily routine, may drop the PD2i for other reasons (exertion, emotional stress etc.). Ectopies, although not being pre-filtered from the RRI series, are still considered a "contamination" to be sidestepped by the algorithm rather than assisting the prediction.

U.S. Pat. No. 6,308,094, of Anderson K P et al, discloses a system for prediction of cardiac arrhythmias. The disclosed system utilizes a single signal, i.e. the RR interval (RRI) time series, and derives information from both linear and non-linear variability of this signal. In particular, the time series is divided into time windows of 5 minutes each, and PCA is employed on each time window, and 2–10 KLT coefficients and eigenvectors are derived there from. Time-varying mean and variances of each coefficient are determined, and when more than 4 coefficients simultaneously vary beyond a threshold (i.e. 3 SD), a life-threatening arrhythmia is predicted by 2–4 hours. However, the prediction capability of the system disclosed in U.S. Pat. No. 6,308,094 is rather poor, because the contribution of a single signal to the prediction process, and, thus to the prediction result, is limited.

Description of Prior Epilepsy Prediction Systems

Epileptic seizures of various types affect 2% of the world population. In addition to patients diagnosed as epileptics, normal subjects may be afflicted by acute seizures, as for instance febrile infants and divers using enriched oxygen mixtures. The latter population would particularly benefit from an early (several minutes) alarm of an impending seizure, as onset prevention may be as simple as reducing the level of exertion and/or the diving depth. Also, a reliable early warning in epileptic patients could radically alter current management by substituting chronic drug therapy application with specific measures to suppress a developing seizure. Currently suggested modes of seizure prediction overwhelmingly rely on information gathered from brain electrical activity, i.e. EEG (See, for example U.S. Pat. No. 3,863,625, to Viglione et al.,"Epileptic seizure warning systems", U.S. Pat. No. 5,720,294, to Skinner J E, "PD2i electrophysiological analyzer", U.S. Pat. No. 5,857,978, to Hively et al., "Epileptic seizure prediction by nonlinear methods", WO 00/10455 to Litt et al., "Method and apparatus for predicting the onset of seizures based on features derived from signals indicative of brain activity", and U.S. Pat. No. 6,304,775 to Iasemidis and Sackellares, "Seizure warning and prediction".

The brain activity information is very often obtained invasively from sub-dural or intra-cranial electrodes. Most algorithms require multi-channel recordings to predict seizures. The types of seizure so far reportedly amenable to forecasting are focal, complex partial seizures.

Several notions form the rationale of the present invention, which are based on the extensive experience of the applicants. The first is the now widely accepted notion that a seizure is a gradual process in which an ever-growing neuronal mass is recruited into synchronous firing. The second is that the brain is an efficient seizure-quencher and that re many would-be seizures are aborted before reaching the critical synchronized mass. This is the basis for entities known as "Pre-ictal Prodromes" one or more of which often precede the seizure by hours or minutes. It is further noted that individual generalized and also focal seizures progress by varied spatio-temporal routes, depending on the composition of the underlying states of the brain—the variability being between as well as within subjects. This notion would speak against a supervised forecasting approach, based on universal criteria, which currently characterizes all EEG forecasting methods and patent claims. Furthermore, it would predict that any proposed forecasting method is bound to miss some seizures.

However, it should be also noted, that with the advancement of epilepsy, and in particular in focal epilepsy, one or more preferred routes that are prone to lead the progression of seizures may develop, thus reducing the likelihood of quenching and gradually increasing the frequency of seizures. It is the last notion that makes us believe that a simple, non-invasive specific alarm, which would even only abort part of the impending seizures at an early stage of the disease, could have a beneficial effect on its course.

In addition, the present applicant believes that, unlike many other organs, malfunctioning of the brain may be evident in signals emanating in other organs (i.e. the heart). Regarding epilepsy, the premise is that neuronal assemblages of the autonomic-system that affect cardiac rhythm and function may be entrained into the epileptic process at a rather early stage. That they indeed form a part of a fully developed seizure is exemplified in the phenomenon of ictal tachycardia, being a doubling or trebling of the baseline heart rate which coincides with, or even precedes by, several seconds the onset of the EEG electric seizure, as is shown in FIG. 43, which shows exemplary partial complex seizure from a patient with focal temporal epilepsy. FIG. 43A depicts an exemplary ECG and left temporal EEG signals. Seizure is shown by the high amplitude swings on the EEG trace. High amplitude swings on the ECG trace are movement artifacts. FIG. 43B shows RRI series which were extracted from the ECG record shown in FIG. 43A. Ictal tachycardia is evident at the time of the seizure (marked by dotted line), and milder tachicardic episodes precede that seizure.

Several reports (i.e. Sackellares, Iasemidis et al.,"Epilepsy—When Chaos fails" in "Chaos in the Brain" Eds. K. Lehnertz & C. E. Elger, World Scientific, 1999) relying on EEG content complexity measures, have shown alleged seizure-connected changes hours and days before its onset. Even accepting the specific seizure-relatedness of such early changes, the practicality of issuing an alarm and taking measures, particularly pharmacological interventions, at this stage is questioned. One major reason being that once anti-seizure medication is instituted, the state of the brain is changed and the forecasting scheme that was developed to detect the seizures of a particular subject may no longer be valid. The applicant believes that this is a weak point in existing epilepsy forecasting from EEG patents and that a period of 20 minutes before the seizure is a practical period in which to issue an alarm and institute preventive measures.

All of the methods described above have not yet provided satisfactory solutions to the problems of obtaining automatic and reliable prediction of changes of physiological/pathological states and automatic adaptation of the predicting system to an individual patient.

It is an object of the present invention to provide a method for obtaining an automatic and reliable prediction of changes of physiological/pathological states.

It is another object of the present invention to provide a method for automatic and reliable prediction of changes of physiological/pathological states that includes adaptation to an individual patient.

Other objects and advantages of the invention will become apparent as the description proceeds.

SUMMARY OF THE INVENTION

The term 'Physiological state' refers to a health state that does not jeopardize the wellbeing of an organism being in that state. The term 'Pathological state' refers to a health state that jeopardizes the wellbeing of an organism being in that state. The term 'State change' refers to transition between any two different physiological/pathological states. The term 'Adaptation' refers to convergence of an expert system to intrinsic attributes of a monitored individual. The term 'Biomedical signal' refers to a signal, whether self-emitted or induced, that emanates from an organism.

The present invention is directed to a method for predicting changes of physiological/pathological states in a patient, based on sampling, processing and analyzing a plurality of aggregated noisy biomedical signals.

The method disclosed in the present invention is characterized by allowing identifying physiological/pathological information that precedes physiological and pathological states, such as heart attacks and epilepsy. The latter physiological/pathological information is derived from several types of biomedical signals that originate from an affected organ, or, indirectly, from an organ whose activity is modulated by the affected organ.

The terminology 'feature' refers to a signal that is, or could be, obtained directly from an electric signal that represents a corresponding biomedical signal, such as ECG, EEG, Oximetry, blood pressure, respiratory, etc. (i.e., such feature is herein referred to as "initial feature signal"), and/or a signal that is, or could be, obtained indirectly from biomedical signals (i.e., by utilization of one or more initial feature signals). The latter type of feature is herein referred to as "secondary feature". In addition, a secondary feature signal may be utilized for deriving additional secondary features, in hierarchical manner, and, in fact, a new secondary feature may be derived from any combination of initial and/or previous secondary features, provided that the new secondary feature has medical meaning and/or is helpful in prediction of physiological and/or pathological states of interest. Referring to an ECG signal, an exemplary initial feature could be the Heart Rate (HR) or the shape of a heartbeat, or of portions thereof, while an exemplary secondary feature could be the Heart Rate complexity index, variance, duration, etc. According to the method disclosed in present invention, a collection of features is selected in a way that for a given physiological/pathological state, the occurrence of which is to be predicted, the collection of features will yield an optimal prediction result.

Preferably, the method for predicting changes of physiological/pathological states in a patient comprises:

a) Generating a reference database of data streams and/or features, derived from the data streams, representing physiological/pathological states, by aggregating one or more raw data streams, each of which consisting of biomedical signals of a plurality of patients, at least several of which having one or more of the physiological/pathological states, wherein the features are obtained by performing, for each type of biomedical signal, adaptive segmentation of its corresponding raw data streams, and assigning, to each segment, individual attributes being represented by attribute values, thereby obtaining data related to each physiological/pathological states;

b) determining an attribute domain, in which each segment being represented by a point that corresponds to the attribute values of the segment;

c) for each physiological/pathological state, generating a set of clusters in the attribute domain, each of which consisting of a combination of points determined by their relative location to other points, by assigning a set of property values to each point, each property value corresponding to the degree of association of the point with one of the clusters;

d) associating each point, in time, to a corresponding state;

e) determining the probabilities of transitions between states by obtaining the frequency and the order of appearance of each point, in time;

f) repeating steps c) to e) above while in each time, varying the combination of points included in each cluster according to their most updated property value and by including points derived from the probability until the updated property values remain essentially unchanged, thereby updating each cluster and the probabilities of transitions;

g) generating prior knowledge data, consisting of a plurality of feasible paths between states according to the probabilities of transitions, by associating each feasible path with a corresponding dynamics of transitions between physiological/pathological states;

h) associating at least one updated cluster with a normal/abnormal physiological state of the patient by using former knowledge, regarding normal/abnormal physiological/pathological states;

i) For each patient, j) aggregating one or more individual data streams and/or features, derived from the individual data streams, each of which consisting of biomedical signals of the patient, wherein the features are obtained by performing, for each type of biomedical signal, adaptive segmentation of its corresponding raw data streams, and assigning, to each segment, individual attributes being represented by attribute values;

k) assigning each individual attribute to a corresponding state, or to a new state, according to the probability to belong to each existing cluster or to a new cluster associated with the new or existing state and the probabilities of transitions;

l) adaptively updating each existing and/or new cluster and the probabilities of transitions according to the individual data streams;

m) obtaining a path, being an individual dynamics, between physiological/pathological states according to their order of appearance; and n) obtaining a prediction of being in, or transitions to, physiological/pathological states in the patient, by comparing the individual dynamics with known dynamics, obtained from prior knowledge.

Preferably, the method further comprises:
a) Whenever new individual attributes do not belong to an existing cluster, defining one or more new states and transition probabilities between existing states and/or new states;
b) Obtaining an updated path between the existing states and/or new states according to their order of appearance;
c) Associating the updated path with an updated individual dynamics of transitions between physiological/pathological states; and
d) Obtaining an updated prediction of physiological/pathological states in the patient, according to the updated individual dynamics and the prior knowledge.

Preferably, whenever the most feasible path is a new path reflecting transition between existing states, the method further comprises:
a) associating the new path with a new individual dynamics of transitions between physiological/pathological states; and
b) Obtaining a new prediction of physiological/pathological states in the patient, according to said new individual dynamics and the prior knowledge.

In order to allow adaptation of the prediction process to a monitored patient, the method further comprises updating the reference database, the existing and/or new clusters, the transition probabilities between existing and/or new states, and the dynamics of transitions between existing and/or new physiological/pathological states.

Preferably, the types of biomedical signals are selected from the group:
ECG signal;
EEG signal;
Respiratory signal;
EOG signals;
Acoustic signals;
Oximetry;
Blood pressure;
EMG;
$CO_2$; and
Body movement/position Preferably, features that are obtained from data streams that are related to the biomedical signals are:

Spectrum Analysis Features
Zero crossing;
Estimated AR power spectrum;
Relative peak level of each frequency band;
Relative energy level of each frequency band;
Fundamental frequency;
Number of substantial frequencies; and
Frequency group classification.

Temporal Analysis Features
Maximum and minimum amplitude;
Maximum and minimum energy;
Number of substantial peaks;
Mean, variance and skewness amplitude;
Duration in seconds and in samples;
Transient level (derived from the adaptive segmentation algorithm);
Peak to peak maximum amplitude and duration;
First derivative (Slope);
Second derivative;
Wavelets coefficient calculation;
PCA coefficient calculation; and
Matching pursuit based segment decomposition.

Non-linear Dynamics Features
The Lempel-Ziv complexity measure;
Fractal dimension;
Lyapunov exponent; and
Density estimation of phase space derived features like entropy.

Preferably, adaptive segmentation of ECG signals comprises:
a) generating several signals from the raw ECG signal, wherein in each signal a different frequency content being emphasized;
b) summating the corresponding absolute values of the signals;
c) filtering the resulting summation; and
d) employing local maxima detection method, for identifying the R-peaks, P-peaks and T-peaks in the filtered resulting summation, the R, P and T peaks being utilized for characterizing the corresponding heartBeats Under Test (BUTs), the P and T peaks being utilized also for further segmentation of heartbeats.

Preferably, obtaining features from ECG signals comprises the steps:
a) detecting 'R—R' time-intervals between each two consecutive R-peaks; and
b) identifying characterizing points 'P', 'Q', 'S' and 'T' of the corresponding BUTs, by utilizing the 'R—R' time-intervals, at least some of the points being utilized for obtaining features related thereto.

Preferably, identifying the R-peaks in the acquired ECG signal is carried out by utilizing the Wavelet Transform Process and several scales associated with the R-peaks.

Preferably, the features that are obtained from an ECG signal are:
a) The general shape of PQRST complex, which is obtained by utilizing pattern recognition technique, the Wavelets algorithm, and PCA;
b) Intervals. For example, RR, ST and QT;
c) Interval differences. For example, RR-QT (coupling interval);
d) Interval ratios. For example, QT/RR, PQ/RR;
e) Differentials of 'nth' order (n=1,2, . . . etc.) of consecutive intervals. For example, first and second order of consecutive of R—R Intervals: diff[RRI(n)], $diff^2$[RRI(n)];
f) Absolute value of the differentials mentioned in e). For example, |diff[RRI(n)]|, |$diff^2$[RRI(n)]|;

The features in e) and f) that appear immediately above may be obtained with respect to:
(1) Single heartbeats;
(2) Heartbeat ensemble averages, variances and RMS of differences;
(3) Heartbeat ensemble distributions.
g) Linear and non-linear dynamic features from an interval time series function (i.e., RRI). For example, zero crossings, PCA and Wavelet coefficients, AR power spectrum estimation, correlation dimensions, etc.

Preferably, adaptive segmentation of EEG signals comprises utilization of a first and a second time-windows, the time-width and relative location being varied until a decision, regarding the optimized location of the boundaries of each EEG segment, is determined, based on the comparison between the statistical properties of a first EEG signal portion contained in the first time-window to the statistical properties of a second EEG signal portion contained in the second time-window.

Preferably, the comparison (i.e., between the statistical properties of a first EEG signal portion to the statistical properties of a second EEG signal portion) is implemented using the GLRT and KLD measures.

Additional features may be obtained from Respiratory signals. Of particular importance are the respiratory rate (RR) and respiratory rate variability (RRV). Several modalities may provide the qualitative contour of the Respiratory cycle (e.g., nostril temperature, trans-thoracic impedance, circum-chest strain gage tension, intra-cardiac pressure, etc.). The slope of the Respiratory curve at a given time instant of each heartbeat may be used as a co-input to the clustering algorithm, together with the ECG.

Preferably, adaptive segmentation of respiratory signals comprises:
  Detection and Smoothing of the envelope of the chest and abdomen effort signals, air pressure flow signal, and thermistor flow signal;
  Peak Detection and Maximum Setting of the envelope signal; and
  Identifying two consecutive global maxima points, the points defining the temporal boundaries of a corresponding segment of the envelope.

Additional features may be obtained from Acoustic signals, which correspond to: (1) beat-induced intra-cardiac sounds, and (2) Doppler-shift effect of intra-vascular (coronary) blood flow. Accordingly, spectral features are obtained from (1) above, and peak velocities are obtained from (2) above.

Preferably, the set of clusters is generated by employing un-supervised fuzzy clustering algorithm on the points residing within the corresponding attribute domain.

After obtaining features from the various data streams, the features are classified in order to estimate the current physiological/pathological state of the monitored patient.

Preferably, the classification of the extracted (i.e., obtained) features is implemented by utilization of one or more HMM models, each of which could be characterized by having different number of states and free parameters (e.g., covariance matrices, mean vectors, matrix of state transition probabilities and matrix of observation probability distribution).

Different HMM models may be trained to characterize different global physiological/pathological behavior, which may be associated with, e.g., specific group of population, sleep stage or any health condition.

Preferably, the prediction process utilizes one or more HMM models and one or more sets of fuzzy logic rules that are employed on other factors/features, such as (1) pathological heartbeats, (2) patient's weight and/or height and/or general health/condition, (3) blood pressure, (4) sleep stage, and (5) oxygen in the blood, in order to obtain a more reliable prediction result.

Optionally, different mixtures of HMM model(s) may be utilized, each of which could be optimal with respect to different monitoring stages, time epochs and biomedical signals.

Preferably, the method further comprises:
a) Generating, in real-time, alert indication in response to predicted pathological, dangerous, or any other wanted state; and
b) Automatically transmitting the indication to a physician over a data network, for determining/providing the required medical treatment.

Preferably, the method further comprises dynamically controlling the operation of a medical apparatus used for providing medical treatment to a patient being monitored, in response to identified pre-pathological state(s) in the patient, for preventing the occurrence of the pathological state(s).

Preferably, the medical apparatus is an apparatus that is selected from the following group of apparatuses, or an apparatus operable using combined principles of several of these apparatuses:
  Controllable drug dosage devices;
  Controllable gas/air delivery devices;
  Continuous Positive Airway Pressure (CPAP);
  Bi-level positive airway pressure (BPAP);
  Implantable/non-implantable Respiratory Stimulator;
  Implantable/non-implantable Brain/Nerve Stimulator/Pacers;
  Implantable/non-implantable cardiac defibrillators (ICD)/cardiac pacers/Cardiac Resynchronization Therapy (CRT).

The present invention is also directed to a system for predicting changes of physiological/pathological states in a patient, based on sampling, processing and analyzing a plurality of aggregated noisy biomedical signals.

Preferably, the system comprises:
Data acquisition means for collecting biomedical signals of one or more patients;
A database of data streams and/or features, derived from said data streams, representing physiological/pathological states, said database aggregates one or more raw data streams, each of which consisting of said biomedical signals of a plurality of patients, at least several of which having one or more of said physiological/pathological states, said database being capable of storing data streams and/or features which are used as reference data streams and/or features for characterizing further individual patients and for storing data streams and/or features of individual patients;
Processing means for obtaining said features by performing, for each type of biomedical signal, adaptive segmentation of its corresponding raw data streams, and assigning, to each segment, individual attributes being represented by attribute values, and for obtaining data related to each physiological/pathological states; and
Additional processing means for determining an attribute domain, in which each segment being represented by a point that corresponds to the attribute values of said segment; for generating a set of clusters in said attribute domain for each physiological/pathological state wherein each of which consisting of a combination of points determined by their relative location to other points, for assigning a set of property values to each point, wherein each property value corresponding to the degree of association of said point with one of the clusters; for associating each point, in time, to a corresponding state; for determining the probabilities of transitions between states by obtaining the frequency and the order of appearance of each point, in time; for varying the combination of points included in each cluster according to their most updated property value and for including points derived from said probability until said updated property values remain essentially unchanged, so as to update each cluster and said probabilities of transitions; for generating prior knowledge data, consisting of a plurality of feasible paths between states according to said probabilities of transitions, by, and for associating each feasible path with a corresponding dynamics of transitions between physiological/pathological states; for associating at least one updated cluster with a normal/abnormal physiological state of said patient by using former knowledge, regarding normal/abnormal physiological/ pathological states; for performing, for each type of biomedical signal, adaptive segmentation of its corresponding raw data streams, and for assigning, to each segment, individual attributes being represented by attribute values, for assigning each individual attribute to a corresponding state, or to a new state, according to the probability to belong to each existing cluster or to a new cluster associated with said new or existing state and said probabilities of transitions; for adaptively updating each existing and/or new cluster and said probabilities of transitions according to said individual data streams; for obtaining a path, being an individual dynamics, between physiological/pathological states according to their order of appearance, and associating said most feasible path with an individual dynamics of transitions between physiological/pathological states; and for obtaining a prediction of being in, or transitions to, physiological/pathological states in said patient, by comparing said individual dynamics with known dynamics, obtained from prior knowledge.

Preferably, the system further comprises processing means for defining one or more new states and transition probabilities between existing states and/or new states whenever new individual attributes do not belong to an existing cluster; obtaining an updated path between said existing states and/or new states according to their order of appearance; for associating said updated path with an updated individual dynamics of transitions between physiological/pathological states; and for obtaining an updated prediction of physiological/pathological states in said patient, according to said updated individual dynamics and the prior knowledge.

Preferably, the system further comprises processing means for associating the new path with a new individual dynamics of transitions between physiological/pathological states; and for obtaining a new prediction of physiological/pathological states in said patient, according to said new individual dynamics and the prior knowledge, whenever the updated path is a new path reflecting transition between existing states.

Preferably, the system further comprises processing means for updating the reference database, the existing and/or new clusters, the transition probabilities between existing and/or new states, and the dynamics of transitions between existing and/or new physiological/pathological states.

Preferably, the system further comprises processing means for generating, in real-time, alert indications representing abnormal physiological events; and for automatically transmitting the indications to a physician over a data network, for determining/providing the required medical treatment.

Preferably, the system further comprises processing means for dynamically controlling the operation of a medical apparatus used for providing medical treatment to a patient being monitored, in response to identified pre-pathological state(s) in the patient, for preventing the occurrence of the pathological state(s).

BRIEF DESCRIPTION OF THE DRAWINGS

The above and other characteristics and advantages of the invention will be better understood through the following illustrative and non-limitative detailed description of preferred embodiments thereof, with reference to the appended drawings, wherein.

DETAILED DESCRIPTION OF PREFERRED EMBODIMENTS

The present invention is characterized by introducing a system that is capable of automatically predicting physiological/pathological disorders while adapting itself to at least the inherent cardiac, sleeping and respiratory status of individual patients, without having to manually match new sets of thresholds (on a 'trial and error' basis) for different patients being monitored.

Figure 1:
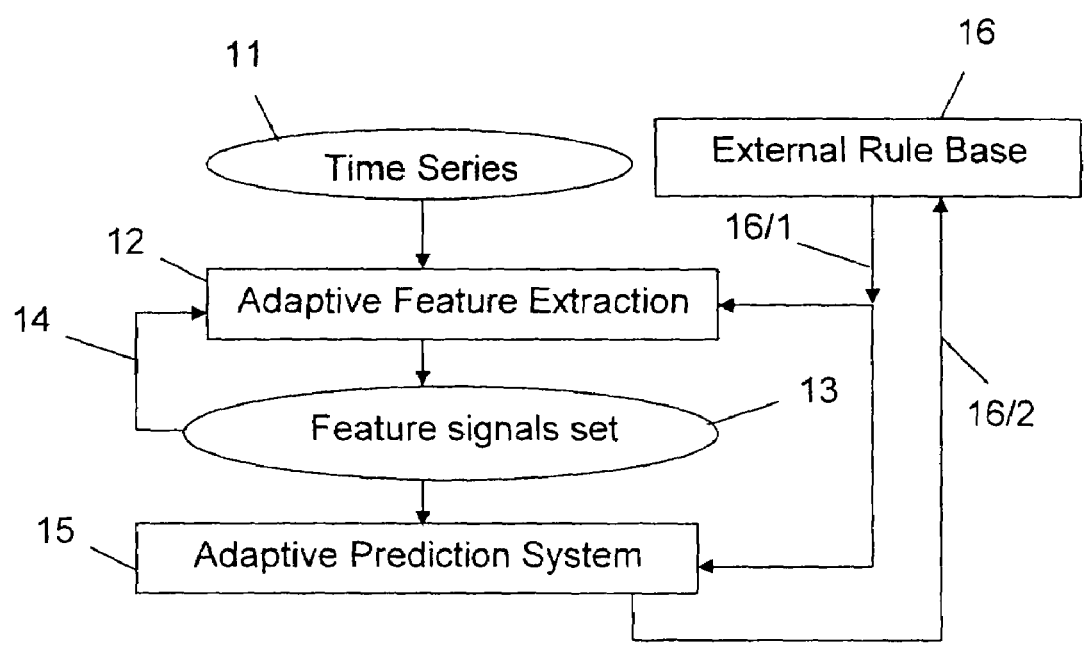
FIG. 1 schematically illustrates a general layout and functionality of the present invention.

FIG. 1 schematically illustrates a general block diagram of the present invention. In step 11, at least one time series is obtained, which could correspond to, e.g., an ECG signal. A time series is obtained from a corresponding electrical signal that represents a biomedical signal, by sampling the aforesaid electrical signal. The sampling frequency depends on the behavior of the related biomedical signal, and it also complies with the known Niquist criteria. In step 12, the time series obtained in step 11, undergoes "Adaptive Feature Extraction" (AFE) process, which is described immediately herein below. Immediately after obtaining the time series, first features are extracted in step 12 (herein referred to as the "initial features"), which are directly related to the sampled signals. For example, such features may be the morphology of heartbeats and/or shape of portions of heartbeats, and/or heartbeat rate, all of which are derived, in this example, from ECG signals. Initial features are, of course, extracted from other types of signals (e.g., EEG, respiratory). The present invention is characterized by utilizing, for the medical prediction, additional features (herein referred to as the "secondary features"), which are obtained from one or more initial features (in step 13). Of course, additional features may be derived from the secondary features, and this principle may be repeated as many times as required, as indicated by reference numeral 14, provided that the derived features have any medical meaning.

The features obtained in steps 12 and 13 will be utilized for predicting pathological events in a patient. In order to accomplish the prediction process, these features are fed to the Adaptive Prediction System (APS), in step 15, where they are analyzed and classified, after which the APS decides as for the present physiological/pathological state of the monitored person. The latter decision is base on data gathered up to the decision moment.

Optionally, an External Rule Base (ERB) may be utilized for optimizing the prediction process, by initializing the AFE (12) and APS (13) with optimal parameters. The ERB may be also utilized also for setting limits so that the APS (15) will not diverge, or in cases where initial prediction results are not satisfactory.

General—Adaptive Feature Extraction

Electrophysiological signals, such as EEG and ECG signals, and signals that are derived from such signals (e.g., R—R Interval—RRI, that is derived from ECG signal), have both linear and nonlinear dynamical properties of differing complexities. The complexity degree and the relative expression of linear and chaotic features which are extracted from the time series representing the electrophysiological signals, are time-varying during the normal diurnal cycle, and become more so with chronic pathology. In the advent of an impending pathological event, changes are unpredictable and frequently irreproducible, with evidence of both increases and decreases in signal complexities. Considering the above, a combined linear and nonlinear dynamics feature extraction and manipulation may be a better approach than any one alone, in characterizing the intrinsic nature of those signals as a combined tool for prediction.

For each electrophysiological signal, one, some or all features are extracted for further prediction analysis. A classification process is employed on the extracted features, for allowing clustering corresponding segments of the time series. An advantage of the clustering process is that it can accommodate any number of different and unrelated inputs, each of which could occupy a different dimension in a phase space wherein it is applied. Exact feature extraction is obtainable through the use of accurate segmentation, advanced patient adaptation, and environmental-dependent analysis. Consequently, each specific record of the signal is adaptively segmented and identified.

Adaptive segmentation plays a major role in the present invention, because the more accurate the segmentation process, the more accurate the features (i.e., that are extracted from the segments) are, resulting in a more accurate decision regarding the prediction of physiological/pathological disorders.

Figure 2:
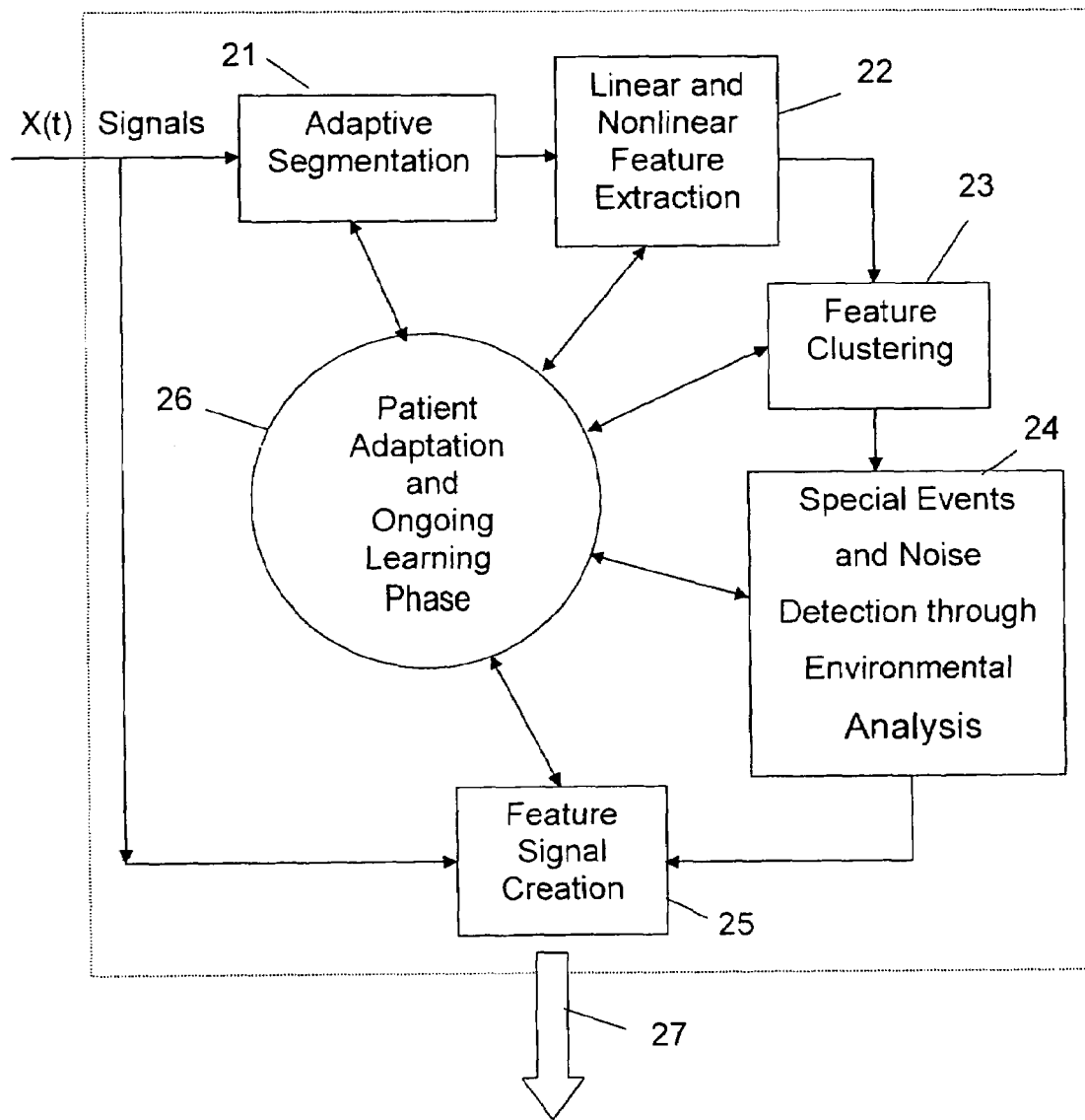
FIG. 2 schematically illustrates in more details the layout and functionality of the Feature Extraction Layer, according to an embodiment of the present invention.

FIG. 2 schematically illustrates in more details the Feature Extraction Layer shown in FIG. 1 (reference numerals 12 to 14). Adaptive segmentation process 21 is employed on each type of biomedical signal that is monitored by the system. Several types of adaptive segmentation processes are utilized by the present invention, each of which is customized to the type of the monitored biomedical signal. The motivation for utilizing adaptive segmentation tools is the following—Stationary behavior of a windowed time series is a necessary condition for unbiased parameter estimation. Also, the ability to trap transient phenomena (in, e.g., EEG signal), such as epileptic spikes, or aberrant beats in the RRI series, is of great importance to the medical prediction process. Therefore, it is required to adaptively partition the (essentially un-stationary) time series into corresponding quasi-stationary segments. Each identified quasi-stationary segment allows extraction of features there from by utilizing statistical and other mathematical tools.

There are two adaptive segmentation algorithms that are utilized by the present invention; i.e., the Generalized Likelihood Ratio (GLR) and KullBack Leibler Divergence (KLD) based algorithm, and Adaptive Segmentation algorithm that is Based on Temporal Signal Behavior.

1) Adaptive Segmentation Based on GLR and KL Divergence

Stationary behavior of a windowed time series is a necessary condition for unbiased parameter estimation. Also, the ability to trap transient phenomena like epileptic spikes in the EEG signal or aberrant beats in the RRI series is an important prediction tool. Thus it is important to adaptively partition the time series into quasi-stationary segments. The adaptive segmentation algorithm utilized is based on a generalized likelihood ratio (GLR) and KullBack Leibler divergence as described herein.

2) Adaptive Segmentation that is Based on Temporal Signal Behavior

There are signals that are better defined and segmented by their temporal linear behavior. The adaptive segmentation algorithm employed on those signals is based on knowing the temporal behavior and physiological/pathological/clinical significance of the resulting segments. For example, an ECG signal is relatively easily segmented, in a first segmentation process, into heartbeats, which are not necessarily quasi-stationary segments, and each heartbeat is further segmented, in a second segmentation process, into physiological/pathologically significant segments, such as PR, QRS, QT, ST, etc. The first segmentation process (i.e., into heartbeats) is based on detection of "R-waves" of the heartbeats and is carried out by employing the known "Wavelet Transform Algorithm" on the ECG signal. The second segmentation process (i.e., into PR, QRS, etc.) is based on temporal linear analysis and a-prior physiological/pathological knowledge of the universal heartbeat morphology.

Figure 3:
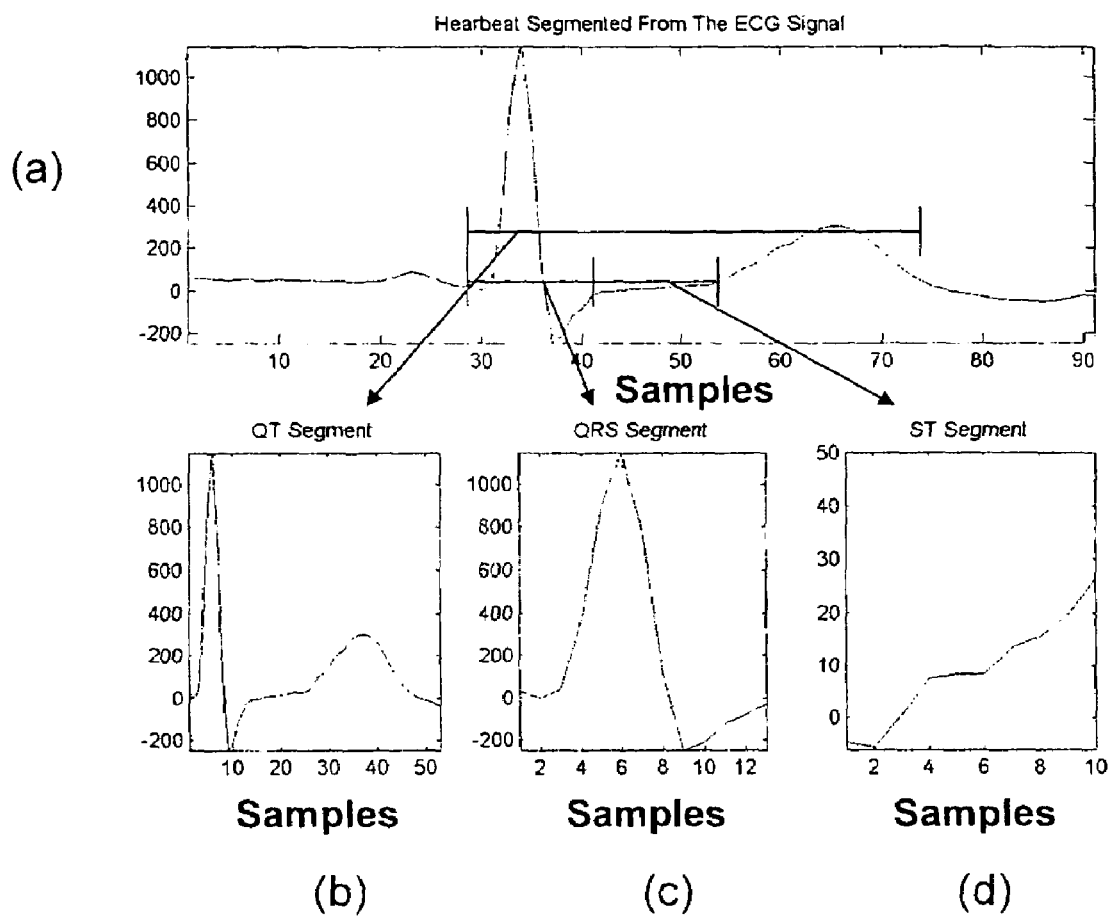
FIG. 3 schematically illustrates typical shape of a heartbeat, with its QT, QRS and ST portions magnified.

FIG. 3a illustrates an exemplary adaptive segmentation based on temporal signal behavior. According to this example, one heartbeat was "segmented out" of an ECG signal by employing the first segmentation process mentioned above; i.e., a segmentation process based on detection of "R waves". FIGS. 3b, 3c and 3d show exemplary QT, QRS and ST segments that were "segmented out" of the heartbeat shown in FIG. 3a, by employing the wavelet based segmentation process mentioned above.

Referring again to FIG. 2, After employing adaptive segmentation process (in step 21) on the corresponding signal x(t), which could represent any known biomedical signal (e.g., ECG, EEG, etc.), one, some or all of the features described herein are extracted from each identified segment, by employing a corresponding analysis (i.e., spectrum or temporal analysis):

Spectrum Analysis—the spectrum analysis includes extraction of at least the following features:
Zero crossings;
Estimated AR power spectrum;
Relative peak level of each frequency band;
Relative energy level of each frequency band;
Fundamental frequency;
Number of substantial frequencies; and
Frequency group classification.

The frequency group classification process and its task are described in IL Patent application No. 147502.

Temporal Analysis—the temporal analysis includes extraction of at least the following features:
Maximum and minimum amplitude(s);
Maximum and minimum energy;
Number of substantial peaks;
Mean, variance and skewness amplitude;
Duration in seconds and in samples;
Transient level (derived from the adaptive segmentation algorithm);
Peak to peak maximum amplitude and duration;
First derivative (Slope);
Second derivative;
Wavelets coefficient calculation;
Principal Component Analysis (PCA) coefficient calculation;
Matching pursuit based segment decomposition, as described herein below.

The feature extraction process disclosed herein is very accurate because of the advanced adaptive segmentation process employed on the biomedical signal(s), and because the system has disease-related and patient-specific adaptive learning capabilities. Whenever the system is connected to a patient that is not known to the system, the system is first initialized with a universal a-priori knowledge that was derived from several patients that experienced similar events in the past. Optionally, the system may be initialized with a set of rules or initial conditions which will be utilized in the features-extraction process. Yet, because of short-term and long-term variability in the biomedical behavior in a patient, and variability between patients, a more accurate feature extraction result is obtained by automatically and adaptively converging to the patient's specific physiological/pathological behavior during event-free periods. Furthermore, the system keeps on updating (i.e., training) itself by referring to additional clinically significant changes that would be used for predicting future events. An example for automatic convergence of a similar system to ECG morphology of individual patient is described in connection with FIG. 1 of Israeli Patent application No. 147502 of the same applicant.

As explained before, in order to obtain an accurate prediction of pathological events, a combined linear and nonlinear dynamic feature extraction and manipulation process is performed. However, since signals having non-linear dynamic behavior (such signals being generally referred to as chaotic signals), which play a major role in the prediction of pathological events, behave in a manner that does not allow them to be analyzed by mathematical tools meant for signals having linear dynamic behavior (e.g., Fourier analysis), a different analyzing mechanism is employed with this regard; i.e., the nonlinear portion of the prediction process is handled by evaluating the fractal dimension and/or the complexity measures of the related chaotic signals. The higher the fractal dimension or the complexity measure, the more the related chaotic signal is considered complex. According to the present invention, the complexity evaluation is carried out by utilizing two known complexity analyzing tools; (1) Lempel-Ziv (LZ) complexity analysis; and (2) Fractal Dimension (FD) analysis.

(1) The Lempel-Ziv Complexity Analysis

Lempel-Ziv complexity analysis is based on a 'coarse-graining' of the measurements, i.e., the signal to be analyzed is transformed (compressed) into a sequence whose elements are chosen from a few symbols. The complexity counter c(n) measures the number of distinct patterns contained in a given sequence. Briefly described, a sequence $P=s_1,s_2,\ldots,s_n$ is scanned from left to right and the complexity counter c(n) is increased by one unit every time a new (sub-sequence?) of consecutive characters is encountered in the scanning process. After normalization, the complexity measure C(n) reflects the rate of occurrence of a new pattern with time. A reference for exemplary use of Complexity may be made to "Xu-Sheng Zhang, Rob J. Roy and Erik Weber Jensen *EEG Complexity as a Measure of Depth of Anesthesia for Patients*". IEEE TRANSACTIONS ON BIOMEDICAL ENGINEERING, VOL 48, NO. 12, DECEMBER 2001".

(2) Fractal Dimension Analysis

The term "fractal dimension" refers to a non-integer or fractional dimension of any object, and it relates to the number of parameters that govern the dynamics of nonlinear systems.

Applications of FD in this setting include both a temporal approach that estimates the FD of a waveform, and phase space analysis, which estimates the FD of an attractor. Calculating the FD of waveforms is useful for transient detection, and it involves estimation of the dimension of a time varying signal directly in the time domain. The phase space representation of a non-linear system usually describes an attractor with a given fractional dimension. This attractor dimension is essentially invariant, even under different initial conditions and this is why it is widely used for system characterization. The physical meaning of the attractor's FD is the minimum number of parameters that govern the attractor's dynamics. The most common methods for FD calculation are the Higuchi's algorithm, Petrosian's algorithm, Katz's algorithm and Grassberger-Procaccia algorithm. Refer to "Non Linear Biomedical Signal Processing" Volum 2 chapter 1.

In order to enrich the collection of features, and, thereby, to enhance the medical prediction process, a Density Estimation of Phase Space (DEPS) processes having similar complexity dimensions that could not be otherwise distinguished from one another. The term 'phase space' refers to a space describing the behavior of several parameters relating to a common phenomenon. Exemplary parameters are x(t) and v(t), which describe the distance and the velocity of a same object, respectively.

Density Estimation of Phase Space (DEPS)

According to the novel method disclosed herein, the density of the phase space attractor's trajectories (reconstructed using known embedding dimension method) of a time series is estimated using non-parametric methods like non-parametric kernel density and parametric methods like fitting a Gaussian mixture of models by using unsupervised fuzzy clustering algorithms. Calculation of density derived parameters like entropy and statistical independence are utilized for characterization of the processed time series. Measuring the Kullbak-Leibler divergence or correlation between densities of adjacent segments can be used for detection of changes in the time series behavior.

Figure 44:
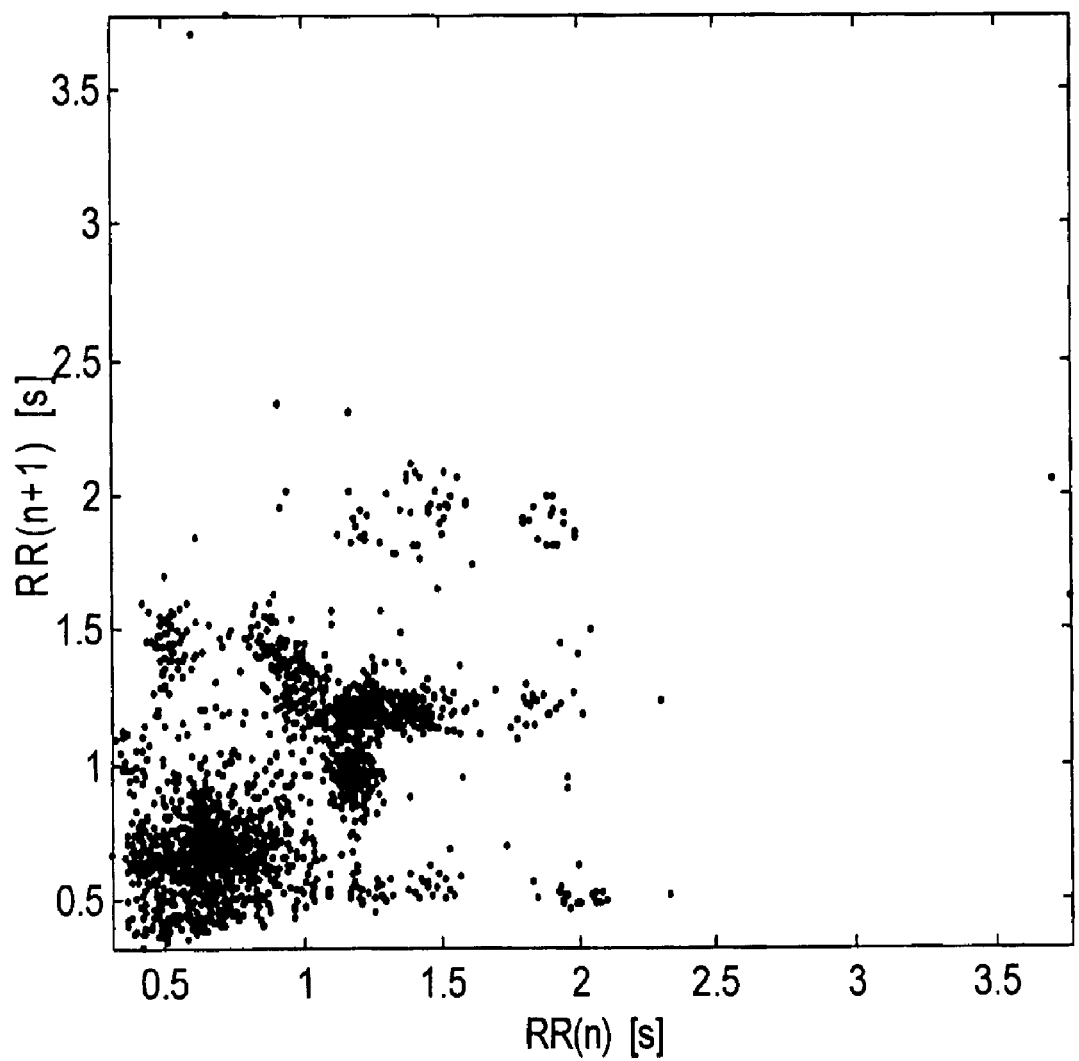
FIG. 44 depict exemplary data points that are to be clustered, according to the present invention.

The template structure of any state space is defined in greater detail by clustering of the points occupying it. For example, the final product from a conventional 24-hour Poincaret plot of RRI (RRn vs RRn+1) of normal person usually appears as a single comet-like shaped or torpedo-like shaped cluster. Shorter records, which include conspicuous, recurrent and reproducible rhythm disturbances (i.e. ectopies), yield more details, which lend their selves to either crisp or more often, to fuzzy partitioning (as shown in FIG. 44). By 'Fuzzy partitioning' it is meant that a data point might belong to more than one Gaussian, or cluster. For example, a data point may belong to a first Gaussian/cluster with a first probability value (e.g., 0.1), to a second Gaussian with a second probability value (e.g., 0.6) and to a third Gaussian with a third probability value (e.g., 0.3).

There are complexity measures such as the "scaling index" and "net information flow" defined in G. Schmidt and G. E. Morfill, "Nonlinear methods for heart rate variability assessment." In: M. Malik, and Camm A. J. (Eds.), Heart rate variability. Futura Publ., Armonk, N.Y., pp. 87–98, 1995, that are useful for bringing out detail in RRI phase space, yet, an unsupervised method that seeks and defines the "centers of gravity" of the point-cloud occupying the space has a better fine-structuring capacity as well as the ability to distinguish between point arrays of equal complexity.

Referring again to FIG. 2, after extraction of the features in step 22, the features are clustered (step 23) using unsupervised fuzzy clustering; i.e., features having essentially similar statistical properties are grouped together. The degree of membership of each feature in each one of the clusters can be a new feature by itself There are different clustering criteria, which are related to different types of biomedical signals. For example, one such criterion is heart morphology, which is characterized by utilizing Template Matching algorithm, Minimum Model Derived Distance algorithm, spectrum behavior etc as described herein.

The classification results are based on morphology groups (based on matching template criteria), such as those existing in ECG and respiratory signals, frequency bands and groups such as in the EEG (based on energy and frequency activity behavior), pathological event types such as in the respiratory analysis (based on Minimum Model Derived Distance criteria and on the spectrum behavior), different nonmalignant transient activity, such as the transient activity of the brain.

Figure 37:
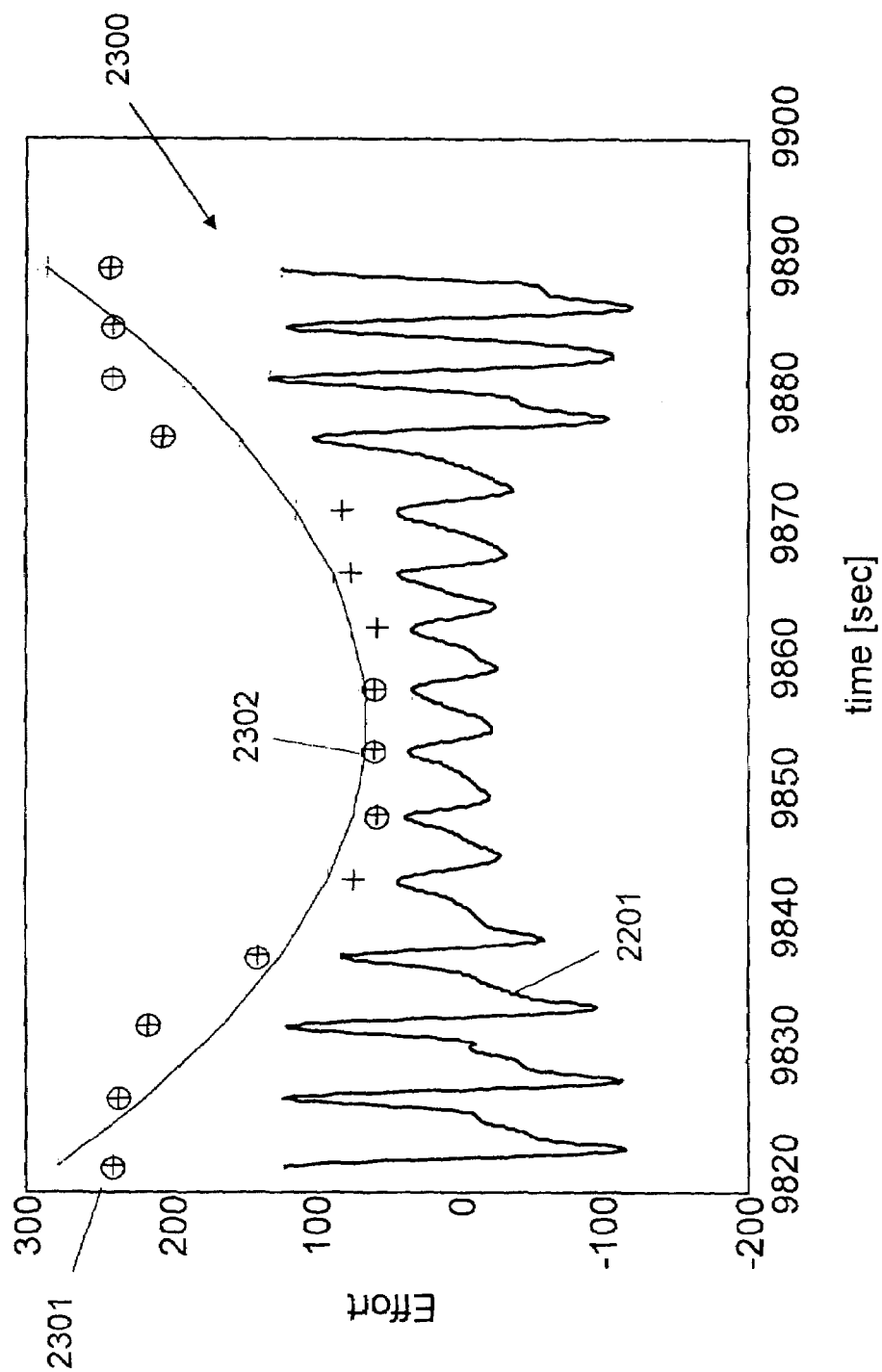
FIG. 37 illustrates utilization of parabola for signal trend evaluation, according to a preferred embodiment of the present invention.

A notion of exemplary Energy and Frequency Activity behavior of EEG signal is described in IL Patent application No. 147502, in connection with FIG. 37. A notion of exemplary Frequency group association (i.e., Low, Medium and High frequency groups) relating to EEG signals is described in IL Patent application No. 147502. A notion of exemplary ECG morphology detection is described in IL Patent application No. 147502, in connection with FIGS. 1(c) to 1(e), and a notion of Respiratory morphology detection as described herein.

It is essential that before a feature is considered viable (i.e., a feature that is essentially noiseless and artifact-free), is used for classification, a decision has to be automatically made by the predicting system, whether the extracted feature is an artifact, in which case it will be disregarded, or whether it contains noises, in which case the behavior of the adjacent relevant segments will assist in deciding whether viable features could be extracted from the related segments. Therefore, a continuous environmental analysis is also performed (see FIG. 2, reference numeral 24).

It is important that the features of each segment are compared to coexisting environmental features that are derived from the same segment, in order to determine whether the feature(s) is viable or not. Environmental features may include instrumental background electrical activity or noise, as well as simultaneous electrophysiological signals (e.g., muscle or movement artifacts) that distort the signal of interest (e.g., ECG).

The feature extraction process may be biased because of an inaccurate classification of the segment due to a problematic environment. For example, a sever noise may cause a segment to be identified by the system as an aberrant heartbeat morphology, and the 'aberrant heartbeat' may yield features that may erroneously identify it as pathological. To overcome this problem, all segments are identified in relevance to the amount of high frequency and low frequency artifacts. For example, in the EEG signal, a transient morphology segment may be erroneously identified as one of the physiological/pathological transient components such as K-complex, but due to the environmental analysis around this transient segment, which allows the system to detect a very noisy environment, the system is capable of classifying the transient activity as an artifact. From the above description and examples, the importance of the environmental-dependent feature extraction is clear for further analysis of predicting pathological events. An exemplary "K-Complex" is described in IL Patent application No. 147502, in connection with FIG. 35.

An integral and essential part of the features extraction stage is driving, from features obtained from raw biomedical signals (being herein referred to as the "initial" features), various new features signals of medical importance (being herein referred to as the "secondary features signals"). It should be noted that additional features signals may be derived from secondary features signals, and so on, for enhancing the pathological prediction process and thereby, obtaining more accurate prediction results. However, only features signals having meaningful medical significance are to be chosen for prediction purposes. Accordingly, after filtering out noises and environmental artifacts, in step 24 (FIG. 2), essentially noiseless and artifact-free features are obtained, which could be utilized for generation of new features (i.e., secondary features) there from (reference numeral 25).

Secondary, or new, features signals bear information that can not be easily observed from the source signal it was derived from (i.e., from corresponding initial features signals). Those secondary features signals are processed in the same way as the initial features signals were processed in the feature extraction layer as described herein. An important example for a meaningful secondary feature signal is the "beat-by-beat" Heart Rate (HR) signal, or tachogram, which is very hard to analyze directly from the raw ECG signal from which it was derived. Another important example for secondary feature is the Heart Rate complexity, which is even harder to observe directly from the source ECG signal. The temporal, chaotic, linear, nonlinear and spectral behavior of the HR signal contains information of major importance to pathological prediction purposes. HR signal is generated by identifying "R-to-R" intervals in the original ECG signal, in the way described herein.

Other examples for new features signals that are derived from initial features signals, besides the HR feature signal, are:

Hypnogram;

Respiratory Rate complexity;

Low EMG Energy.

The combination of initial, secondary (i.e., new), and optionally external features, are fed to APS (FIG. 1, reference numeral 15), for predicting the next physiological/pathological state relating to a monitored person. An important tool that is utilized in the prediction process is the HMM method.

Adaptive Prediction of Time Series using a Mixture of HMM

Introduction

Learning-based modeling approaches such as Artificial Neural Networks (ANNs) and Hidden Markov Models (HMMs) have been found promising for medical diagnosis and prediction. These two approaches use a clinical database to construct generalized models or individualized models for each patient. HMM is a finite model that describes a probability distribution over an infinite number of possible sequences. The HMM model involves utilization of a given number of states, each of which might correspond to a different biomedical state. Each state "emits" observations according to observation-emission probability mechanism, and states are interconnected by corresponding "state-transition" probabilities. Starting from a given initial state, a sequence of states may be generated by moving from one state to another state, according to the state transition probabilities, until an end state is reached. Each state, then, emits observations according to that state's emission probability distribution, and a corresponding observable sequence of observations is formed from the collection of observations.

Basic Hidden Markov Models (HMMs)

A HMM is a double stochastic process with one underlying process (i.e. the sequence of states) that is not observable but may be estimated through a set of processes that produce a sequence of observations. HMMs are helpful in treating problems where information is uncertain and/or incomplete. The utilization of HMMs necessitates two stages: (1) a training stage, where the stochastic process is estimated through extensive observation, and (2) an application stage where the model may be used in real time to obtain sequences of maximum probability.

Two main algorithms are utilized for the training stage: the Baum-Welch algorithm, which is an Expectation Maximization (EM) based algorithm, which is utilized for Maximum Likelihood Estimation (MLE). Due to the non-convexity of the likelihood function, methods, such as simulated annealing, are now used. A new method for updating parameters of a model on real-time is disclosed in the present invention. The use of the trained HMM in real-time requires the use of an efficient algorithm which provides the state sequence of maximum probability. The Viterbi algorithm, which is a polynomial time dynamic programming algorithm, fulfills this need.

A Hidden Markov Model is defined by the triplet $\lambda=(\Pi, A, B)$ $\Pi$, $A$ and $B$ are initial state distribution vector, matrix of state transition probabilities and matrix of observation probability distribution, respectively.

$$A=[a_{ij}], a_{ij}=P(q_{t+1}=j|q_t=i)$$

$$B=[b_j(O_t)]$$

$$b_j(O_t)=P(O_t|q_t=j)$$

$$\Pi=[\pi_1, \pi_2, \ldots, \pi_N]$$

$$\pi_i=P(q_0=i)$$

$$i,j \in \{1,2,\ldots,N\}$$

$$t \in \{1,2,\ldots,T\}$$

In general, at each given time 't', the model is in one of the states $q_i$. The model outputs $O_t$ with probability $b_j(O_t)$ and, then, "jumps" to state $q_j$ with probability $a_{ij}$.

The Prediction System

The prediction system comprises a mixture of "experts", where each "expert" is an ergodic HMM with several states that can be partitioned into as many as required states groups.

Figure 4:
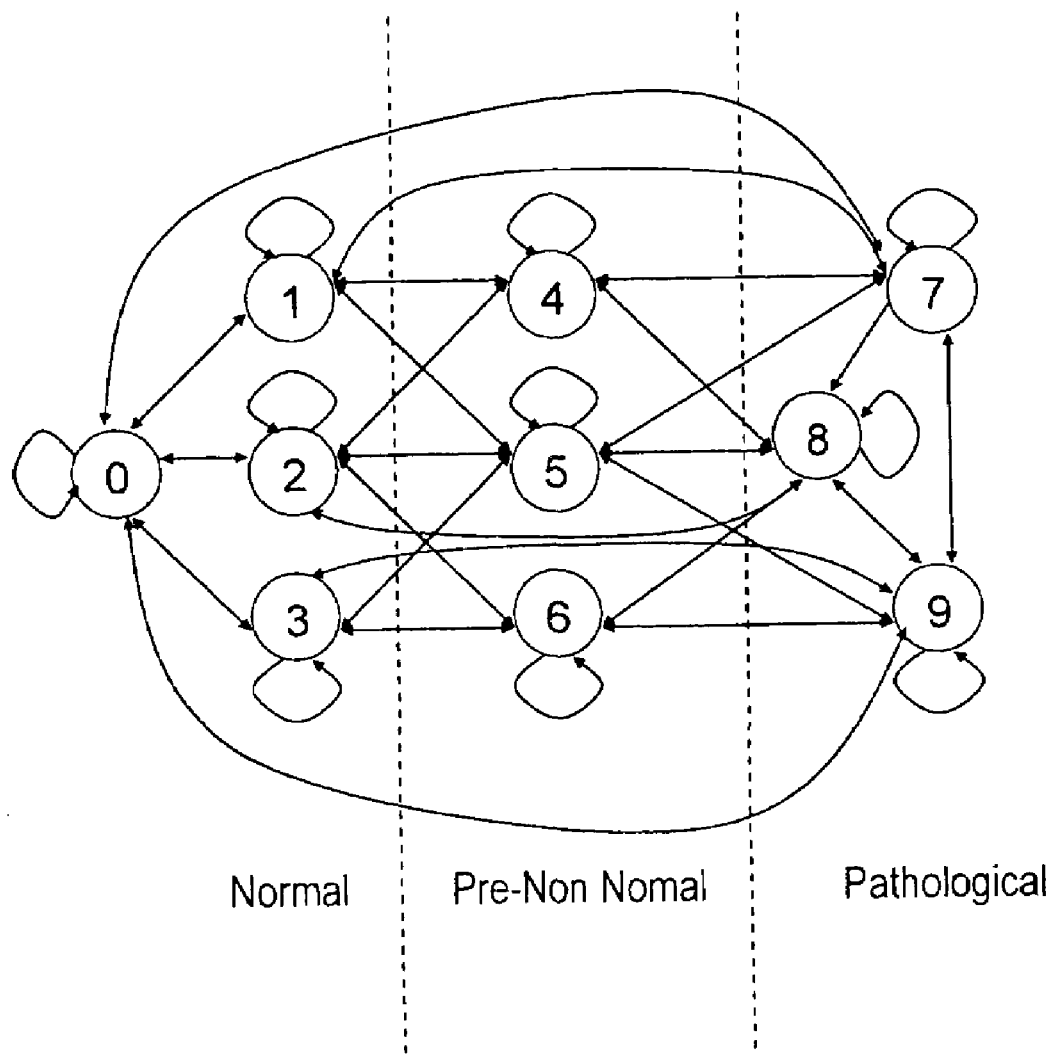
FIG. 4 schematically illustrates variousphysiological/pathological conditions that are grouped into "Normal", "Pre-non normal" and "Pathological" states, according to an embodiment of the present invention.

FIG. 4, schematically illustrates exemplary three groups HMM model; i.e., (1) states group 1, which stands for Normal Activity; (2) states group 2, which stands for Pre Non-Normal activity (prediction state or alarming state), and (3) state group 3, which stands for Non-Normal Activity (e.g., heart attack, epilepsy, etc.). Each ergodic HMM is referred to as an "expert", due to its capability to predict transfer from one state (e.g., state-2) to another state (e.g., state-4). Of particular importance is the capability of the HMM model to identify states in group 2 (i.e., the "Pre Non-normal" group), and to calculate the probability of transferring from a given state in group 2 (e.g., state-6) to states 8 or 9 in group 3 (i.e., the "Non-normal activity"), to state 3 (i.e., non-normal activity, or pathological state/event), in particular, which is the purpose of the present invention.

The prediction output of the HMM mixture may be either supported, or contradicted, by taking into account external factors, such as overall physiological/pathological state of the monitored person, and anchor fuzzy decision rule base. For example, the prediction may be enhanced by referring to the visual appearance of special/pre-selected events, such as spikes in epilepsy prediction or pathological type of a heartbeat in arrhythmia prediction. Likewise, checking the sleep stage will allow the system to reinforce a prediction's decision, or weaken it. By this way, system diversion is prevented.

Estimating the dynamics of state transition will determine the treatment type. For example, passing from one of the normal states to one of the pre non-normal states will activate preventive pacing (e.g., the system will determine the electrical shock level in a defibrillator). It should be noted that each state in the offered model might be characterized (i.e., be pre-determined) by a different set of features. That is, for a given state, a set of features is utilized, which optimally characterize, or represent, the given state. The reason why several experts are used originates from the fact that state characteristics differ from one population group to another, and from one overall physiological/pathological state to another. For example, a non-normal state in a certain population group or physiological/pathological state might be considered a normal state in another population group. Therefore, each expert represents, in fact, a different global behavior of the modeled time series, given a specific patient.

Several HMM models may be operable simultaneously, with respect to a monitored person, while, at a given time or stage, only one HMM model, which is found optimal, will be utilized in the final prediction process. According to another example, when monitoring sleeping stages, a different HMM model may be utilized with respect to a different sleeping stage, which is optimal to the corresponding sleeping stage. The system may automatically choose the corresponding HMM models along the monitoring period and find the optimal HMM model(s) at a given time or stage.

Another element of the offered system is the ability to predict the future states sequence using the derived temporal membership relating to each one of the states.

Adaptive Prediction is Obtained by Performing:
- training "N" HMM models using Baum Welch algorithm or simulated annealing based algorithms using global medical knowledge;
- adaptively segmenting time series, for extracting (initial) features from chosen identified segments, and generating new signals there from;
- extracting new (secondary) features from the new signals;
- For each one of the "N" HMM models, estimating the states sequence for a predetermined period of time.
- For each one of the "N" HMM models, calculating the likelihood of the data given the model; i.e., estimating whether a specific HMM model is suitable for the data which it processes;
- Choosing the model that outputs maximum likelihood value;
- If the likelihood value is lower than a predetermined threshold (meaning that none of the models fits the data), re-train the selected model according to patient specific data and external fuzzy rule base;
- If the likelihood value is higher than a predetermined threshold, update the selected model parameters using current data. The updating procedure is performed on-line by updating the probability density functions that are related to each state.

The above eight steps for adaptive prediction are described in details immediately below.

Figure 5:
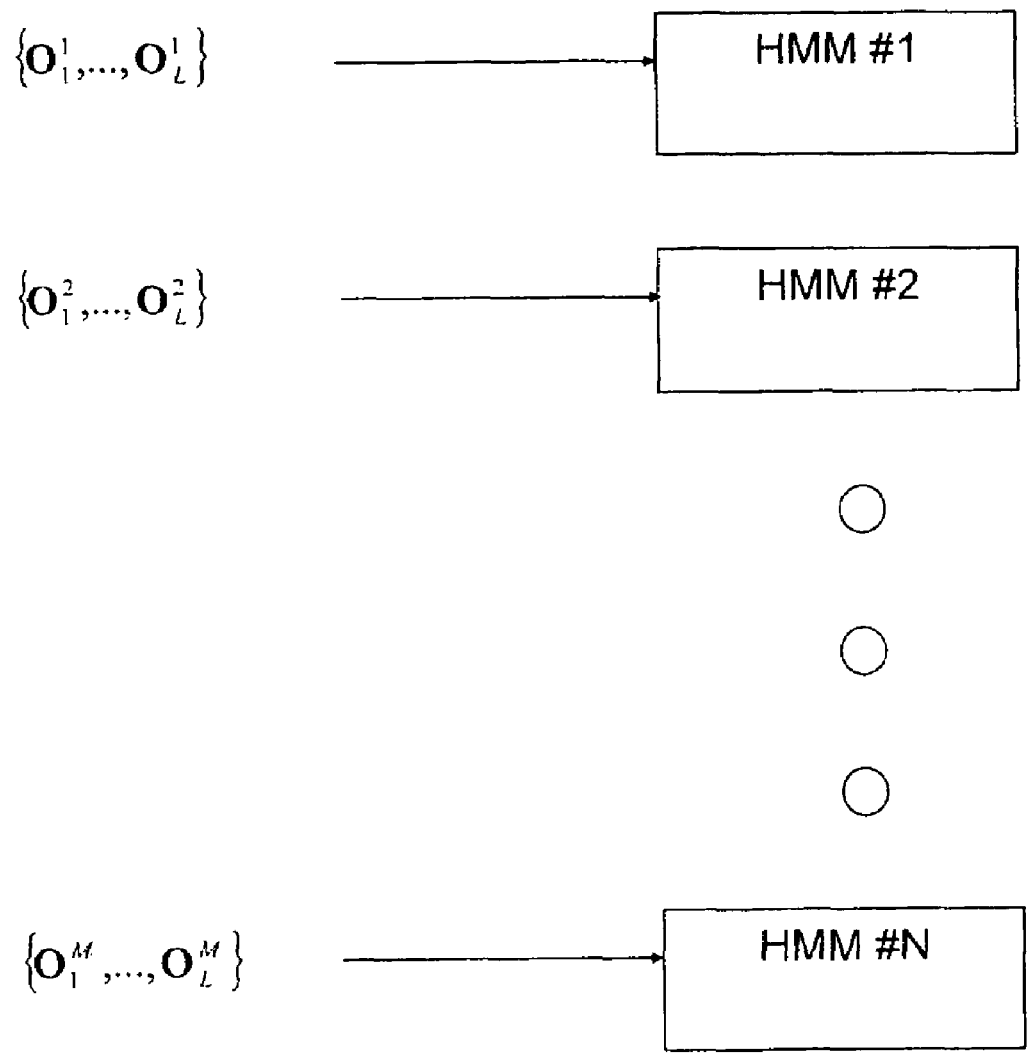
FIG. 5 schematically illustrates a general layout and functionality of the HMM-based "expert system", according to a preferred embodiment of the present invention.

1. Models Construction and Training Phase:

In this step, a set of N HMM models is constructed (see FIG. 5), where each HMM model corresponds to a different process (e.g., ECG). For each model, a set of L different observation sequences are used to automatically estimate the optimal parameters of each HMM. Each HMM model is automatically trained. The training stage of HMM model involves estimation of current parameters of the HMM model and, whenever required, assignment of new, or updated, parameters that best suit the HMM model at a given stage.

In general, there are two main algorithms for training HMM model(s):

(1) The Baum-Welch algorithm, which is an EM based algorithm for MLE (a reference may be made to L. R. Rabiner, B. H. Juang, "Fundamentals of speech recognition", Prentice Hall signal processing Series, 1993).

(2) Simulated annealing, which is used for overcoming problems that are related to the non-convexity of the likelihood function (a reference may be made to "Discriminative Training of Tied-Mixture of HMM by Deterministic annealing", by Liang Gujarat Nayak and Kenneth Rose).

In order to achieve optimal training, it is essential to initiate the training algorithms with optimal initial conditions (i.e., by un-supervised fuzzy clustering). It is essentially important to initiate correctly the parameters of the probability distribution that characterizes each stage. This distribution is modeled as a mixture of Gaussians:

$$b_j(o; \lambda^m) = \sum_{k=1}^{K} c_k N(o, \mu_k, U_k)$$

where j is a state index, o is an observation vector, $\lambda^m$ is the model index, $c_k$ are the mixing proportion of component k, $\mu_k$ is the means vector of component k and $U_k$ is the covariance matrix of component k.

Thus, sophisticated learning algorithms, such as unsupervised fuzzy clustering for density estimation, are utilized for this task. For each state, related training observations are collected from a global medical database. Density estimation algorithms are used in order to estimate the density of those observations.

After training each model, the following steps are performed, which describe the on-line operation of the prediction system, with respect to a specific patient.

2. Adaptive Segmentation:

The measured signals are adaptively segmented using a corresponding adaptive segmentation algorithm described herein.

3. Feature Extraction:

In order to generate observations for the HMM models, features are extracted from each segment to form the observation sequence $\{o_t\}_1^T$.

4. Estimation of States Sequence:

For the states sequence estimation stage, the forward probability function, which evaluates the probability of a partial sequence at node i, which "node" means one of N states, given a specific HMM model, is utilized:

$$a_t(i) = P(o_1, o_2, \ldots, o_T, q_t = i | \lambda^m)$$

i.e. $a_t(i)$ is the probability of being in state i at time t, given the HMM model $\lambda^m$. This probability can be computed recursively and it is suitable for a real time application. The temporal membership of each state 'i' is obtained by normalizing $a_t(i)$ by $$\sum_{i=1}^{N} \alpha_t(i).$$

The state sequence $\{q_t\}_1^T$ will be derived by $$q_t = \underset{i}{\mathrm{ArgMax}} \left\{ \frac{\alpha_t(i)}{\sum_{i=1}^{N} \alpha_t(i)} \right\}$$

The above-described procedure will be initially employed on each one of the 'N' HMM models.

5. Calculating the likelihood of the Data Per Given HMM Model:

For each HMM model, the likelihood of the data is calculated as follows:

$$P(O | \lambda^m) = \sum_{i=1}^{N} \alpha_T(i).$$

6. Choosing the HMM model that Yields the Highest Likelihood Value:

The chosen HMM model meets the condition:

$$\lambda_{opt} = \underset{m}{\mathrm{ArgMax}} \{P(O | \lambda^m)\}.$$

7. Re-training:

According to step 7, the chosen HMM model(s) has/have the highest likelihood value (i.e., $P(O|\lambda^{opt})$), and if the latter likelihood value is higher than a predetermined reference likelihood value, the chosen HMM model(s) is considered optimal. However, if the likelihood value $P(O|\lambda^{opt})$ is smaller than the predetermined reference likelihood value (meaning that none of the HMM models fits the data), the chosen HMM model is re-trained in accordance with patient specific data and external fuzzy rule base.

8. State Recognition and Model Updating:

If the likelihood value $P(O|\lambda^{opt})$ of the chosen HMM model(s) is bigger than the predetermined likelihood value, the parameters of the chosen HMM model are updated using current data (refer to "ON-LINE ADAPTIVE LEARNING OF THE CORRELATED CONTINUOUS DENSITY HIDDEN MARKOV MODELS FOR SPEECH RECOGNITION", by Qiang Huo and Chin-Hui Lee).

The procedure, for updating parameters of the chosen HMM model, is performed automatically and on-line, by updating the probability density functions of each state using discriminative methods. The state sequence $\{q_t\}_1^T$ will is derived by $$q_t = \underset{i}{\text{ArgMax}} \left\{ \frac{\alpha_t(i)}{\sum_{i=1}^{N} \alpha_t(i)} \right\}.$$

The prediction system will issue an alarm whenever it yields states that represent pre-pathological behavior or state transition dynamics which represents pre-pathological behavior (for example it is possible that the estimated states could represent normal behavior, but the state transition dynamics can indicate an expected pathological behavior).

The described generic prediction method may be used for prediction of essentially any physiological/pathological phenomena or pathology. For example, the prediction principles could be utilized to predict:

CHF (congestive heart failure);
Arrhythmias (e.g.,VT and SVT);
Sleep apnea;
Atrial and ventricular fibrillation;
Epilepsy prediction;
Sleep stages;
Epilepsy.

Two detailed examples are described herein below, which refer to two well known pathologies; i.e., arrhythmia and epilepsy. The examples demonstrate employment of the prediction principles with respect to these pathologies.

EXAMPLE 1

Arrhythmia Prediction Using ECG Signal

Figure 11:
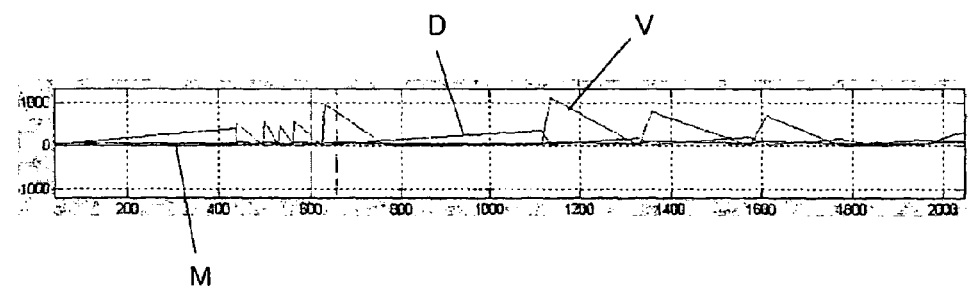
FIG. 11 depicts extraction of Mean, Variance and Duration from the exemplary heart rate (HR) signal shown in FIG. 10.
Figure 12:
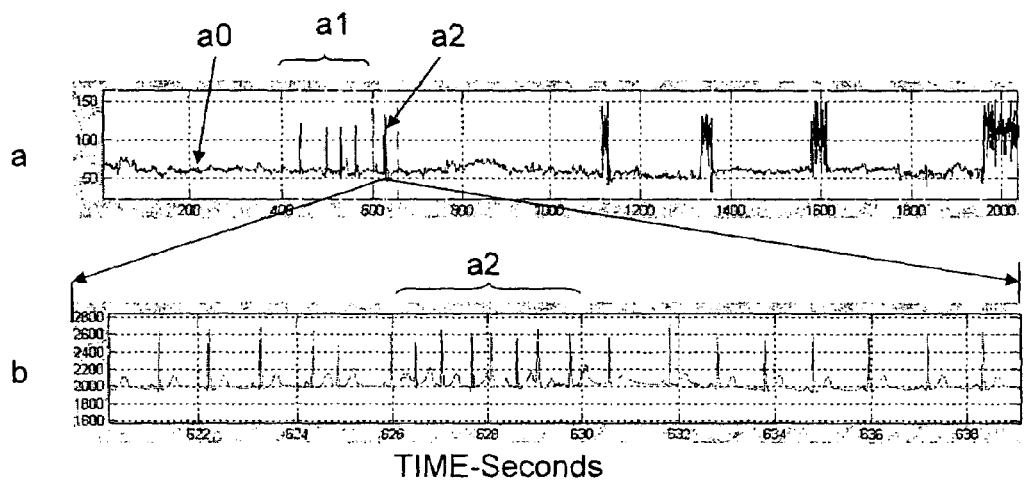
FIG. 12 depicts identification of a first pathological event (i.e., SVT) in the exemplary heart rate (HR) signal shown in FIG. 10.
Figure 47:
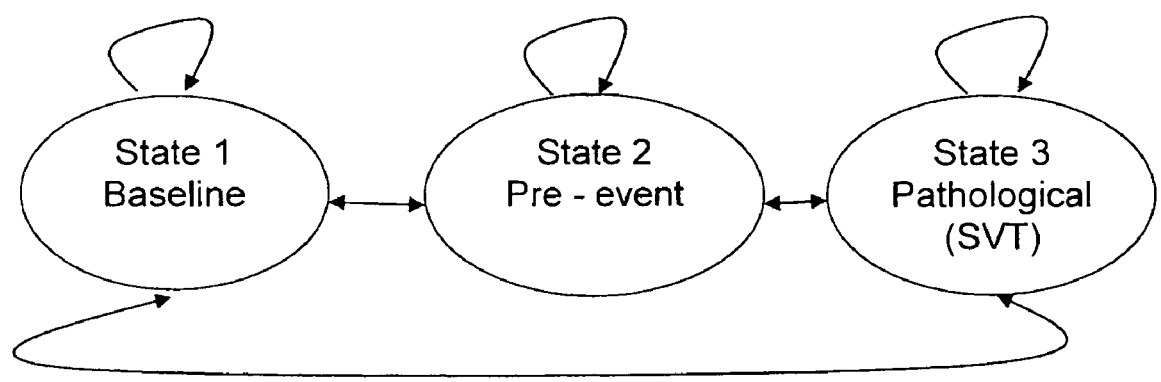
FIG. 47 depicts exemplary 3-state HMM model in connection with FIGS. 6 to 12.

According to this example, the input is an ECG tracing signal and the output is an arrhythmia (in this example, SVT—Supraventricular Tachycardia) prediction. The following notions are to be made with respect to this example:

1. By use of adaptive segmentation, the ECG signal is divided into separate heartbeats by detecting the corresponding R-waves, as described with respect to the ECG algorithm); the patient-specific adaptation algorithm learns the normal heartbeat morphology, thus, clustering the different heartbeat morphologies while taking into consideration noise cancellation through environmental analysis. By selecting the R-waves of all determined true beats, a (new) HR signal is extracted from the time series representing the ECG signal.
2. An adaptive GLRT based segmentation algorithm is employed on the HR signal, dividing it into quasi-stationary segments (FIG. 10a). It can be seen that the segmentation mainly delineates transient tachycardic periods (see for example segments a1, a2, a3 and a4 in FIG. 10a, which are identifiable by corresponding vertical lines).
3. From each segment in the HR signal, the mean (M), variance (V) and duration (D) features are extracted (see FIG. 11).
4. Each segment is then compared to the source ECG segment to verify that its derived features are indeed-physiological/pathological and not influenced by noise or artifacts (FIG. 12). If the features truly describe a physiological/pathological state and not an artificial one, then,
5. An observation vector is build from the extracted features, and
6. The observation vector is processed in a '3-state' HMM model (FIG. 47). The terminology "observation vector" refers to a vector, the elements of which are initial or secondary features. The HMM model classifies each observation vector to a corresponding physiological/pathological state, which may represent normal, pre-pathological or pathological condition.

The classification output, as resulted from the utilization of the HMM model, can be seen in FIG. 12 (i.e., HR graph). FIG. 12 depicts a graph, in which the original segments were painted, by the prediction system, by different colors, in order to distinguish between the three states; i.e., the normal state was originally painted in red, the pre-pathological in blue and the pathological states in bolded black. The original red colored segments are indicated in FIG. 12 by a0, the blue colored segments are indicated in FIG. 12 by a1 and the bolded black color are indicated in FIG. 12 by a2 to a6.

Figure 10:
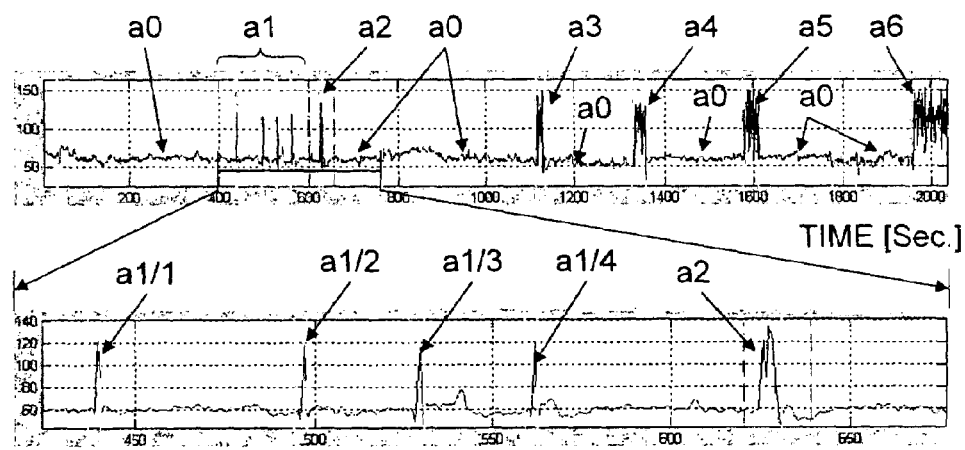
FIG. 10 depicts adaptive segmentation of exemplary heart rate (HR) signal, according to a preferred embodiment of the present invention.

Referring to FIGS. 10 and 12, it should be noted that due to the short periods of segments a1/1 to a1/4, these segments are not medically classified as SVT, but, rather, they can assist in predicting SVTs. Therefore, it can be seen in FIG. 12 (and even better seen in FIG. 10), that approximately 200 second before the occurrence of the SVT arrhythmia (i.e., segment a2 in FIGS. 10a and 10b), the system detected segment a1/1, which was automatically classified by the prediction system, as state-2, and, therefore, as an indicative for the SVT arrhythmia. Accordingly, a corresponding alarm could be initiated by the prediction system.

EXAMPLE 2

Epilepsy Prediction Using EEG and ECG Signals

The inputs to the prediction system are the EEG and ECG signals, and the output is epilepsy prediction.

1. The EEG signal is adaptively segmented into quasi-stationary segments using the GLRT-based adaptive segmentation algorithm.
2. The following features are extracted from each EEG segment:
Variance.
Fractal dimension.
Synchrony measure.
3. Temporal transient morphology features (pattern recognition) (using matching pursuit algorithm).

Figure 6:
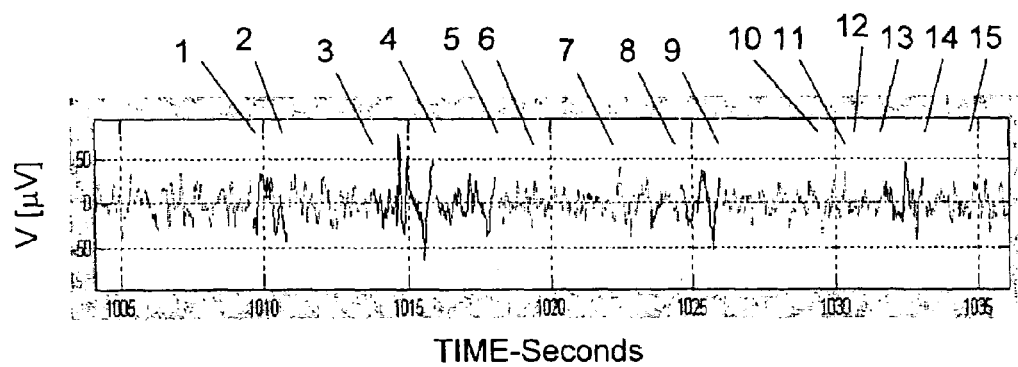
FIG. 6 depicts adaptive segmentation of exemplary EEG signal, including detection of spikes that are contained therein, according to a preferred embodiment of the present invention.

Based on temporal environmental behavior (energy, frequency, etc.) and morphology features, a spike-detection algorithm is implemented. FIG. 6 depicts the EEG segments boundaries and detected spikes in a 30-seconds 'stretch' of the recorded trace.

Referring to FIG. 6, it shows the EEG segments that were identified by using adaptive segmentation process in the way described herein. The boundaries of the identified segments are indicated by reference numerals 1 to 15. In addition, some of the identified segments include spikes. The prediction system identified the spikes as segments of particular interest, and, therefore, in order to distinguish them from the surrounding segments, the system automatically shows the spikes in black color (i.e., other segments are shown in grey color).

Figure 7:
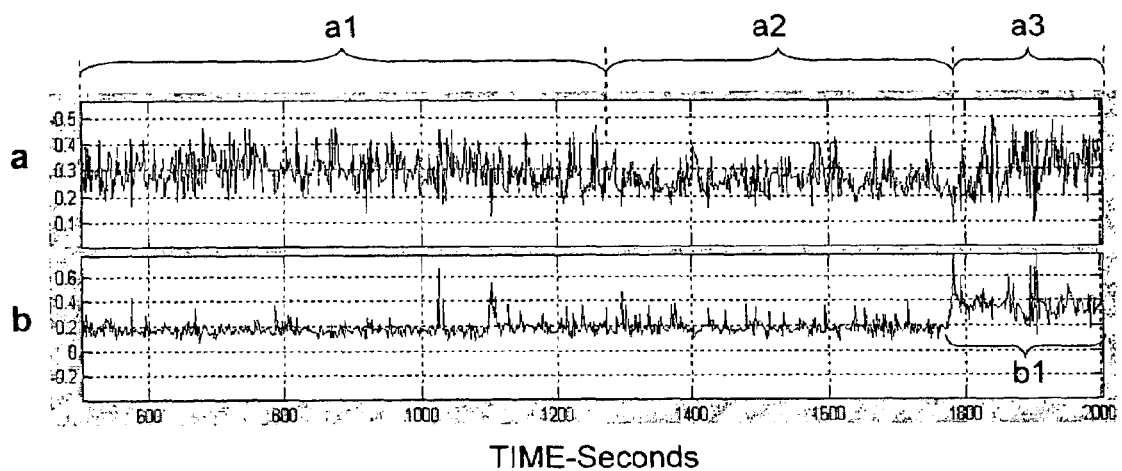
FIGS. 7a and 7b depicts the synchrony measure and fractal dimension, respectively, of the EEG signal shown in FIG. 6, according to a preferred embodiment of the present invention.

FIGS. 7a and 7b depicts the behavior of the synchrony measure and fractal dimension features, respectively (i.e., two of the extracted features) as a function of time. Main sections a1, a2 and a3 (shown in FIG. 7a) are indicative of normal, pre-pathological and pathological states, respectively, of a monitored person. Likewise, b1 (shown in FIG. 7b) conspicuously shows the epileptic seizure.

The epileptic seizure bursts at approximately 1,770 seconds and it can be seen that from this time on, both fractal dimension and synchrony increases. Comparing the synchrony period between 0 seconds and 1300 seconds to the synchrony period between 1,300 seconds to 1,770 seconds, it can be seen that the synchrony decreases about 8 minutes before the seizure. Detection of this phenomenon can be used as a prediction indicator.

4. By use of adaptive segmentation, the ECG signal is divided into separate heartbeats by detecting the R-waves; the patient-specific adaptation algorithm learns the normal heartbeat morphology, thus, clustering the different heartbeat morphologies while taking into consideration noise cancellation through environmental analysis. By selecting the R-waves of all determined true beats, a (new) HR signal is extracted from the ECG.

Figure 8:
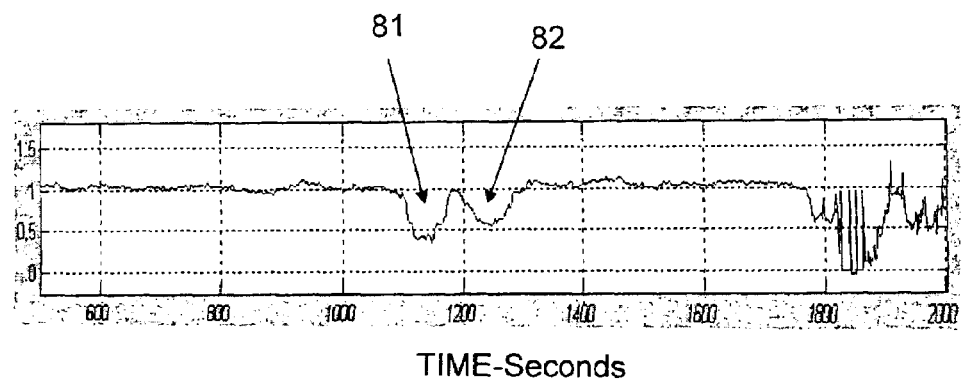
FIG. 8 depicts the fractal dimension of an exemplary heart rate signal, according to a preferred embodiment of the present invention.

5. The HR signal is adaptively segmented using the GLRT based adaptive segmentation algorithm, and the fractal dimension of each segment is calculated. FIG. 8 depicts the behavior of the HR fractal dimension as a function of time.

Referring to FIG. 8, it can be seen that the seizure is associated with a distinct reduction in the fractal dimension (reference numerals 81 and 82) and that the milder drops at approximately 1,100 and 1,300 seconds, which correspond to transient tachycardia, can also be utilized as a prediction indicator.

6. The heart rate fractal dimension and the EEG synchrony and fractal dimension measures are synchronized in time in order to get a common time base (i.e., in a process known in the art as "feature fusion").

7. A 3-state ergodic HMM model utilizes the fused features in order to estimate the state series. Stage 1 stands for baseline state, stage 2 stands for pre-seizure state i.e. prediction and state 3 stands for the pathological state—epileptic seizure.

Figure 9:
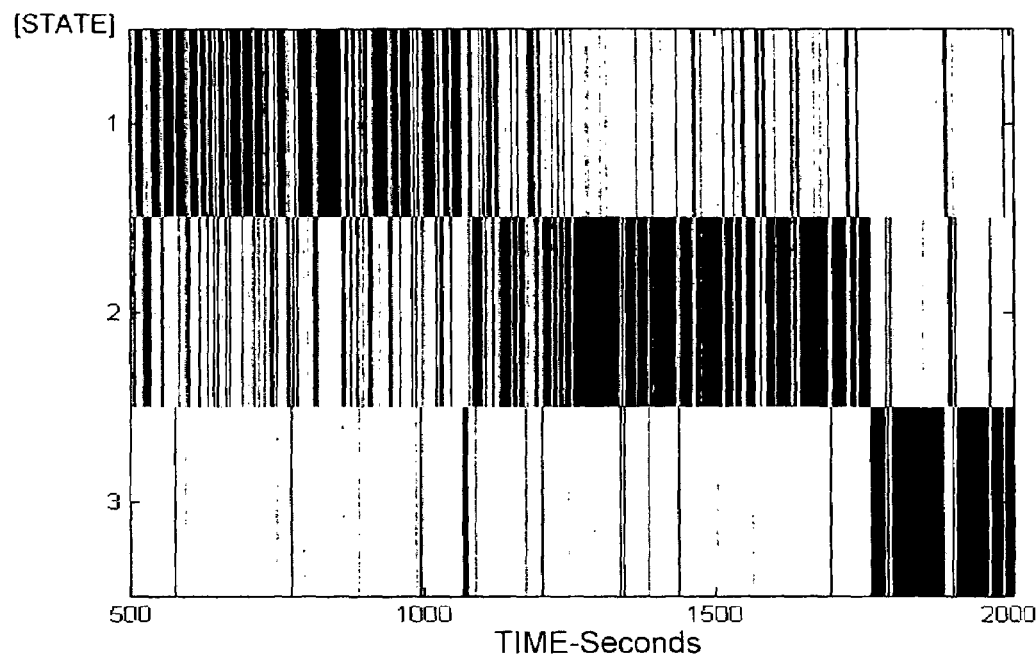
FIG. 9 depicts the membership function of each one of the states shown in FIG. 47.

Referring to FIG. 9, it can be seen that approximately 12 minutes before the seizure, the membership in state 2, which is the prediction state, is higher than the memberships in states 1 and 3. The membership value in state 2, together with spike appearance, are combined in order to decide whether an epileptic seizure is likely to burst.

Adaptive Segmentation Algorithm of Multidimensional Time Series

The task of the adaptive segmentation algorithm is distinguishing between consecutive, or adjacent, different quasi-stationary segments contained within a multidimensional time series. For that purpose, the algorithm may utilize the General Likelihood Ratio (GLR) or the Kullback-Leibler distance measures.

1. Description of the GLR Distance Measure

Figure 13:
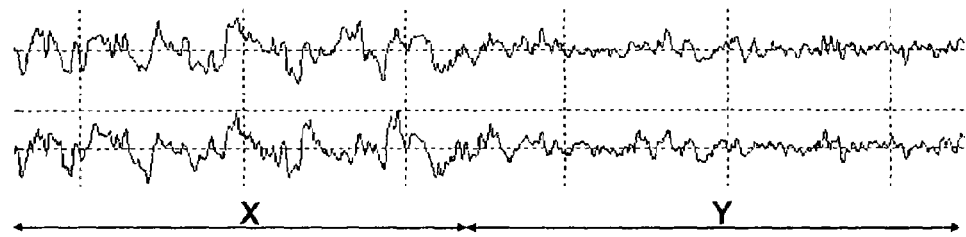
FIG. 13 depicts two consecutive quasi-stationary 2-dimensional time series that were obtained from an exemplary EEG signal.

Given two time series, it is desirable, from the present invention's point of view, to know whether they have similar statistical properties, and thereby, to determine whether they belong to the same stationary process. The samples of the first series are marked as $\{x_n\}_1^N$ and the samples of the consecutive series is marked as $\{y_n\}_1^M$, as shown in FIG. 13.

Now, two hypothesis will be made and tested for their validity. According to the first hypothesis, $H_1$ represents the assumption that the two series were generated by different processes and $H_0$ represents the assumption that the two series were generated by the same process.

$$H_1 : x_n \sim N(\mu_x, C_x) \text{ i.i.d} \tag{1.1}$$

$$y_n \sim N(\mu_y, C_y) \text{ i.i.d}$$

$$H_0 : x_n \sim N(\mu_c, C_c) \text{ i.i.d} \tag{1.2}$$

$$y_n \sim N(\mu_c, C_c) \text{ i.i.d}$$

The likelihood of $\{x_n\}_1^N$ given $H_1$ is:

$$f(X; H_1) = \prod_{n=1}^{N} f(x_n; H_1) \tag{1.3}$$

$$= (2\pi)^{-\frac{Nd}{2}} |C_x|^{\frac{1}{2}} \exp\left(-0.5 \sum_{n=1}^{N} (x_n - \mu_x)^T C_x^{-1} (x_n - \mu_x)\right)$$

Given that $C_x$ is diagonal:

$$f(X; H_1) = \tag{1.4}$$

$$(2\pi)^{-\frac{Nd}{2}} \left(\prod_{k=1}^{d} \sigma_{k,x}^2\right)^{-\frac{N}{2}} \exp\left(-0.5 \sum_{k=1}^{d} \sigma_{k,x}^{-2} \sum_{n=1}^{N} (x_{k,n} - \mu_{k,n})^2\right)$$

$$\Rightarrow f(X; H_1) = (2\pi)^{-\frac{Nd}{2}} \left(\prod_{k=1}^{d} \sigma_{k,x}^2\right)^{-\frac{N}{2}} \exp(-0.5 N \sigma_{k,x}^{-2} \hat{\sigma}_{k,x}^2) \tag{1.5}$$

The maximum likelihood of $\{x_n\}_1^N$ given $H_1$ is achieved when $\sigma_{k,x} = \hat{\sigma}_{k,x}$.

Therefore:

$$ML(X; H_1) = (2\pi)^{-\frac{Nd}{2}} \left(\prod_{k=1}^{d} \hat{\sigma}_{k,x}^2\right)^{-\frac{N}{2}} \exp(-0.5N) \tag{1.6}$$

In the same manner:

$$ML(X; H_1) = (2\pi)^{-\frac{Md}{2}} \left(\prod_{k=1}^{d} \hat{\sigma}_{k,y}^2\right)^{-\frac{M}{2}} \exp(-0.5M) \tag{1.7}$$

And $$ML([X, Y]; H_0) = (2\pi)^{-\frac{(M+N)d}{2}} \left(\prod_{k=1}^{d} \hat{\sigma}_{k,c}^2\right)^{-\frac{(M+N)}{2}} \exp(-0.5(M+N)) \tag{1.8}$$

Where $\hat{\sigma}_{k,c}^2 = \dfrac{N \hat{\sigma}_{k,x}^2 + M \hat{\sigma}_{k,y}^2}{M + N}$ Thus the generalized likelihood ratio test (GLRT) is given by:

$$z = \frac{ML([X, Y]; H_1)}{ML([X, Y]; H_0)} = \tag{1.9}$$

$$\frac{ML(X; H_1) \cdot ML(X; H_0)}{ML([X, Y]; H_0)} = \frac{\left(\prod_{k=1}^{d} \hat{\sigma}_{k,x}^2\right)^{-\frac{N}{2}} \left(\prod_{k=1}^{d} \hat{\sigma}_{k,y}^2\right)^{-\frac{M}{2}}}{\left(\prod_{k=1}^{d} \hat{\sigma}_{k,c}^2\right)^{-\frac{(M+N)}{2}}}$$

In order to transform this ratio into a distance we shall take the natural logarithm of z and obtain:

$$d = 2\log(z) = \sum_{k=1}^{d} N\log(\hat{\sigma}_{k,x}^2) + M\log(\hat{\sigma}_{k,y}^2) - (M+N)\log(\hat{\sigma}_{k,c}^2) \quad (1.10)$$

In the generalized likelihood test the value of d is compared to a threshold value in order to decide whether the two series are similar in the statistical sense (referring to statistics of order 2).

2. Description of the Kullback-Leibler Distance Measure

In some cases, the samples of the two series under comparison are statistically dependent and not normally distributed. In such cases it is necessary to compare the morphology of their probability density functions. The probability density functions may be estimated using parametric, non-parametric or parametric-non-parametric methods. If $f_x(x)$ is the probability density function of $\{x_n\}_1^N$ and $f_y(y)$ is the probability density function of $\{y_m\}_1^M$ and $f_x$ and $f_y$ have the same supporter $\{z_l\}_1^{N+M-1}$, then the Kullback-Leibler distance is given as:

$$K(f_x \| f_y) = \sum_l f_x(z_l) \log\left[\frac{f_x(z_l)}{f_y(z_l)}\right] \quad (2.1)$$

Figure 14:
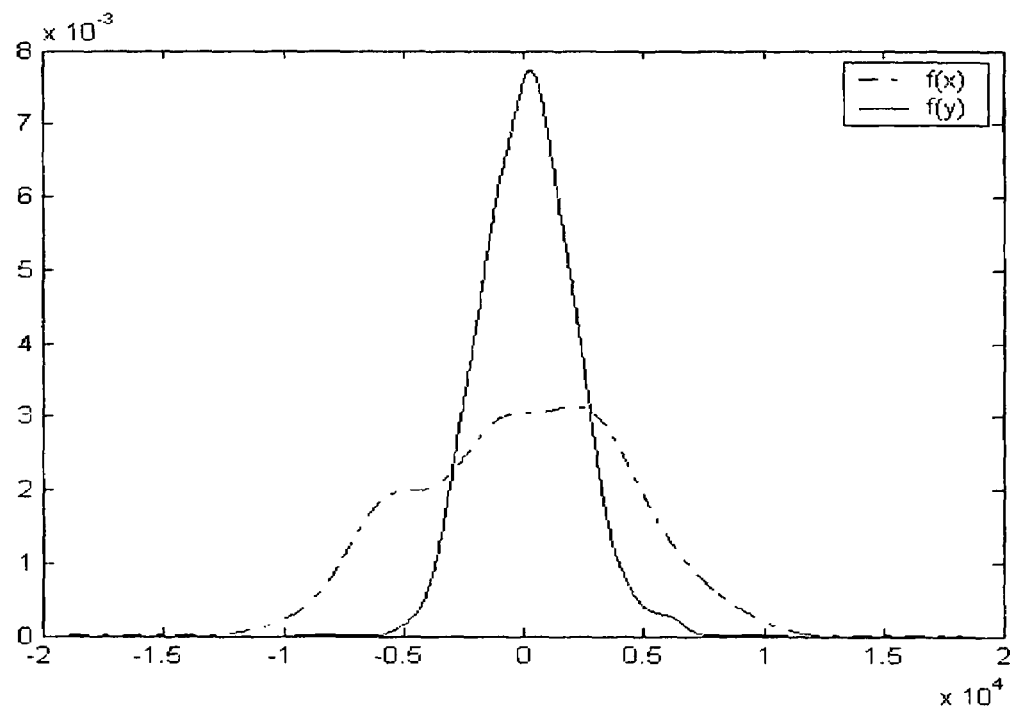
FIG. 14 depicts Non-parametric density estimation of compared time series, according to a preferred embodiment of the present invention.
Figure 15:
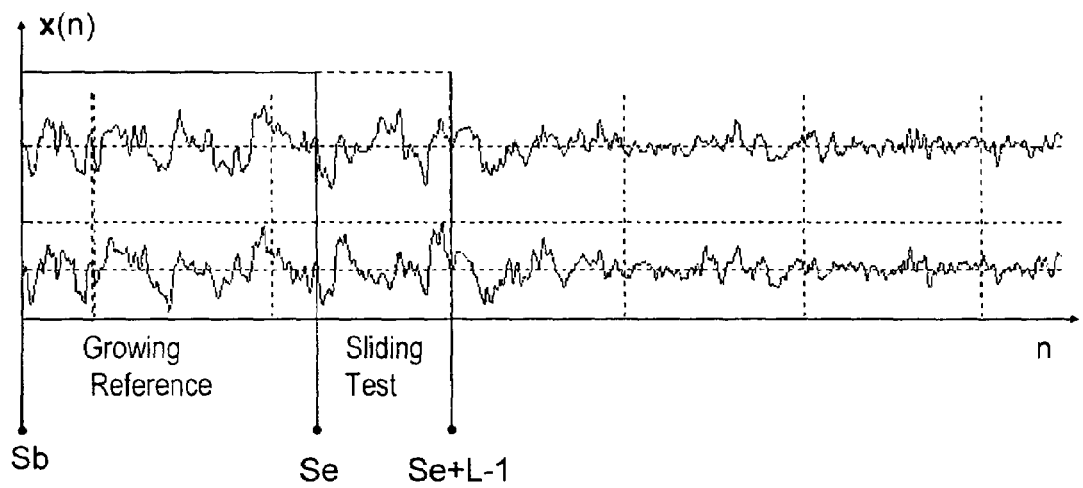
FIG. 15 illustrates adaptive segmentation in connection with EEG signal, according to a preferred embodiment of the present invention.

In the Kullback-Leibler (KL) test, the value of K is compared to a threshold value in order to decide whether the two series are similar in the statistical sense. FIG. 14 shows a non-parametric estimation of probability density functions related to two compared series.

3. Description of the Segmentation Algorithm

In the segmentation algorithm two consecutive widows are initially defined—a reference window and a sliding window. These windows are marked by R and S, respectively, in FIG. 13. The various segments are identified within the time series by sliding the window (S), and testing adjacent sections for their statistical characteristics. Whenever a difference is identified between two compared time series, a boundary is determined there between.

3.1 Detection of Segment Boundaries

The decision process for detecting a new boundary at an arbitrary point $S_b < n < S_e + L - 1$ ( $S_e$ is initially set to $S_b + L - 1$ ) is preformed by establishing a test window $S_e < n < S_e + L - 1$ and a reference window $S_b < n < S_e$ and applying a GLR or KL test to the sequences {R} and {S} defined by these windows (FIG. 14).

Figure 16:
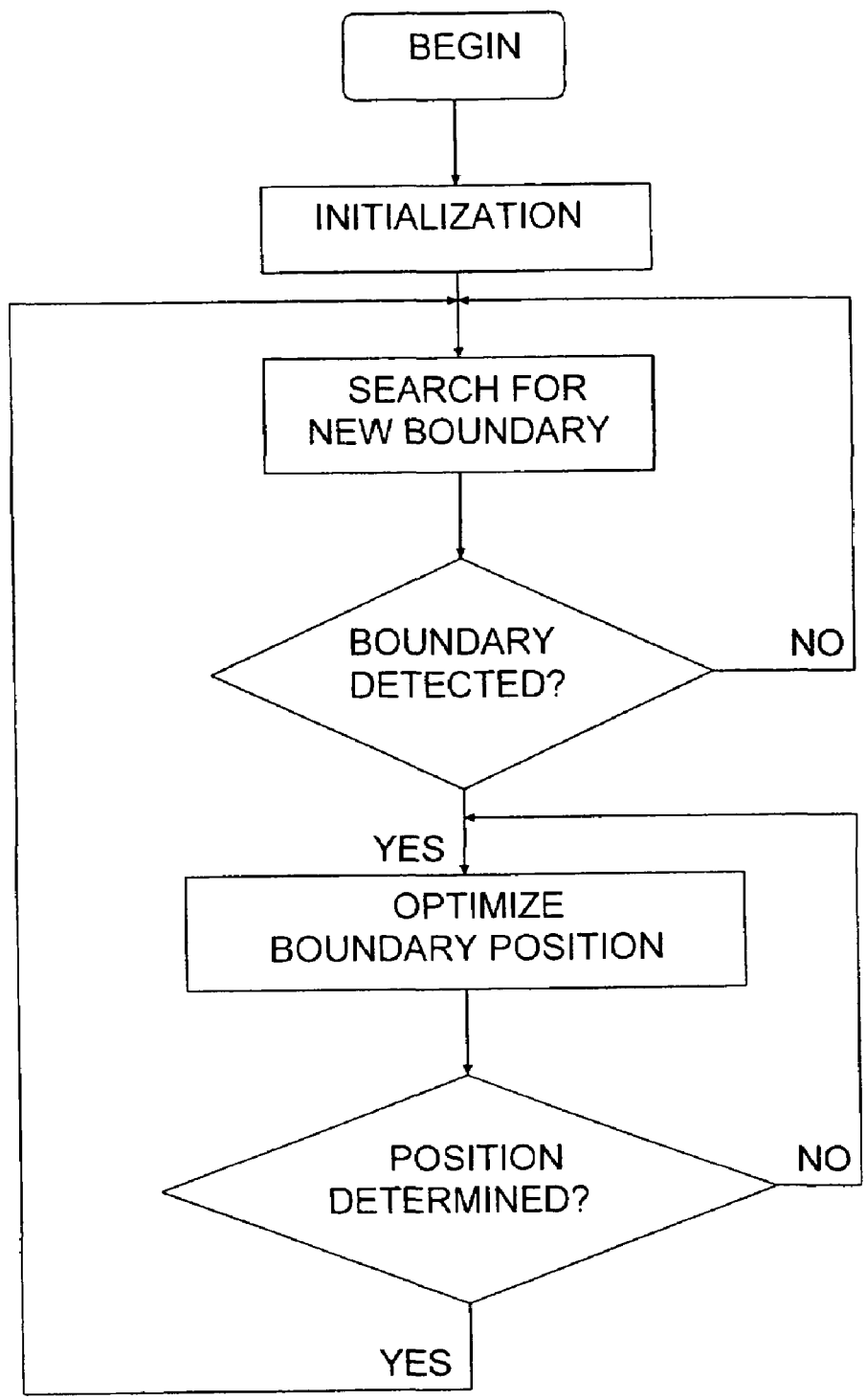
FIG. 16 schematically illustrates a general flow chart of the segmentation process mentioned in connection with FIG. 15.
Figure 17:
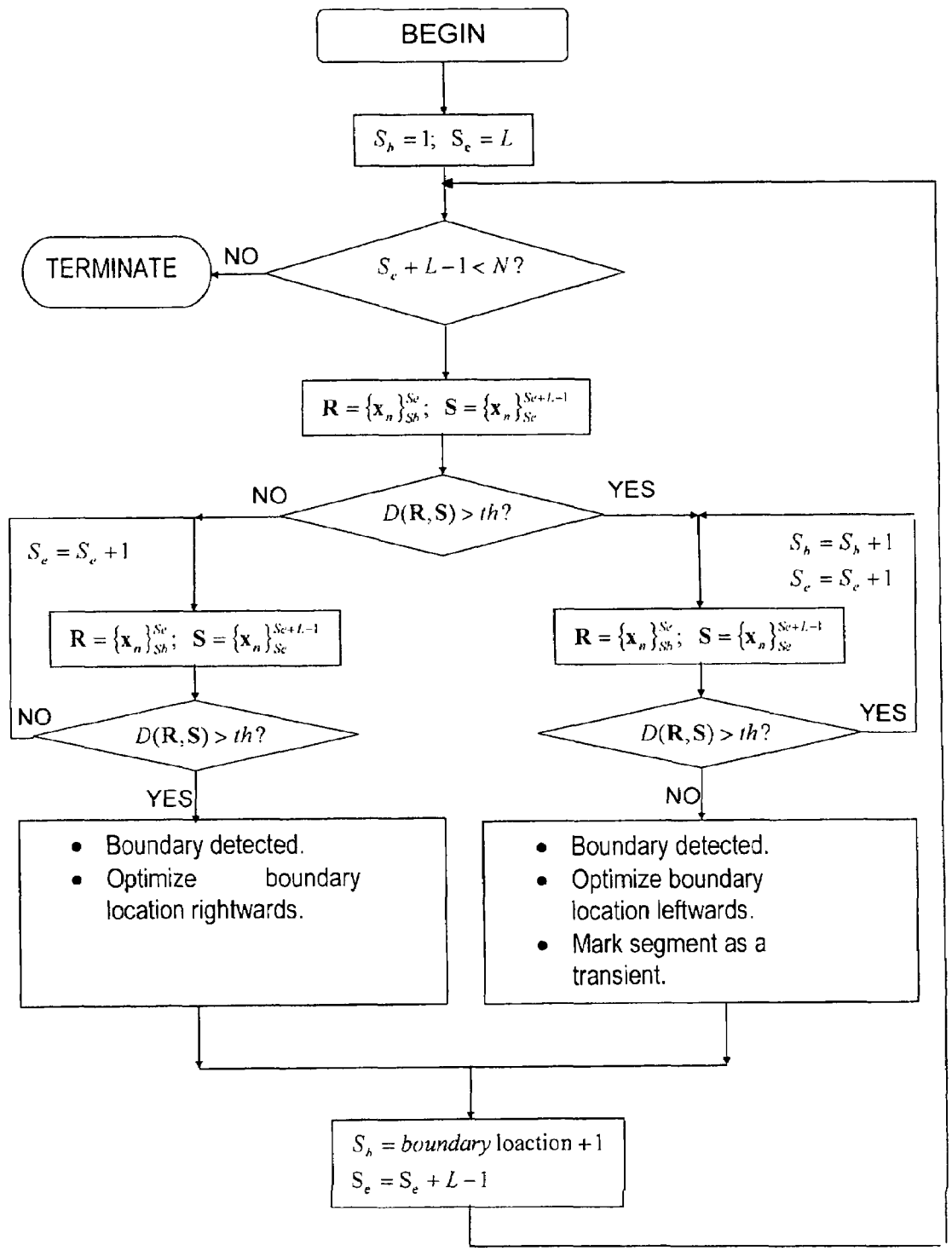
FIG. 17 schematically illustrates in more details the segmentation process mentioned in connection with FIG. 15.

If the distance initially exceeds a predetermined threshold value, then the windows will be shifted to the right, maintaining their initial same size, until the distance will be lower than the threshold value. At this step, the optimal boundary location is assumed to be in the interval $S_b < n < S_e$ and an optimization boundary detection algorithm is preformed. These type of segments will be marked as transients. If the distance initially does not exceed a predetermined threshold value, then the value of $S_e$ is incremented, causing the reference window to grow and the test window to slide, until the distance exceeds a threshold value. At this step the optimal boundary location is assumed to be in the interval $S_e < n < S_e + L - 1$ and an optimization boundary detection algorithm is preformed. FIGS. 16 and 17 are block diagrams of the algorithm.

3.2 Optimization of Boundary Position

Figure 18:
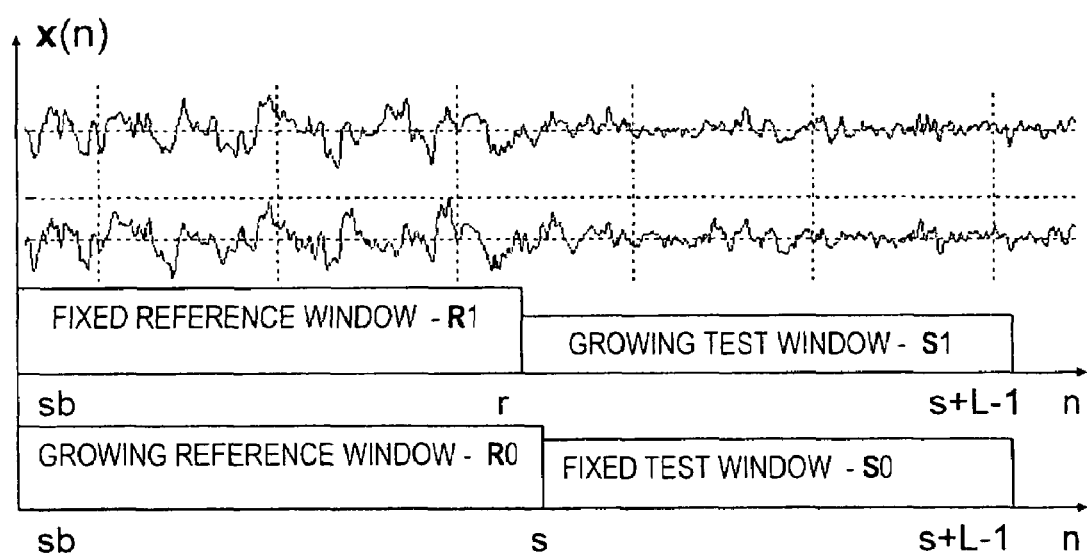
FIG. 18 schematically illustrates optimization of the segmentation shown in FIG. 15.

The optimization procedure preformed to find the best possible location of a boundary is based on a sequence of ongoing GLR or KL tests too. It is implemented by applying a recursive maximum search for distances of different test and reference sequences, which are defined by possible optimal boundary position 'r'. The direction of the search depends on the segment type. If the segment is a transient (right branch of flow chart in FIG. 17), the optimal boundary is assumed to be in the interval $S_b < n < S_e$, so the direction of the search is from right to left (R is the test window and S is the reference window). If the segment is not a transient, the optimal boundary is assumed to be in the interval $S_e < n < S_e + L - 1$ and the search direction is from right to left (R and S remain under the same duty). If the optimal boundary position 'r' is assumed to be located in the interval $S_e < n < S_e + L - 1$, the lower bound of this boundary is $r = S_e$ and its upper bound is $nd = S_e + L - 1$. For all other potential boundary positions $r < s < nd$, the distance between a growing reference and fixed test windows—$D(R_0, S_0)$ ($R_0 = x(S_b, \ldots, s)$; $S_0 = x(s+1, \ldots, s+L)$) is compared with the distance between a fixed reference and growing test windows—$D(R_1, S_1)$ ($R_1 = x(S_b, \ldots, r)$; $S_1 = x(r+1, \ldots, s+L)$), as depicted in FIG. 18. Note that the total duration of the time series composed of both windows is identical in both cases of $D(R_0, S_0)$ and $D(R_1, S_1)$, and grows contiguously as 's' is increased.

The assumed optimal position r is updated to the value s whenever $D(R_0, S_0) > D(R_1, S_1)$, and the process of updating r is repeated up to the point where $s = nd$. At this point, the last value of r is the optimized boundary position, and the boundary search algorithm can be restarted as shown in FIG. 17.

If the optimal boundary position r is assumed to be located in the interval $S_b < n < S_e$, then the lower bound of this boundary is $nd = S_b$ and its upper bound is $r = S_e$. For all other potential boundary positions $nd < s < r$, the distance between a growing reference and fixed test windows—$D(R_0, S_0)$ ($R_0 = x(s, \ldots, S_e + L - 1)$; $S_0 = x(s - L, \ldots, s - 1)$) is compared with the distance between a fixed reference and growing test windows—$D(R_1, S_1)$ ($R_1 = x(r, \ldots, S_e + L - 1)$; $S_1 = x(r - 1, \ldots, s + L)$), as shown in FIG. 18. The total duration of the time series composed of both windows is identical in both cases of $D(R_0, S_0)$ and $D(R_1, S_1)$, and grows contiguously as s is increased. The assumed optimal position r is updated to the value s whenever $D(R_0, S_0) > D(R_1, S_1)$. The algorithm is continued up to the point where $s = nd$. At this point, the last value of r is the optimized boundary position, and the boundary search algorithm can be restarted as shown in FIG. 17.

Figure 19:
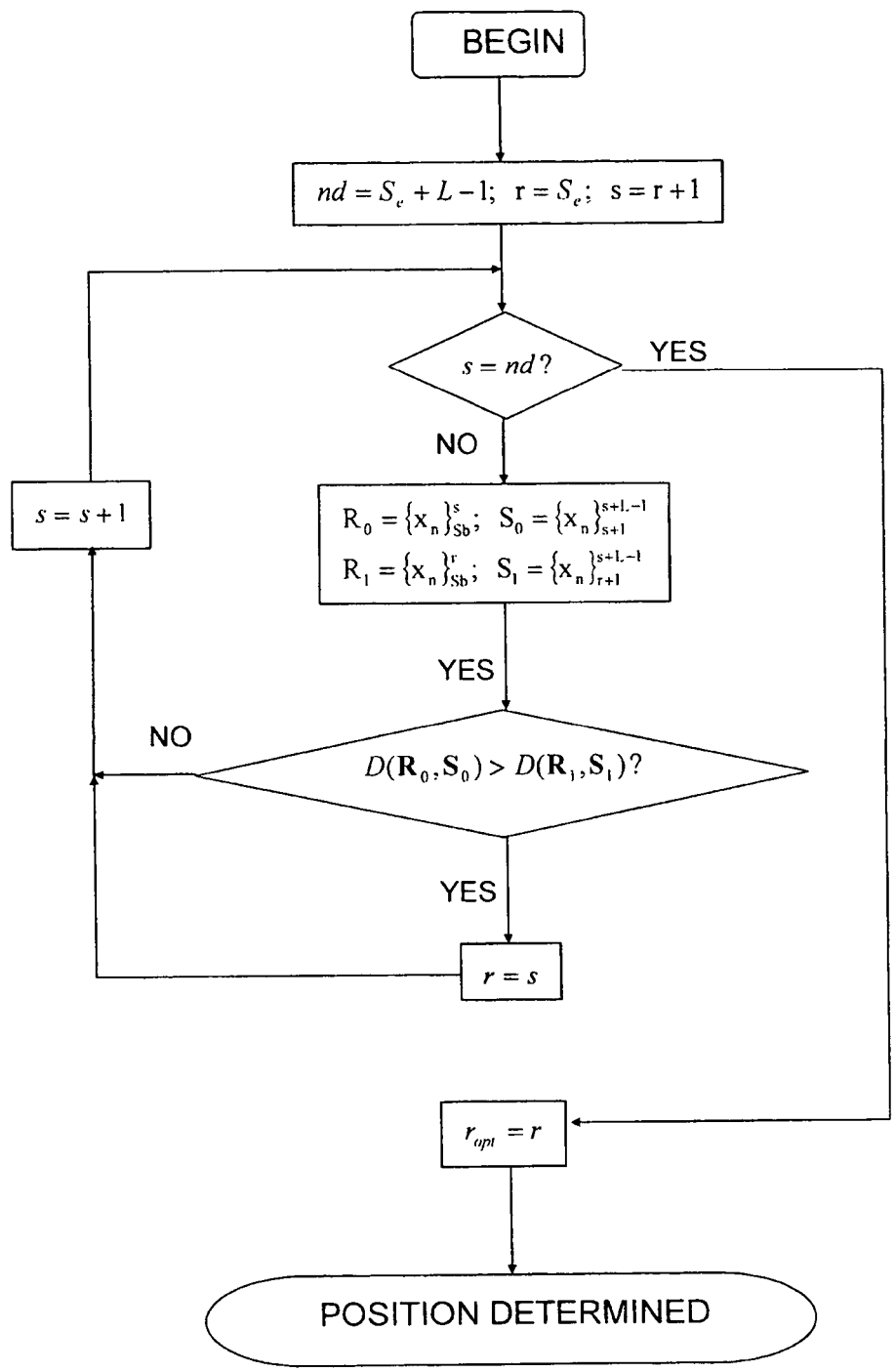
FIG. 19 schematically illustrates in more details the rightwards optimization segmentation process mentioned in connection with FIG. 18.
Figure 20:
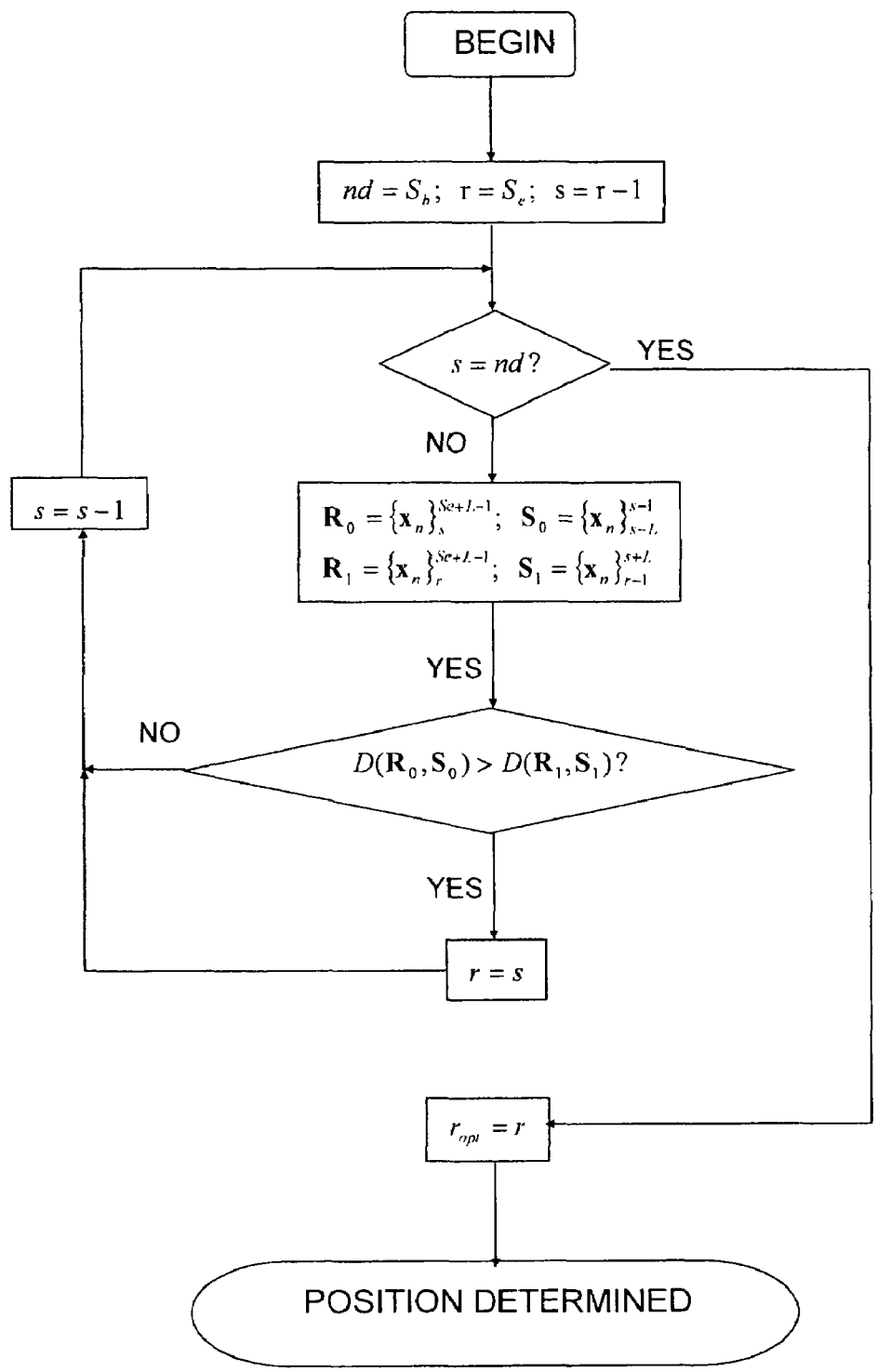
FIG. 20 schematically illustrates in more details the leftwards optimization segmentation process mentioned in connection with FIG. 18.

FIG. 19 illustrates a simplified flow chart of a rightwards boundary optimization algorithm, and FIG. 20 depicts a simplified flow chart of a leftwards boundary optimization algorithm.

Applying Multidimensional Adaptive Segmentation with Variant Sliding Window Size for each Dimension Given a multidimensional time series, the algorithm described herein above, enforces the use of a constant sliding window for each dimension. There are many cases where it is desirable to partition each series in the ensemble separately with different time window duration. For example, if multidimensional time series is formed by filtering a one-dimensional time series by a set of filters bank, it would be desirable to use a short duration sliding window for a time series, which emphasize high frequency behavior, and long duration sliding window for a time series which emphasize low frequency behavior.

Because normally sliding windows of different durations are used for adaptively segmenting each dimension, a problem arises, of unifying the boundaries identified in each dimension. The proposed unification algorithm, which is described herein below, decides which segment boundary will be included in the over-all segment boundary series and which is not. The decision criterion is based on the desire to cancel partitioning of phenomena, which are not predominant in their origin dimension with respect to the other dimensions and thus prevent over partitioning.

1. Description of the Unification Algorithm

All segment boundaries received by segmentation of each dimension are initially projected to a combined series of segments boundaries sorted according to their time appearance. The triplet s,d,T defines each projected segment boundary, where s represents time index, d represents dimension index (the origin dimension where the boundary came from) and T indicates if the projected boundary is an upper bound of a transient segment (T=1=⇒transient; T=0=⇒not transient).

The output of the algorithm is a new comprehensive sequence of boundaries, where each boundary is defined by P and K where P represents time index and K indicates if the boundary is an upper bound of a transient segment. The following steps describe the operation of the algorithm:

Initialize n=0

0. For i=1 to N do
1. For j=0 to M−1 do $V_L(j) = var(x_{s(i-1),j}, \ldots, x_{s(i),j})$ $V_R(j) = var(x_{s(i),j}, \ldots, x_{s(i+1),j})$ 2. For j=0 to M−1 do $V_L(j) = \frac{V_L(j)}{\sum_{j=1}^{M} V_L(j)}$ $V_R(j) = \frac{V_R(j)}{\sum_{j=1}^{M} V_R(j)}$ 3. If $((Max(V_L) > thresh_L) \& (ArgMax(V_L) = d(i))) | (Max(V_R) > thresh_R) \& (ArgMax(V_R) = d(i))$ Then $P(n) = s(i)$ If $(n > 0) \& (T(i) = 1) \& (d(n-1) = d(n)) \& (P(n-1) = s(i-1))$ Then $K(n) = 1$ Else $K(n) = 0$ $n = n+1$ A Matching Pursuit Based Waveform Classification Algorithm Many biomedical signals contain observable transient phenomena, which have unique time morphology, such as K-complex and spikes in an EEG signal. It is usually very difficult to model waveforms of such transient phenomena using only one analytical function. Therefore, it is necessary to model them as a sum of known basis functions. The matching pursuit algorithm performs this task (a reference may be made to "A Wavelet tour of signal processing", by Stephane Mallat p. 412).

Figure 21:
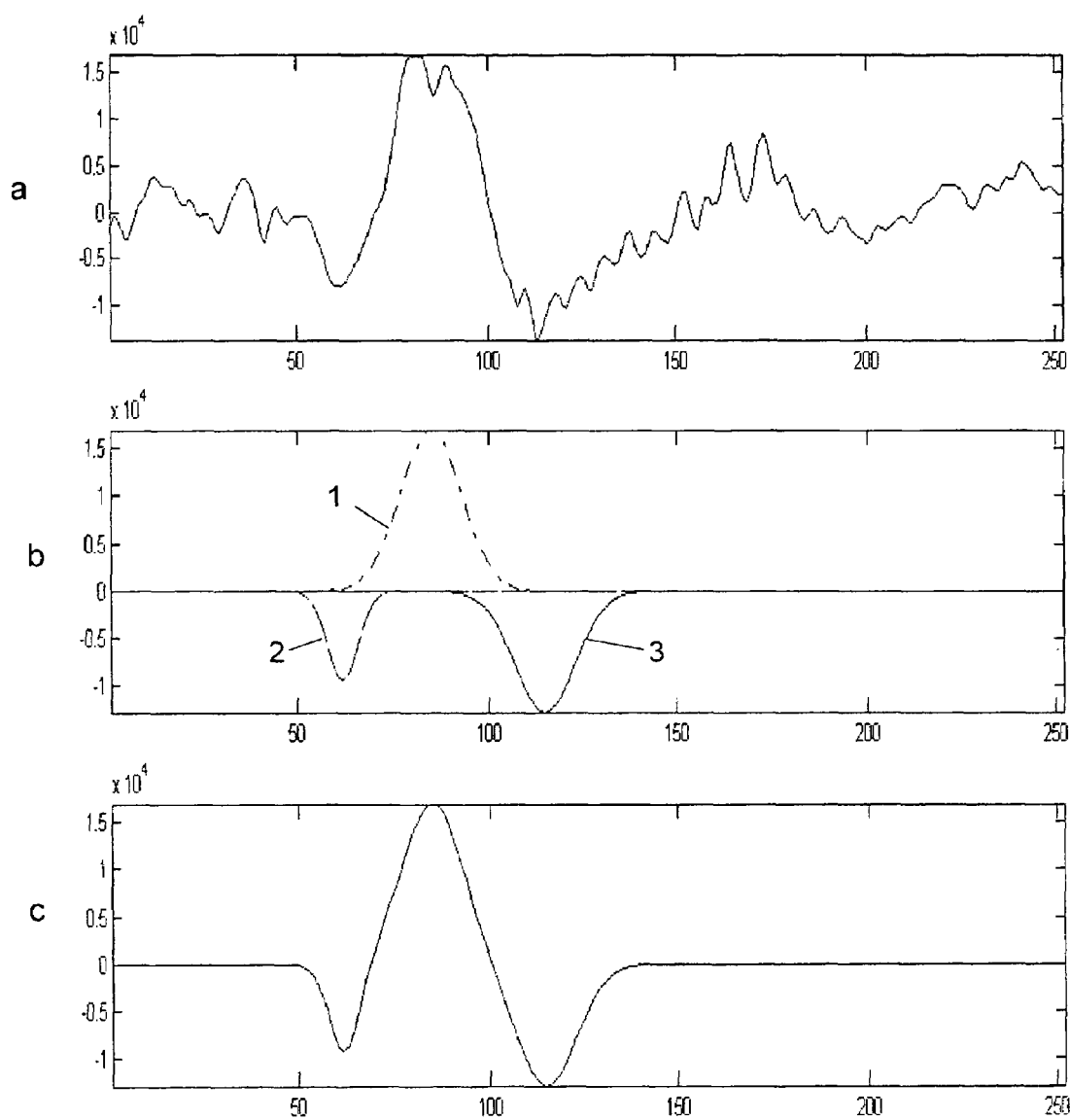
FIG. 21 depicts exemplary transient phenomena in EEG signal, and its characterization by utilizing basis functions, according to a preferred embodiment of the present invention.

The parameters of the basis functions that ensembles the waveform of the transient phenomena are utilized to extract features. FIGS. 21a to 21c show an example for utilization of three Gaussian functions (i.e., the known basis functions). FIG. 21a depicts a typical K-complex waveform (the waveform as originally peaked up from a monitored person). FIG. 21b depicts a set of three Gaussians (i.e., designated by reference numerals 1, 2 and 3), which ensemble the original waveform shown in FIG. 21a. FIG. 21c depicts the constructed waveform (essentially noiseless and artifact free-free waveform). The means and variances of the three Gaussians (shown in FIG. 21b) are utilized for classifying the constructed wave form, and thereby, the original waveform.

Density Estimation and Clustering Algorithms

In order to model a statistical behavior of a physiological/pathological state, it is desirable to estimate the probability density function that generates observations that are related to the physiological/pathological state. Two families of methods may be utilized for estimating unsupervised probability density:

1. Non-Parametric Methods

Which are based on multivariate non-parametric kernel density estimation $$\hat{f}(x_i) = \sum_{j=1}^{N} (2\pi)^{-d/2} |S|^{-\frac{1}{2}} \exp\{-0.5(x_j - x_i)^T S^{-1}(x_j - x_i)\} \quad (1.1)$$

Where $\{x_i\}_1^N$ is the observation sequence and S is the covariance matrix of the kernel function (a reference may be made to "Density estimation for statistics and data analysis", by B. W. Silverman, chapters 4 and 5).

2. Parametric Methods

This algorithm estimates, in unsupervised manner, the parameters of a probability density function modeled as Gaussian mixture of models (a reference may be made to I. Gath and A. B Geva, "Fuzzy clustering for estimation of the parameters of the components of mixtures of normal distributions", Pattern Recogn. Lett. 9: 77–86, 1989, and to "Non Linear Biomedical Signal Processing", Volume 1 Chapter 2 p. 34–40).

Handling ECG Signals

In connection with the ECG signal, the present invention utilizes the (known) Wavelet Transform Algorithm (WTA) for adaptive segmentation of heartbeats. The system also employs several digital Adaptive Matched Filters (AMFs) on the monitored (heart)Beat Under Test (BUT). An AMF is defined by a corresponding (shape) 'template', known as 'Matching Template', which is mathematically represented by a corresponding set of parameters. Different signal patterns/shapes may be identified by AMF by correspondingly defining other sets (i.e., templates) of parameters. The AMFs are utilized for allowing the system to detect and classify 'viable heartbeat' signal, and, after detecting several viable heartbeats (i.e., according to a predetermined criteria), to adapt to a person currently being monitored. By using the term 'viable heartbeat' it is meant to include every possible shape/pattern of a signal that resembles common Normal (see FIGS. 22a and 22b) and common (aberrant) Pathological (see FIGS. 22d and 22e) shape/pattern.

1) ElectroCardiogram (ECG)

Figure 22:
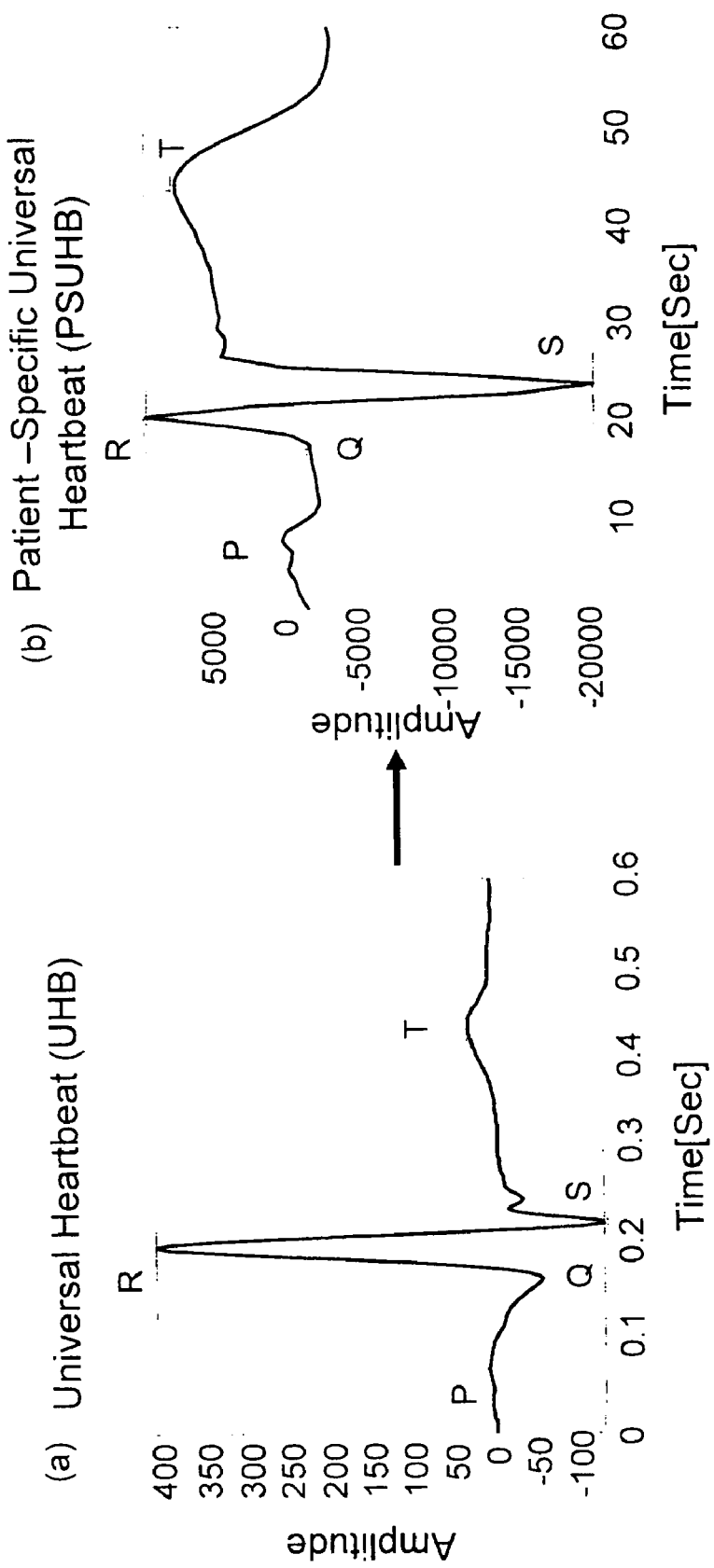
FIGS. 22a to 22e schematically illustrate typical normal heartbeats shape and two commonly known aberrant heartbeat shapes.
Figure 22:
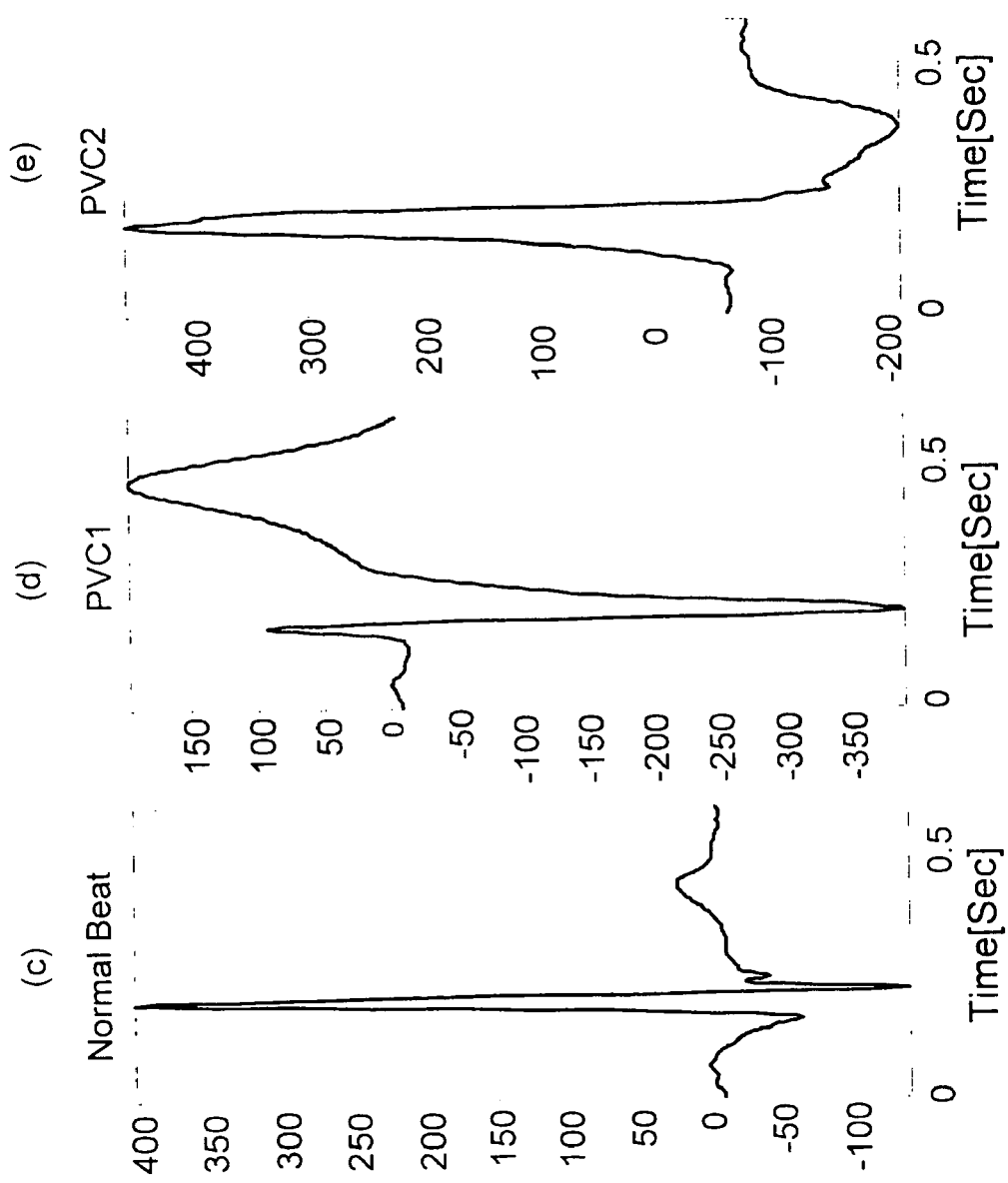

According to the present invention, whenever a person is connected to the system, the system adapts itself to the connected person by performing the following steps:

a) Detecting/identifying essentially every signal, that has at least a minimum resemblance to a heartbeat-like shape (i.e., a viable heartbeat), that is contained within the first monitored ECG segment (i.e., portion), the duration of which is predetermined by the clinician, and may be varied by him according to the circumstances (e.g., whenever the shape of the heartbeats of the monitored person are problematic), by comparing the signal to a reference 'Template No. 1', which is initialized with a universal reference shape (hereinafter referred to as the 'Universal HeartBeat'—UHB, see FIG. 22a), which was obtained by averaging several normal-shaped heartbeats of several persons. If no minimum resemblance is met with the UHB, an ECG verification algorithm (hereinafter referred to as the 'ECGVA) is utilized for establishing whether there is the lack of minimum resemblance is due to the signal being other than an ECG signal (synchronization signal, noise, constant zero signal, etc . . . ). The ECG signal is a self correlated signal, thus, by dividing the portion to "heartbeats", the ECGVA creates an AMF suitable for the present portion, and tests the resemblance of each "heartbeat" to the AMF. By meeting high resemblance criteria, the ECGVA will accept that the present portion is an ECG signal that does not resemble the UHB and will allow to proceed to the next step of the ECG analysis. If the ECGVA will not accept the portion as an ECG signal, it will alarm the user that the input signal is not an ECG signal, and, therefore, that no adaptation will occur. This will continue until the right criterion is met for the adaptation process.

b) Employing a predetermined criteria for averaging the viable heartbeats detected by use of the UHB, for obtaining an average heartbeat shape that is unique to the monitored person (hereinafter referred to as the 'Patient-Specific Universal HeartBeat'—PSUHB, see FIG. 22b). Template No. 1 is assigned the characteristics of PSUHB in order to utilize it as the unique reference of the person being monitored;

c) Comparing additional heartbeat-like signals, in corresponding additional portions of the ECG signal, to the PSUHB reference;

d) Whenever a new viable heartbeat is detected by using the updated Template No. 1 (i.e., PSUHB), storing it and analyzing its medical implications;

e) updating Template No. 1 (i.e., PSUHB), according to a predetermined criteria, by utilizing additional new viable heartbeats for re-averaging the monitored person's unique viable heartbeats, according to predetermined criteria, for allowing the system to enhance its adaptation to the monitored person; and f) Repeating steps c) to e).

Viable Heartbeats

Prior to employing Template No. 1 on a Beat Under Test (BUT), the system first identifies the relative time-wise location of the BUT within the continuous ECG signal.

The BUTs are identified by manipulating several signals related to the corresponding output channels of the WTA. The number of the channels depends on the frequency at which the ECG signal was originally sampled. In a first WTA output signal (commonly referred to as the 'high scale'), the high frequency content of the ECG signal is emphasized (see FIG. 21a). The lower the 'scale', the lower the dominant frequency of the ECG signal that is emphasized (see FIG. 21b and 21c).

According to the present invention, the absolute values of the first three 'scales' (FIG. 23a, 23b and 23c) are 'summed-up', resulting in a signal (FIG. 23d) having a high peak, which allows an easy detection of 'R-peak' of every heartbeat. Due to the latter signal manipulation, the 'R-peak' of a heartbeat will always be the most perceptible point in the heartbeat, and, therefore, will be easily detected and will essentially eliminate the risk of misdetection of R-peaks (i.e., due to noises, movements, T waves and other types of interference).

As shown in FIG. 23d, there are two points that have a larger energy, i.e., the heartbeats marked as 'AR'. Nevertheless, the lower-energy R-heartbeats are viable heartbeats and will be analyzed accordingly. From the signal depicted in FIG. 23d, the R-peaks are "placed" in the filtered ECG signal, as shown in FIG. 23e.

Each AMF outputs a probability value (between 0.0 to 1.0), indicating the resemblance between the BUT to the corresponding template. The larger this value, the more the BUT resembles to the corresponding template. The corresponding AMF outputs a Normalized Correlation (NC) value, which is compared to a first threshold value $NC_{TH1}$. If $NC>NC_{TH1}$, it indicates that a viable heartbeat has been detected, in which case it is further processed.

The PSUHB may be updated, as ECG signal continues to 'feed' the system, according to one of the following principles:

(1) whenever several viable heartbeats are detected within a predetermined time interval, the PSUHB is calculated by averaging only the viable heartbeats detected in the last ECG segment; or (2) as in (1), only that the PSUHB is calculated by averaging the viable heartbeats detected in every ECG segment; or (3) whenever predetermined number 'n' of viable heartbeats are detected, the PSUHB is calculated by averaging only the last 'n' viable heartbeats that were detected; or (4) as in (3), only that the PSUHB is calculated by averaging all of the detected viable heartbeats; or (5) whenever a new viable heartbeats is detected, the PSUHB is calculated by averaging all of the viable heartbeats; or (6) whenever a predetermined time-interval elapses.

Whenever a new PSUHB is calculated, it is used as a new reference template for allowing the system to identify new viable heartbeats in future ECG segments of same monitored person. As ECG signal continues to be input into the system, the system converges from the generalized universal (mean) heartbeat patterns into the specific patient's heartbeat patterns (i.e. the system 'familiarizes' itself with, or 'learns', the inherent cardiac condition of the currently monitored patient). The latter process is employed on Normal heartbeat, as well as on Pathological heartbeat, and it allows the TMP to determine accurately the cardiac status of the examined person. If the examined (current) heartbeat is identified as pathological, a second classification process is employed, for determining the exact type of the pathology, after which the current identified pathological type is utilized for calculating a new mean pattern that is essentially more accurate than the previous calculated mean pattern.

At the time a (new) person is connected for the first time to the system, the system does not have any patient-related data, and therefore it must utilize a relatively 'weak' criteria to start identifying the first person's BUTs. Therefore, the system utilizes the UHB, which is associated with a relatively low threshold value $NC_{TH1}$. However, after the first PSUHB is calculated, i.e., after the first ECG segment provides the system with some unique patient-related data (i.e., data that reflects the inherent cardiac condition of the person currently being monitored), a 'harsher' criteria is employed by the AMF, by utilizing a second threshold value $NC_{TH2}$ (i.e., $NC_{TH2} > NC_{TH1}$)

Whenever a viable heartbeat is detected, which is not pathological heartbeat, the system considers it as Normal heartbeat. Each Normal heartbeat is segmented into four clinically important segments: QRS, ST, PR and QT. The segmentation process is based on the prior knowledge of the relative location of the R-wave, T-wave and P-wave of each normal heartbeat, which were found by employing the WTA at an earlier stage, as described before.

Accordingly, the system finds the corresponding segments boundaries by:
(1) Finding the peak of the Q-wave;
(2) Finding the onset of the Q-wave;
(3) Finding the peak of the S-wave;
(4) Finding the end of the S-wave;
(5) Finding the peak of the T-wave;
(6) Finding the onset of the T-wave;
(7) Finding the end of the T-wave;
(8) Finding the onset of the P-wave;

The system automatically searches for the above-specified boundaries while synchronized with the R—R interval, which was accurately found by the WTA in an earlier stage of the analysis. Accordingly, the system provides a person-adaptive and heartbeat rate adaptive segmentation process.

T-wave Detection

The major problem in the segmentation process is to precisely characterize the T-wave, i.e., to precisely detect its shape and phase, which are critical for a precise determination of the ST segment and the QT interval. According to the invention, the T-wave of a heartbeat is characterized, i.e., a decision is automatically made, regarding whether the T-wave is 'normal, 'upside-down' or 'bipolar'. The T-wave characteristics are found by identifying its onset and endpoint.

ST Analysis

One of the clinically most important parameter associated with cardiac condition, is the ST depression/elevation, as this parameter may indicate a symptom for heart attack. In order for the system to evaluate the ST segment, it selects a portion of the ECG, which is contained within the isoelectric interval (the isoelectric interval is defined as the time between the end of the former T wave and the onset of the current P wave), which is located between two consecutive heartbeats. Then, the system 'extracts' 0.1 Second of this interval, which is utilized as a reference segment, to which the ST segment is compared. An absolute margin is calculated between the mean magnitude of the ST segment and the mean magnitude of the reference segment. ST depression/elevation is identified if the absolute margin is larger than a threshold value.

QT Analysis

The duration of the QT interval is calculated, as well as the variability of said duration and the corresponding spectrum, by utilizing models known as the 'AR-models'.

Sometimes, the 'normal' heartbeat of a person does not include a perceptible R-wave (i.e., which the system can not identify or detect). Therefore, the system is configured to search for P-waves in these heartbeats, measure the QRS duration and check if the heartbeat is not premature. If these conditions meet certain criteria, the system considers the corresponding heartbeats as viable heartbeats, and the AMF's template is updated accordingly and automatically by the system.

The system also calculates Heart Rate (HR) and Heart Rate Variability (HRV) parameters, which derived from the ECG signal by employing adaptive techniques. Calculation of HR and HRV is implemented by utilizing only Normal heartbeats and another type of HR and HRV is implemented by utilizing the type of heartbeats defined by the user, thus, if the user decides to utilize pathological heartbeats as well as normal heartbeats the system will comply with the decision. If a type of heartbeat is detected that is not part of the HR and HRV implementation, the system will calculate the time gap created by canceling this heartbeat from the ECG signal and will "fill" it with a normal heartbeat (for HR and HRV calculation only!). The placement of the artificial normal heartbeat is established by a constant learning of the specific patient HR behavior, thus, achieving a most accurate adaptive and automatic learning base HR and HRV calculation.

The system is capable of detecting HR abnormalities from different biomedical signals such as those derived from the signals associated with a heart condition, the patient movement activity, sleep stage, etc., by utilizing an automatic physiological/pathological events detection and a set of fuzzy rules.

Viable Heartbeats

The first stage to establish the type of heartbeat is to decide whether the morphology at hand (BUT) is a normal heartbeat or a noisy heartbeat or suspected to be an aberrant heartbeat. If the resemblance of the BUT to Template No. 1 is greater than $NC_{TH2}$ the system will define the BUT as a normal heartbeat. In case the resemblance harsh criteria is not met, the system checks whether the morphology mismatch is a product of movement artifact or the heartbeat is suspected to be an aberrant one. By using an adaptive and learning base environmental movement detection algorithm (AEMDA), the system calculates the fuzzy degree of the movement level (DML) and the fuzzy degree of the BUT energy in relevance to the movement degree (DME). A supplemental fuzzy degree calculation of the resemblance of the BUT to the pathological template (Template No. 2 and Template No. 3) is added to a final fuzzy based decision algorithm, which will make the decision whether it is a movement artifact or a suspected pathological heartbeat and therefore it will be further processed.

Aberrant Heartbeats

Whenever a suspected aberrant heartbeat is detected (i.e. by use of Template No. 1 and AEMDA), the system compares it to two commonly (universally) known aberrant heartbeats (i.e., PVC1 and PVC2), by which Templates No. 2 and 3 are initially assigned:
(1) Template No. 2—Universal Pathological HeartBeat No. 1 (UPHB1) template. This template is initialized by the shape of the PVC1, which represents essentially any signal pattern that resembles a first commonly known aberrant heartbeat (i.e., PVC1, see FIG. 22d), and was obtained by averaging several aberrant heartbeats from several persons (having the same pattern as the first known aberrant pattern); and (2) Template No. 3—Universal Pathological HeartBeat No. 2 (UPHB2) template. This template is initialized by the shape of the PVC2, which represents essentially any signal pattern that resembles a second commonly known aberrant heartbeat (i.e., PVC2, see FIG. 22e), and was obtained by averaging several aberrant heartbeats from several persons (having essentially the same pattern as the second known aberrant pattern).

Employing these two templates results in two Normalized Correlation values (i.e., $NC_{P1}$ and $NC_{P2}$, respectively). Normally, $NC_{P1} \neq NC_{P2}$. Therefore, the system selects the UPHBi (i=1 or 2) that yields the maximal NC (i.e., between $NC_{P1}$ and $NC_{P2}$), the maximal NC is then given a fuzzy degree (Correlation Pathology Degree—CPD). To establish whether the BUT is an aberrant heartbeat, the system calculates the fuzzy degree of the high frequency noise (which might be caused by EMG high energy) by using an adaptive and learning based environmental high frequency noise detection algorithm (AHFNDA), third correlation with template No. 1, and calculation of the length of the QRS in the BUT. Each of these parameters is given a fuzzy degree, thus, high frequency noise level will be measured through NLD (Noise Level Degree), and normal heartbeat resemblance will be measured through CND (Correlation Normal Degree) and the length of the QRS segment will be measured through QRSLD (QRS Length Degree). There are several decision making algorithms, according to the type of the UPHB selected (1 or 2) and the level of resemblance (NC), the system decides which decision making algorithm will be used.

If the BUT is detected as type 1 and meets a high resemblance degree to PVC1, 2 new fuzzy parameters are calculated: PVCDeg which consists of the fuzzy degree of no noise detected and the resemblance of the BUT to PVC1 and the other parameter NormalDeg consists the degree of no noise detected and the resemblance of the BUT to a normal heartbeat. If those 2 parameters are low the system will classify the BUT as noise, if the NormalDeg is very high or is higher than PVCDeg and the QRSLD is low the BUT will be classified as normal heartbeat and if PVCDeg is higher than NormalDeg and NormalDeg is not very high the BUT will be classified as a aberrant heartbeat.

If the BUT is detected as type 2 and meets a certain resemblance degree to PVC2, the system checks several rules. If the NLD is high and the NC is not very high the BUT will be classified as noise. If the QRSLD is low and the BUT is premature, it will be classified as aberrant heartbeat, but if it is not premature it will be classified as normal heartbeat. If the QRSLD is high and the NLD is high, the BUT will be classified as noise. If the QRSLD is within the aberrant limits and the BUT energy is not very high or very low in relevance an adaptive mean energy of heartbeats calculation, the BUT will be classified as aberrant heartbeat and if the energy is to low or to high it will be classified as noise.

If the NC is relatively low, the system makes further investigations on the BUT to decide whether it is an aberrant heartbeat which does not resemble to PVC1 and PVC2, or it is noise. To achieve that the system calculates a new fuzzy parameter UNL (UnNoise Level), this consists of the no noise degree and the maximum between CPD and NPD. If the UNL is low, the BUT will be classified as noise. If the UNL is high and the QRSL is not very high the BUT will be classified as aberrant heartbeat.

After detecting several aberrant heartbeats, the system may learn the patient-specific aberrant heartbeat patterns and introduce to a clinician a corresponding sequence of pathological heartbeats.

If the system decides that the viable heartbeat essentially an aberrant heartbeat from type PVC1 or PVC2, it stores it for calculating new corresponding templates (i.e., PSUPHB1 and PSUPHB2, respectively), which reflect the corresponding patient-specific aberrant heartbeat. Calculating PSUPHB1 and PSUPHB2 is implemented according to the same principles described in connection with the PSUHB.

Premature Normal Morphology Heartbeats

The system detects PACs (Premature Atrial Contractions). If the BUT has a normal morphology (meets the resemblance criteria to Template No. 1) and the BUT's R-wave is close to the former R-wave, the BUT will be classified as PAC. To define what is close, the system learns the length, or distance, between two consecutive R-waves in the specific patients and to optimize the detection, the learning process is repeated as long as the patient is monitored. This way, the system adaptively learns the Heart Rate (HR) behavior of the patient.

Pathological Sequences

After a viable heartbeat is identified as aberrant heartbeat, it is stored, and a corresponding sequence of pathological heartbeats is established there from. There are several commonly known pathological sequences ('A' and 'N' indicate 'Aberrant' and 'Normal' heartbeats, respectively):

(1) VT—A, A, A, A, A, . . . , (generally seen in a tachycardia-type disorder associated with the ventricles). VT is detected by finding a sequence of pathological heartbeats and instantaneous Heartbeat Rate (HR) that exceeds a clinically predetermined threshold value;

(2) SVT—PAC, PAC, PAC, PAC , . . . , (generally seen in another type of tachycardia disorder); (PAC—Premature Atrial Contraction, as seen in the ECG as a normal heartbeat morphology only if it is premature);

(3) Bigeniny—A, N, A, N, A, N, . . . ;

(4) Trigeminy 1—N, N, A, N, N, A, N, N, A, . . . ;

(5) Trigeminy 2—A, A, N, A, A, N, A, A, N, . . . ;

(6) Tachycardia—accelerated heartbeat rate. Tachycardia is detected by finding several consecutive heartbeats having a rate that is above a certain clinically predetermined threshold value; and (7) Bradycardia—too low heartbeat rate. Bradycardia is detected by finding several consecutive heartbeats having a rate that is below a certain clinically predetermined threshold value.

Figure 24:
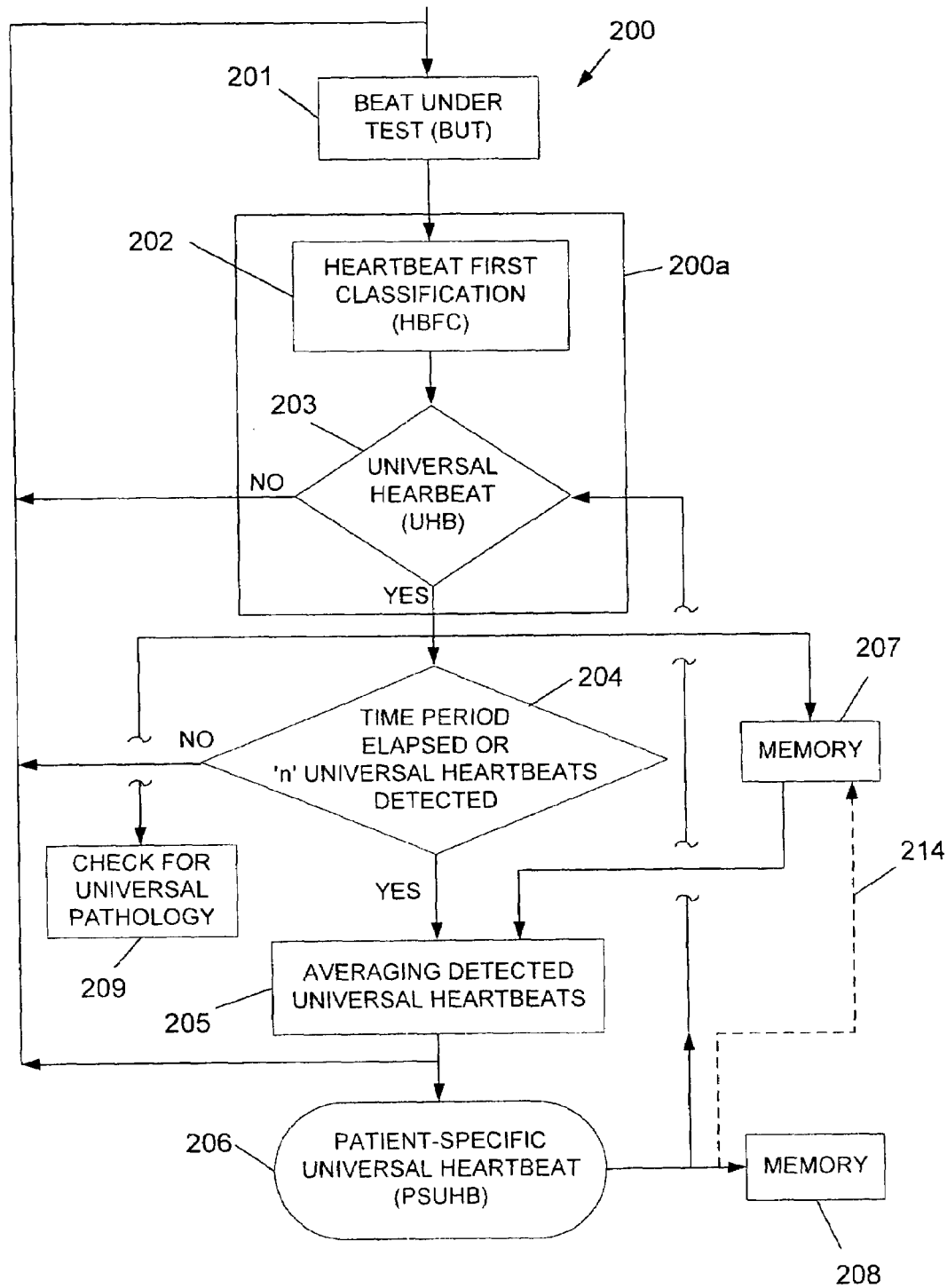
FIG. 24 is a block diagram illustrating the system's adaptation to the Patient-Specific Universal Heartbeat (PSUHB), according to a preferred embodiment of the present invention.

FIG. 24 schematically illustrates the initial identification of signals having essentially a heartbeat-like waveform, according to a preferred embodiment of the present invention.

In order to avoid wasting processing time on signals that do not resemble heartbeats, a first classification process is employed (202) on the current Beat Under Test (BUT) 201.

Even though there is a considerable variance involved in signals that represent heartbeats of different persons, these signals are characterized by having typical (noticeable) patterns. An average heartbeat pattern was established by averaging heartbeats of several persons (the 'average heartbeat pattern' is hereinafter referred to as Universal Heart-Beat—UHB). Accordingly, the first monitored BUT is compared to the UHB (203) in order to decide whether it is to be considered as a viable heartbeat. The comparison process and resulting decision (200a) is implemented by utilizing a digital filter that is commonly referred to as a "Matched Filter", which allows implementation of a "Matched Template"). The Matched Filter (MF) is configured to identify predefined signal pattern (i.e., "template") by employing a corresponding set of parameters. The resulting decision 203 of the MF 200a involves a correlation factor, the value of which may be between 0.0 and 1.0. The higher the value of the correlation factor, the more the examined pattern resembles the predefined template of the MF. Since the magnitude of the BUTs may have a significant variance (i.e., due to movements of the sensing electrode, clinical reasons and non-standard amplifiers/equipment), a phenomena that may ill affect the resulting decision, the BUT is Normalized (not shown). MF 200a allows identifying even severely deformed heartbeats (i.e., pathological heartbeats). However, if the current BUT is too corrupted/deformed (i.e., there is very low correlation between the BUT and the MF's template), it is not processed for detecting pathologies. Nevertheless, the corrupted heartbeat may be stored for (whenever required) allowing performing future analysis. Assuming the system identifies heartbeats that essentially match the UHB (i.e., 'proper heartbeat'), it stores these heartbeats, and, according to a first approach, whenever a predetermined time interval elapses (204), calculates an average pattern (205). The averaged pattern is the 'Patient-Specific UHB' (PSUHB) 206, which is stored in memory 208 (or in memory 207). If the BUT does not match the UHB (203), the system checks the next BUT (201). According to a second approach, the PSUHB is recalculated each time the system identifies new 'n' proper heartbeat (204). Every time a new PSUHB is calculated, it is utilized as a new universal heartbeat reference (203), to which the new BUTs are compared. The PSUHB is constantly updated, providing that new BUTs are sampled, thereby allowing the system to adapt itself to (i.e., learns) the patient's inherent cardiac condition. The learning process allows the system to reach accurate decisions regarding the patient's cardiac condition.

Each time a proper heartbeat is identified, it is stored (207) and analyzed for further classification, e.g., for identifying pathological type (209), if such exists.

Figure 25:
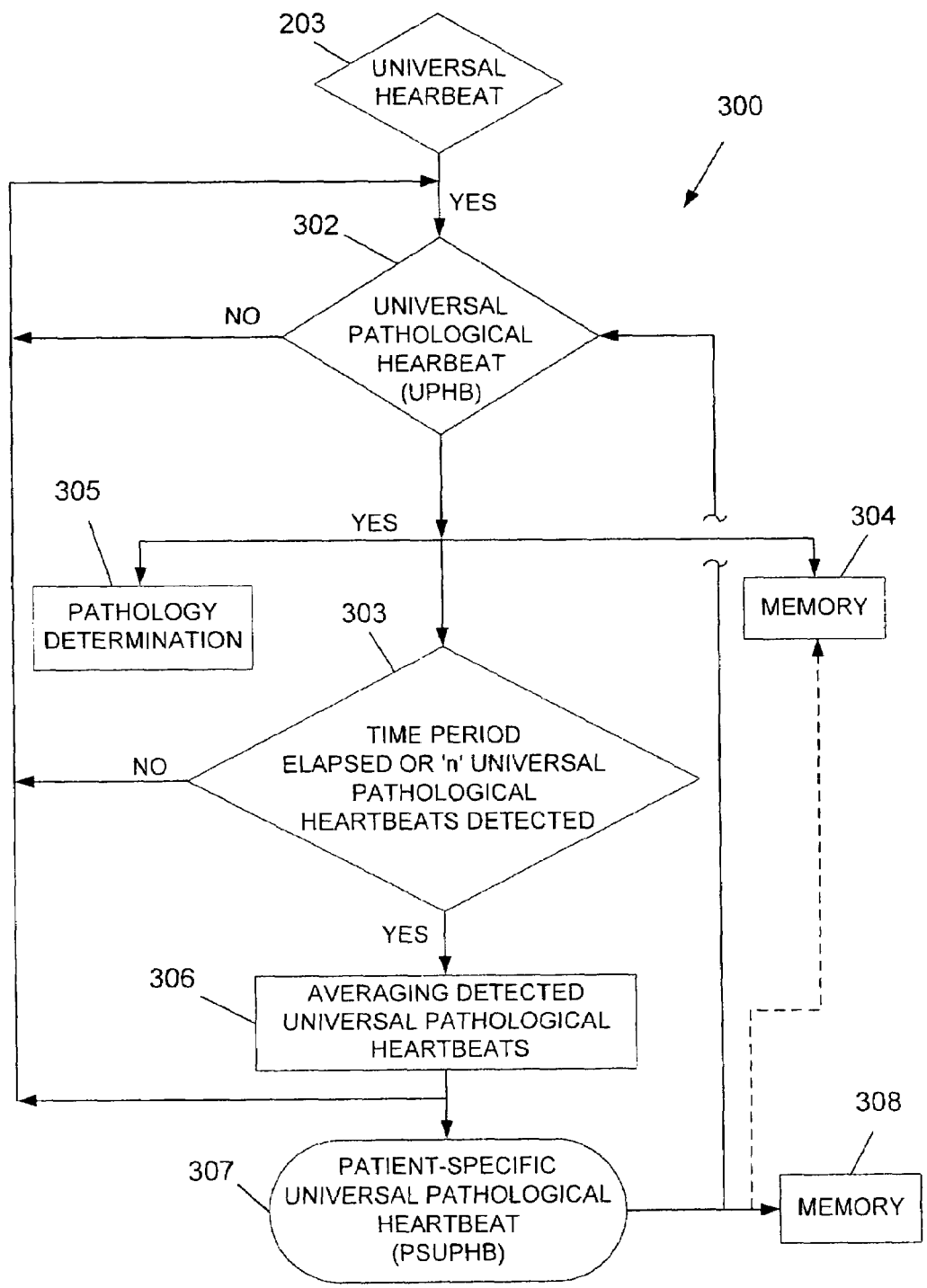
FIG. 25 is a block diagram illustrating the system's adaptation to the Patient-Specific Universal Pathological Heartbeat (PSUPHB), according to a preferred embodiment of the present invention.

FIG. 25 schematically illustrates the initial identification of pathological-like waveforms, according to a preferred embodiment of the present invention. After a BUT is identified as UHB (203), it is compared to Universal Pathological HeartBeat (UPHB) 302. The comparison process in this case is implemented also by utilizing a MF, which has been configured to identify particular pathological patterns.

If a current BUT meets the criteria of UPHB (302), it is further processed in order to determine its exact pathology type (305). In addition, a Patient-Specific Universal Pathological HeartBeat (PSUPHB) (307) may be determined in a way similar to determining PSUHB (206), i.e., steps 303 and 306 (FIG. 25) are essentially identical to steps 204 and 205 (FIG. 24), respectively. Each time a PSUPHB (307) is calculated, it is utilized as a new reference pattern (i.e., template) for Matched Filter 302, to which new UHB (203) are compared, until a new PSUPHB is calculated again (307). This way, the system adapt to (i.e., 'learns') the patent's inherent pathological cardiac condition.

Current UPHB (302) and PSUPHB (307) may be stored in memory 304 and/or in memory 308.

Figure 26:
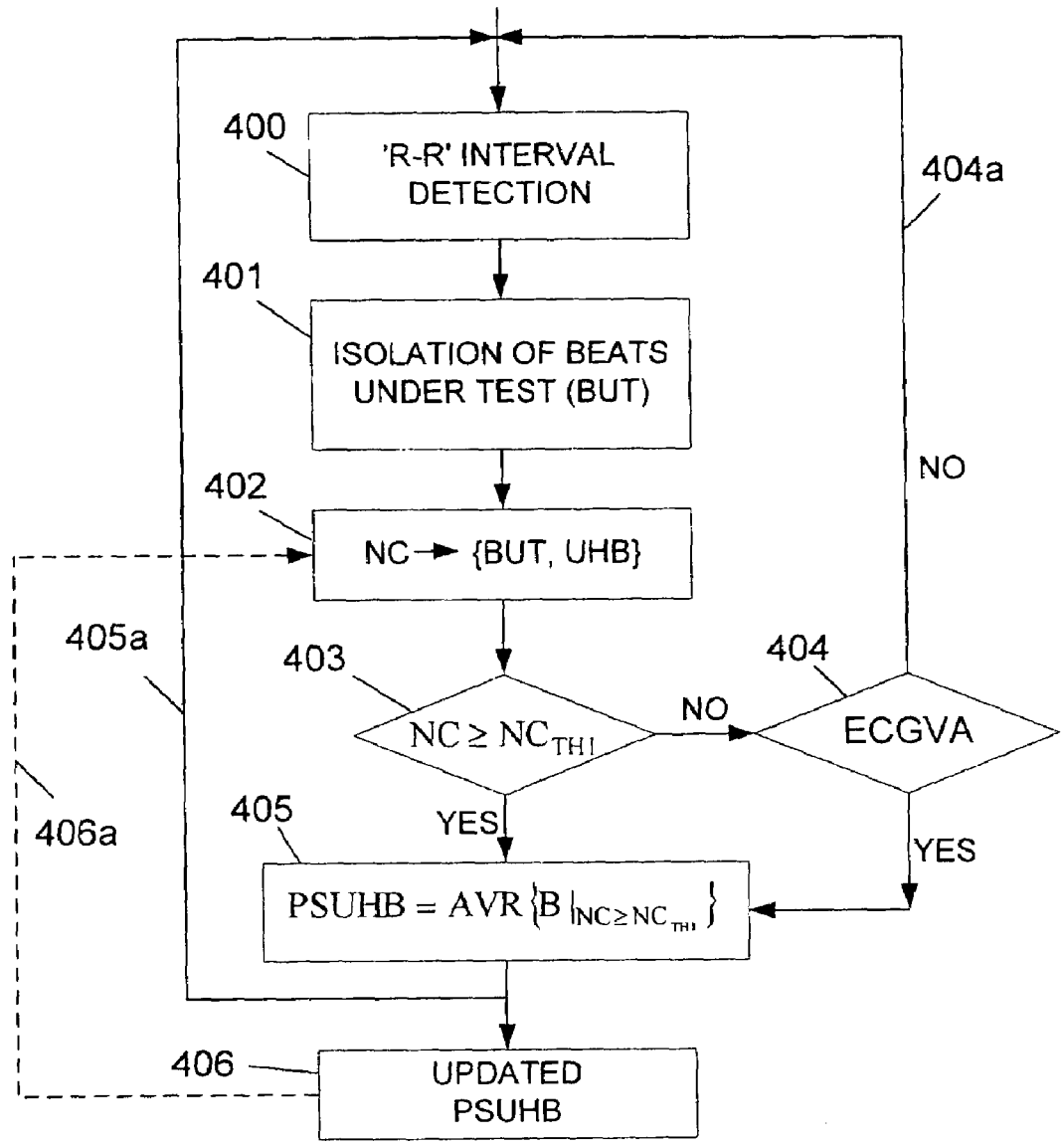
FIG. 26 schematically illustrates a more detailed system's adaptation to the Patient-Specific Universal Heartbeat (PSUHB), according to a preferred embodiment of the present invention.

FIG. 26 schematically illustrates the adaptation principle of the system to the Patient-Specific Universal HeartBeat (PSUHB), according to a preferred embodiment of the present invention. The adaptation process continues as long as new viable heartbeats are identified as having high normalized correlation (NC) value, as described hereinafter.

A group of consecutive BUTs is isolated (401), by employing R—R intervals detection (400). Consecutive normal heartbeats are then correlated with a Universal HeartBeat (UHB) that is stored in the system (402), and a 'Normalized Correlation' (NC) value is calculated (402) for each one of the heartbeats, by utilizing a corresponding Matched Filter (not shown) in the way described in a previous Patent application (i.e., IL No. 147502) of the present applicants. If the condition $NC \geq NC_{TH1}$ (403) is met for each one of the consecutive heartbeats, wherein $NC_{TH1}$ is a threshold NC (having a typical value of 0.7), these consecutive heartbeats are averaged, whether on a time interval basis or viable heartbeats count, yielding a new PSUHB (405) that is utilized as a (new, or updated) reference,(i.e., MF template), at step 406, for the next heartbeat (s) (405a).

The more viable heartbeats are identified, which have high correlation values, the more accurately the system converges (i.e., adapts) to the specific patient being examined. However, if a second situation occurs, i.e., a patient normally has heartbeats that do not conform to the reference pattern/template stored in the storage array (i.e. the condition 403 is not met for relatively large duration, an ECG Verification Algorithm ( ECGVA) is utilized (at step 404) to determine whether there is a minimum resemblance between the BUTs and the shape of a heartbeat, or, otherwise, the ECG signal may be ill-synchronized, or too noisy, or the signal is, in fact, constant zero signal, etc. This way, the system is capable of adapting itself to a patient even in cases in which the patient doesn't have a very similar normal (but non-pathological) viable heartbeat patterns.

The ECG signal is a self-correlated signal. Therefore, by dividing the ECG portion to "heartbeats", the ECGVA (404) creates an Adaptive Matching Filter (AMF) that is suitable for the current portion and tests the resemblance of each "heartbeat" to the AMF. By meeting high resemblance criteria, the ECGVA will recognize that the current portion is an ECG signal that does not resemble the UHB (402) and will allow proceeding to the next step of the ECG analysis. If the ECGVA will not accept the portion as an ECG signal, it will alarm the user that the input signal is not an ECG signal at all, and, therefore, no adaptation (i.e., of the system to the monitored person) will occur. This will continue (404a) until the criterion for the adaptation process is met, in which case a new average heartbeat will be calculated (405), and a new PSUHB reference will be obtained (406), after which the new obtained PSUHB reference will replace the current UHB (406a) for the correlation process carried out at step 402 with respect to future heartbeats.

Figure 27:
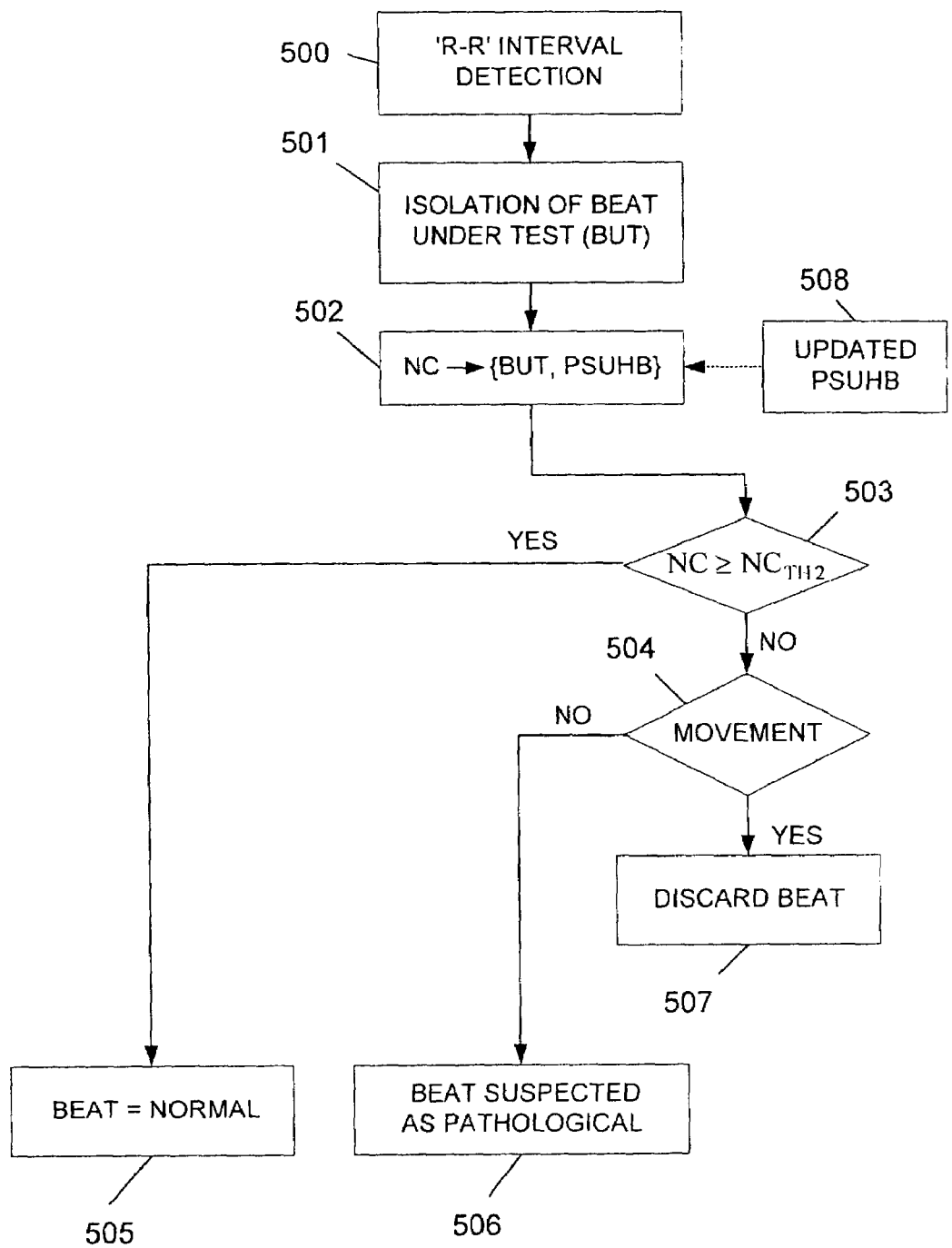
FIG. 27 schematically illustrates the heartbeat classification process, according to the preferred embodiment of the invention.

FIG. 27 schematically illustrates the heartbeat classification process, according to the preferred embodiment of the invention. The function of blocks indicated 500 and 501 is similar to these of blocks indicated 400 and 401 described in connection with FIG. 26. The PSUHB, which is calculated per patient according to the process described in connection with FIG. 4, is utilized as a reference template. The current BUT is correlated with the PSUHB (502) that is stored in a storage array (not shown), and a NC is calculated (502). If the condition $NC > NC_{TH2}$ is met (502), wherein $NC_{TH2}$ is a second threshold of NC, the current BUT is considered to be a viable heartbeat. Since at this stage the system is already adapted, at least to some extent, to the patient being monitored (i.e., it utilizes the PSUHB rather than the UHB), the criteria, which is utilized by the system for identifying viable heartbeats may be harsher, namely, $NC_{TH2} > NC_{TH1}$. The latter threshold reflects the large variance, and therefore low correlation value (e.g. 0.7), of heartbeats of different people, and it is required only at the first stage of the analysis, in which the system adapts (i.e. converges) itself to specific patient. After completing the adaptation phase, and due to the relatively small variance (and, therefore, high expected correlation value) of the heartbeats of the same specific patient, the value of the NC could be increased (e.g. to 0.85), for ensuring high precision based decisions regarding the classification of BUTs.

If the condition 503 is not met, i.e., the BUT has small correlation value, the BUT is likely to contain artifacts interference or noise. Therefore, a second decision is made in accordance with movement data (504). If no movement has been detected while sampling the current BUT, this BUT is suspected as pathological heartbeat (506), and the suspected heartbeat undergoes another process (not shown), the function of which is to classify the exact pathology type associated with this BUT. However, if an artifact has been identified, a decision is made (504) that the BUT was sampled under very noisy environment conditions, and it is to be discarded (507).

Figure 28:
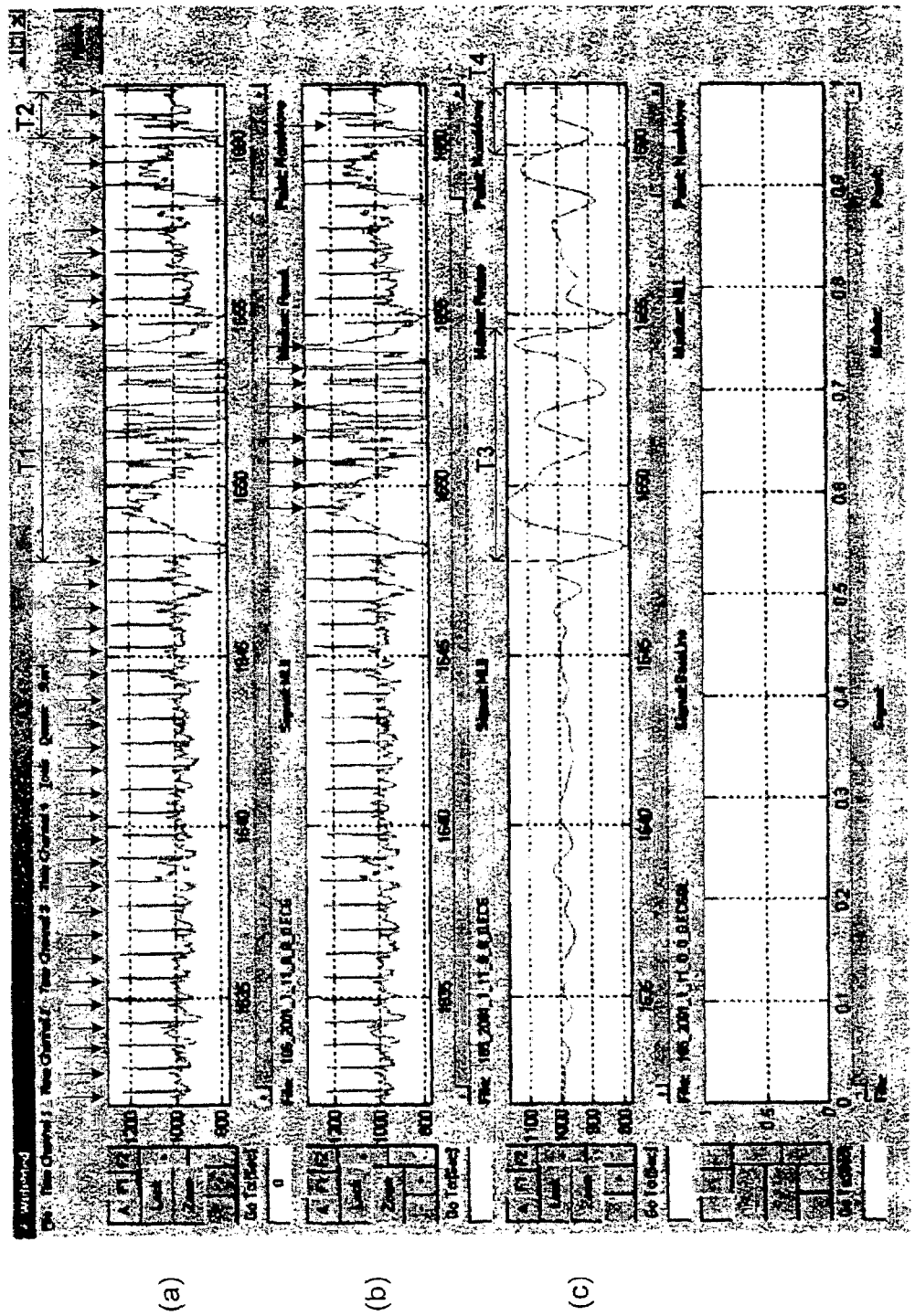
FIG. 28 shows exemplary testing results of the first heartbeat classification process according to which viable heartbeats are classified, according to a preferred embodiment of the present invention.

FIG. 28 shows testing results of the first heartbeat classification process according to which viable heartbeats are classified, according to a preferred embodiment of the present invention. The system is capable of distinguishing noisy viable heartbeat from noiseless viable heartbeats. Channel (a) shows the ECG signal, in which the viable heartbeats have been identified and marked by the system (i.e., by corresponding vertical arrows). These viable heartbeats were originally marked by yellow vertical lines (on the computer's screen) and have been replaced by said vertical arrows, for demonstration purpose. In addition, the problematic ECG signal in sections T1 and T2 was originally marked by a conspicuous color in order to attract the clinician's attention. Channel (b) shows the ECG signal, in which the viable noisy heartbeats have been identified and marked by the system (i.e., by corresponding vertical arrows), and channel (c) shows the movement that was detected in time intervals T3 and T4, which essentially overlap time intervals T1 and T2, respectively. As can be seen in FIG. 28, the system is capable of identifying viable heartbeats even in cases in which there are relatively large movements of the patient and/or the sensing electrode.

Figure 29:
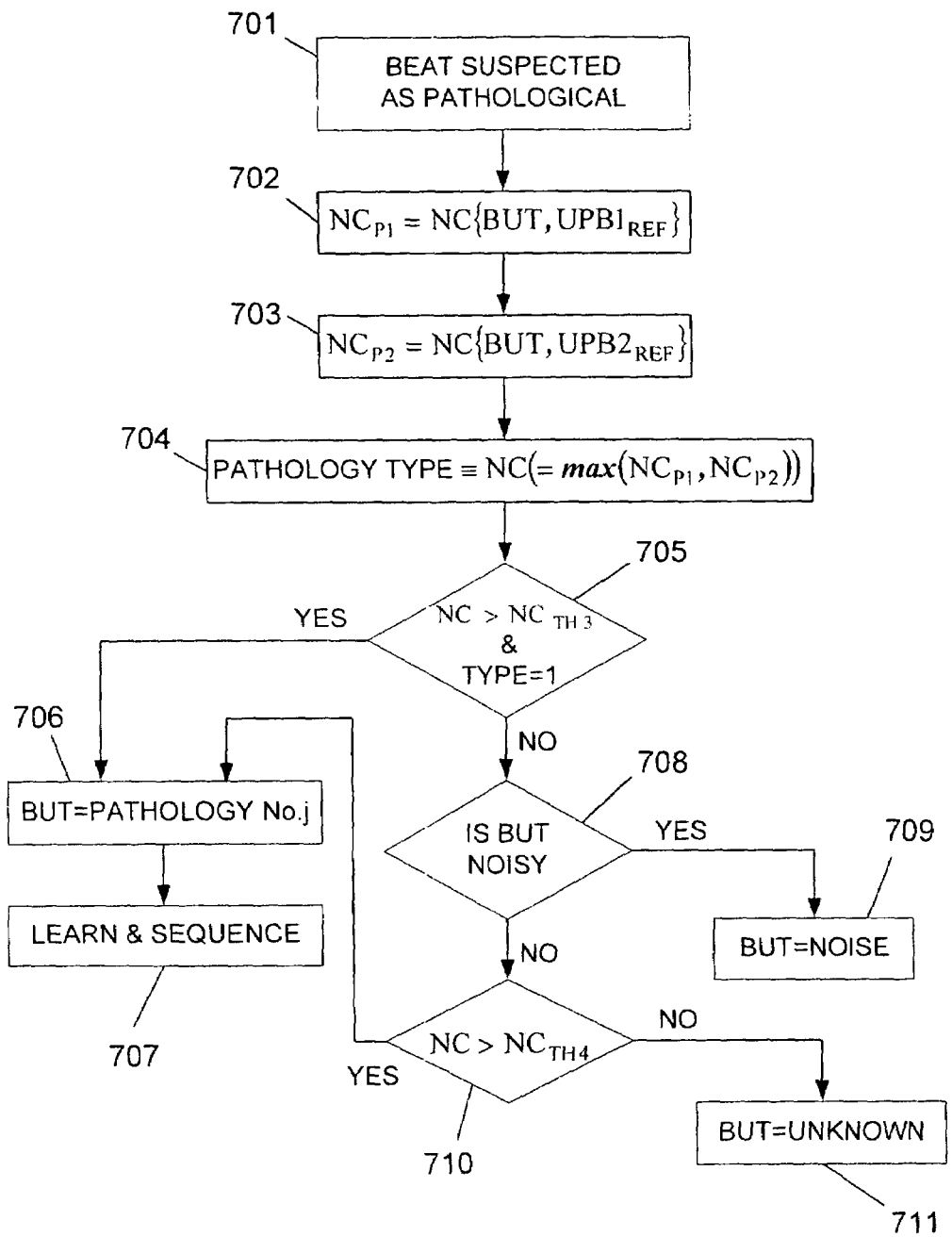
FIG. 29 schematically illustrates the pathological heartbeat first classification process, according to the preferred embodiment of the invention.

FIG. 29 schematically illustrates the pathological heartbeat first classification process, according to the preferred embodiment of the invention. Generally, there are two typical types of aberrant heartbeat patterns associated with common heart pathologies. These types of aberrant heartbeat patterns are represented by the Universal Pathological heartBeat No. 1 (UPB1) and the Universal Pathological heartBeat No. 2 (UPB2), and utilized by the system as reference templates. After deciding that a BUT is suspected as pathological (701) (see reference numeral 305 in FIG. 3), the system further examines it by comparing it to the UPHB1 (702) and to UPHB2 (703), and a first and a second Normalized Correlation (NC) values, i.e., $NC_{P1}$ and $NCP_2$, respectively, are calculated (702 and 703, respectively). The maximal NC value is chosen (704), which associates the BUT with the most probable corresponding pathological type of the BUT.

After a BUT is pathologically classified (706), it is utilized for updating the corresponding Universal Pathological heartBeat (UPB) reference template, to which the new BUTs are compared, by averaging the 'n' last known pathological heartbeats (of same type). The updated UPB reference template becomes the Patient-Specific Pathological Heartbeat (PSPHB) reference, since the system converges into (i.e. learns) the pathological patterns of the patient under examination.

Figure 23:
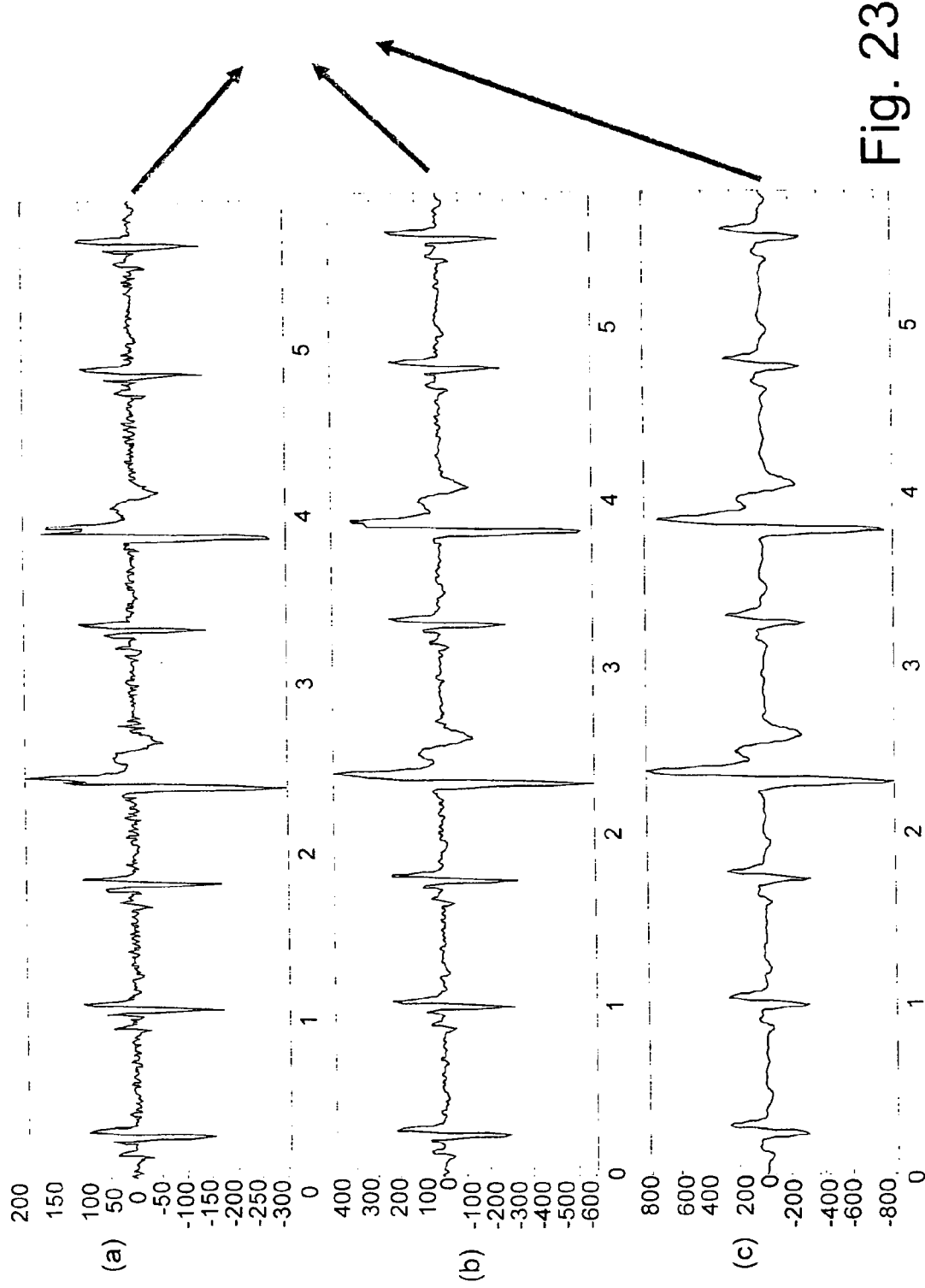
FIG. 23 illustrates R-peak detection by employing the Wavelet process on ECG signal, according to a preferred embodiment of the present invention.
Figure 23:
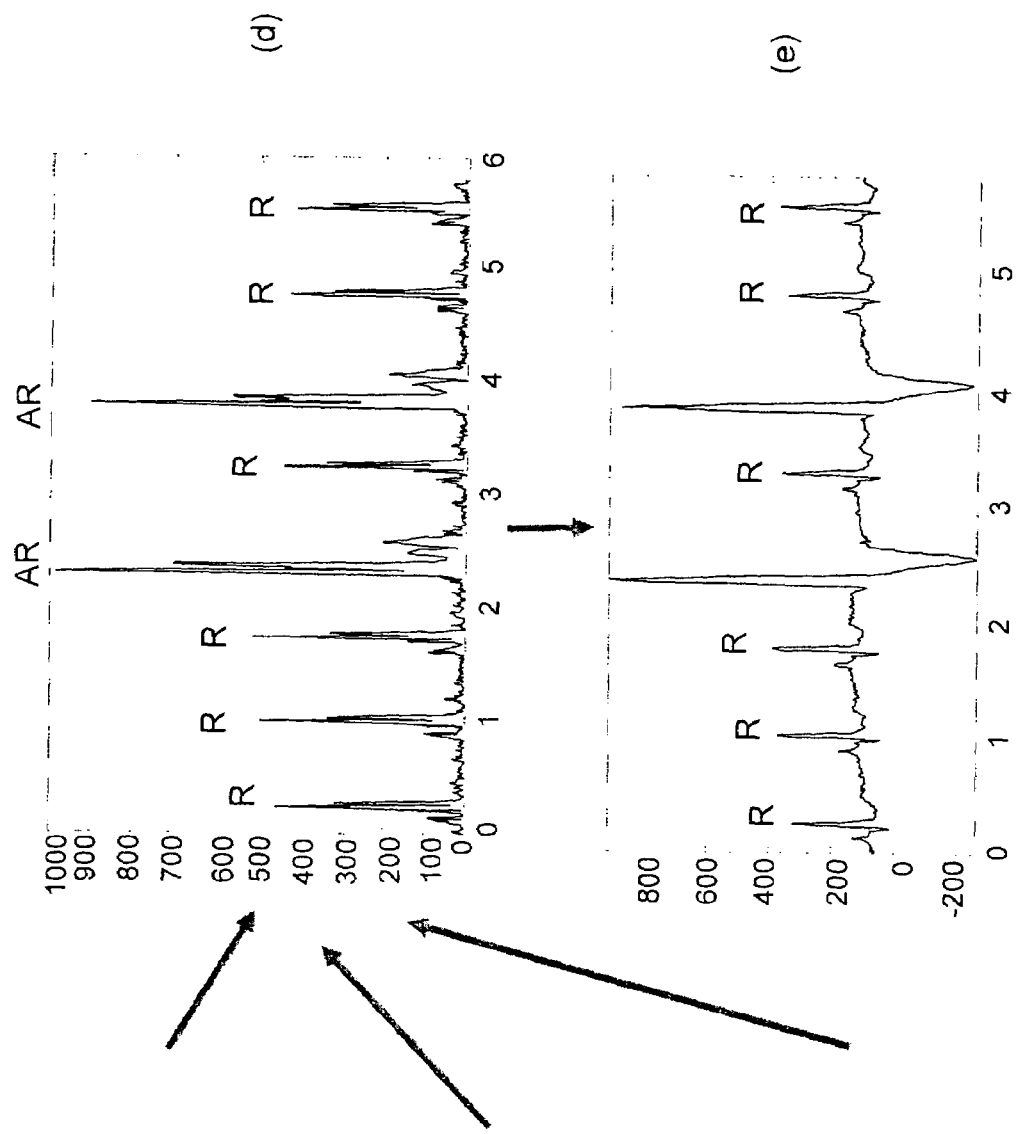

FIG. 23 illustrates R-peak detection by employing the Wavelet algorithm on ECG signal, according to a preferred embodiment of the present invention.

Figure 30:
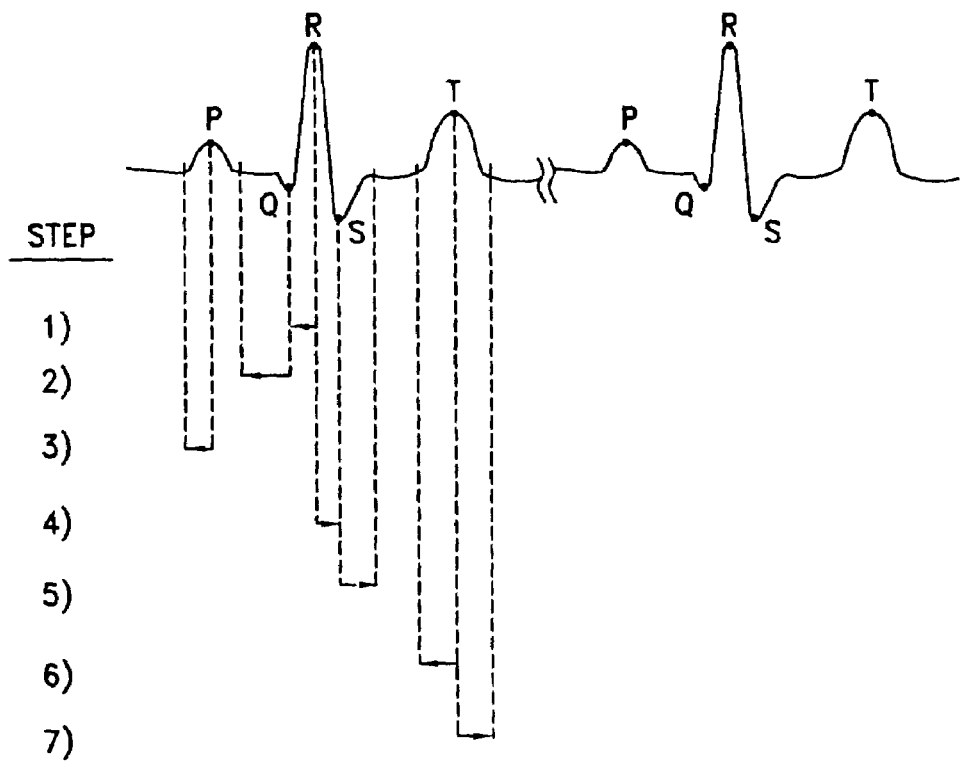
FIG. 30 schematically illustrates the segmentation process of Normal heartbeats, according to a preferred embodiment of the present invention.

FIG. 30 schematically illustrates the segmentation process of Normal heartbeats, according to a preferred embodiment of the present invention. The Wavelet Transfer Algorithm (WTA) is utilized for precise identification of the R-peak of each BUT. The WTA is also utilized for precise identification of the P-peak, T-peak, T(onset) and T(off) of each BUT. The system utilizes the R, P and T peaks for identifying also the P(onset), Q-peak, Q(onset), S-peak and S(off) of the BUT. In steps 1, 2 and 3, the system analyzes the section on the left-hand side of the (known) R-peak, for identifying the Q-peak, Q(onset) and P(onset). In steps 4, 5, 6 and 7, the system analyzes the sections on the right-hand side of the R-peak, for identifying the S-peak, S(off), T(onset) and T(end). Accordingly, the system identifies the QRS complex, ST-segment, QT-segment and the PR-segment of each BUT, provided that the BUT is identified as a viable heartbeat (as opposed to a BUT that is too deformed/distorted or noisy), which allow identification of heartbeat abnormalities other than the two commonly known Pathological heartbeat shapes.

Since the system's search for the above-described P, Q, R, S and T points is synchronized to the R—R interval (i.e., the duration between two consecutive R-peaks), it is clearly obvious that the segmentation process adapts itself to the heart-rate of the monitored patient.

Figure 31:
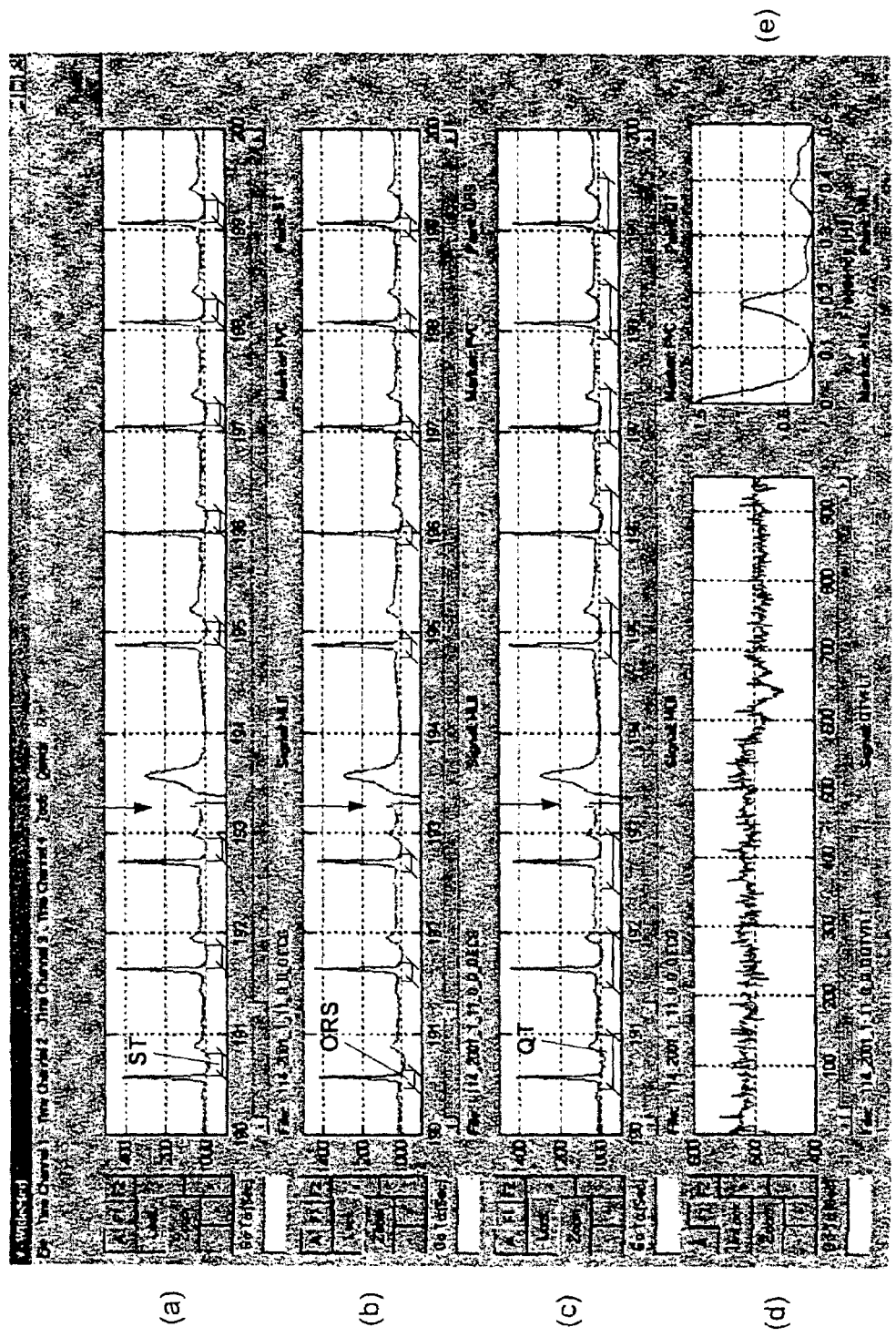
FIGS. 31a to 31e show test results that emphasize the various identified portions of Normal heartbeats, according to the preferred embodiment of the present invention.

FIGS. 31*a* to 31*e* show testing results that emphasize the various segments of Normal heartbeats, according to the preferred embodiment of the present invention. In FIG. 31*a*, the 'ST' segments are distinguished from the other segments by corresponding horizontal lines. Likewise, in FIG. 31*b*, the 'QRS' segments are distinguished from the other segments by corresponding horizontal lines, and in FIG. 31*c*, the 'QT' segments are distinguished from the other segments by corresponding horizontal lines. The latter segments were originally marked by red color, which is could not be visible in the figures. Therefore, the red color has been replaced by horizontal lines to indicate the corresponding segments. FIG. 31*d* shows the 'QTV' segments, and FIG. 31*e* shows the spectrum of the QTV segment. Pathological heartbeats are not segmented, as is shown in FIGS. 31*a*, 31*b* and 31*c*. As can be seen in FIGS. 31*a*, 31*b* and 31*c*, the pathological heartbeats is not segmented.

Figure 32:
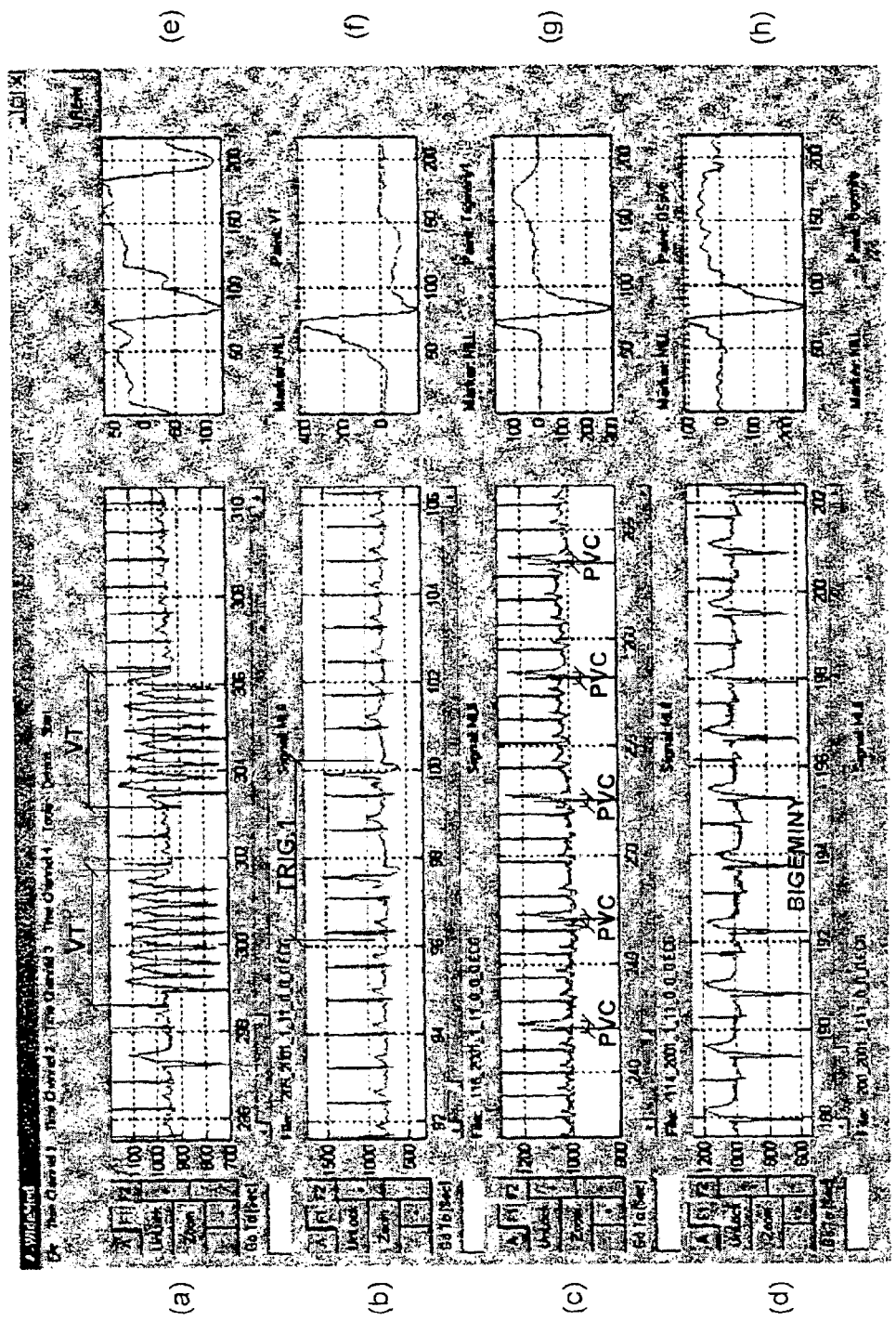
FIGS. 32a to 32h show exemplary test results that were obtained by monitoring four persons having different types of arrhythmias, according to the preferred embodiment of the present invention.

FIGS. 32*a* to 32*d* show testing results that were obtained by monitoring four persons having different types of pathological heartbeats, according to the preferred embodiment of the present invention. FIG. 32*a* shows 'VT' type pathological heartbeats that were taken from a first patient. FIG. 32*b* shows 'Trigeminy 1' type pathological heartbeats that were taken from a second patient. FIG. 32*c* shows isolated 'PVC' type pathological heartbeats that were taken from a third patient, and FIG. 32*d* shows 'Bigeminy' type pathological heartbeats that were taken from a third patient. The problematic heartbeats were originally marked by red color, which could not be visible in the figures. Therefore, the red color has been replaced by horizontal lines to indicate the corresponding segments to which the description refers.

FIGS. 32*e* to 32*h* show the different pathological heartbeats morphologies as detected by the system, per patient. For example, FIG. 32*e* shows a typical pathological heartbeat of 'patient (a)' (i.e. shown in FIG. 32*a*), which has been time-wise stretched in order to allow a close examination of its nature. Likewise, FIGS. 32f to 32h refer to patient (b), (c) and (d), respectively.

Figure 33:
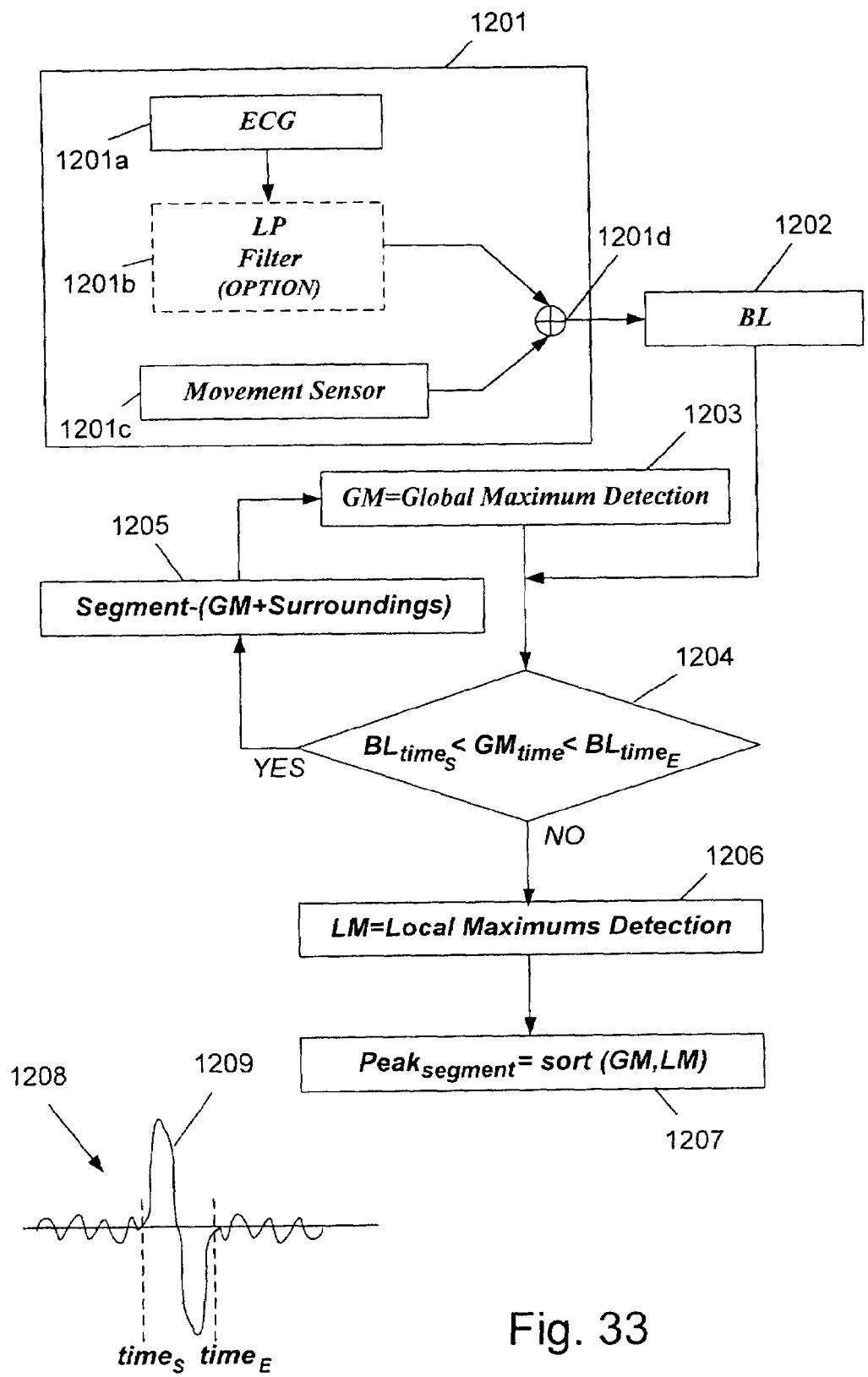
FIG. 33 schematically illustrates the process of detecting a large accidental peak that was superimposed on heartbeats, according to a preferred embodiment of the present invention.

FIG. 33 schematically illustrates the process of detecting a large accidental peak that was superimposed on heartbeats, according to a preferred embodiment of the present invention. As described before, the peaks of the R-waves are detected by employing the WTA on the ECG signal. However, the latter detection is based on using a global maximum (i.e. per ECG segment) as reference, which could lead to heartbeat misdetection if there is an artifact with relatively large peak in the analyzed ECG segment. Therefore, such artifacts must be identified and removed/discarded from the ECG segment. Numeral reference 1201 is the acquiring part of the system. The sampled ECG signal (1201a) is superimposed on a data peaked-up by movement sensor 1201c, in order to establish a Base-Line (BL) reference. Alternatively, at the absence of a movement sensor, the ECG signal is 'lowpass-filtered' (1201b), for obtaining the required BL reference signal (1208). In connection with BL signal (1202), a 'Local Maximum Peak' algorithm (1204) is utilized, for automatically detecting the most significant Local 'Maximum' peaks. Whenever a peak-point (not shown) is detected in the ECG signal (1201a), a corresponding movement (1209) is searched for in BL reference signal 1208. If such a movement is detected, the starting and ending instants of which being marked as $time_S$ and $time_E$ (in 1208), respectively, and the ECG peak 'falls' between said starting and ending instants, the corresponding ECG peak, together with its corresponding surroundings, is discarded and ignored (1205), because it is suspected as an artifact. The Local 'Maximum-peak' algorithm utilizes as a reference the Global Maximum of the entire new signal (1203), to which the local Maximum is compared. After discarding the artifact global maximum, the next global maximum is continued to be searched for within this segment, which is not suspected as artifact. Whenever such global maximum is found (i.e., that is not an artifact), it is utilized as a reference for the next ECG peaks. Nevertheless, the global maximums suspected as artifacts are saved, along with the rest of the local peaks, for later manipulations.

If several consecutive local maximums were found within an ECG segment, which were not suspected as artifacts (1206), the system refers to the largest maximum peak detected (i.e., within the ECG segment) as the global maximum for this particular ECG segment (1207).

Figure 34:
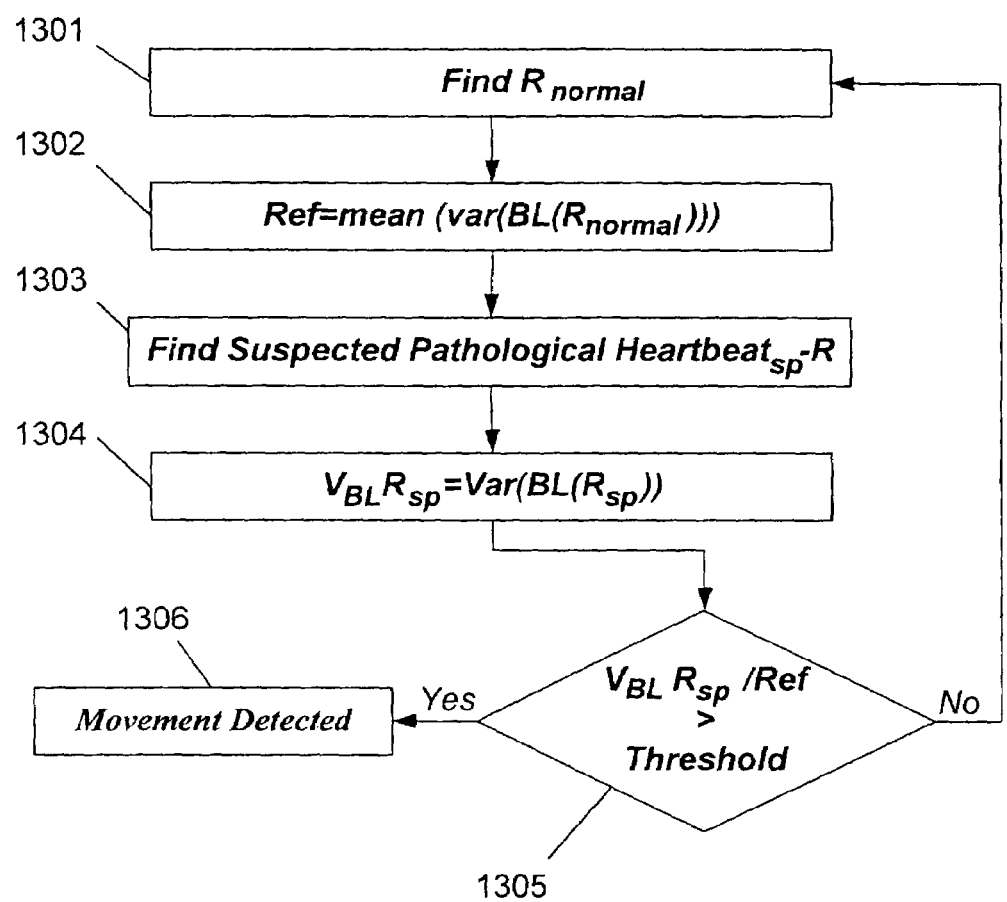
FIG. 34 schematically illustrates adaptive detection of low frequency movements that are superimposed on viable heartbeats, according to a preferred embodiment of the present invention.

FIG. 34 schematically illustrates adaptive detection of low frequency movements, according to a preferred embodiment of the present invention. The most problematic types of artifacts are those in the spectral range of the ECG signal, caused by patient movements, cable movements, etc. Artifacts having a frequency content that is similar to that of the actual ECG signal being recorded evidently can interfere with the correct interpretation of the ECG signal. In order to detect this type of artifacts, a base line is extracted from the ECG signal, which represents the status of the monitoring hardware and the inherent physiological/pathological status of the monitored person, and an adaptive algorithm is utilized for detecting changes in the base line.

The system finds the 'normal' R-peaks (1301), and since their magnitude is likely to vary in time, the variance is averaged and the mean value is used as a reference (1302). The adaptive movement detection checks if there is a change in the variance (1305) of the base line in the environment of a heartbeat that is suspected as pathological (1303), according to the reference that was calculated adaptively according to the environment of the normal heartbeats (1302). If the ratio between the current variance to Ref. (1302), is larger than a threshold value (1305), it indicates that a movement has been detected. Otherwise, the system continues to find R-peaks (1301) and to update the Ref. (1302).

Figure 35:
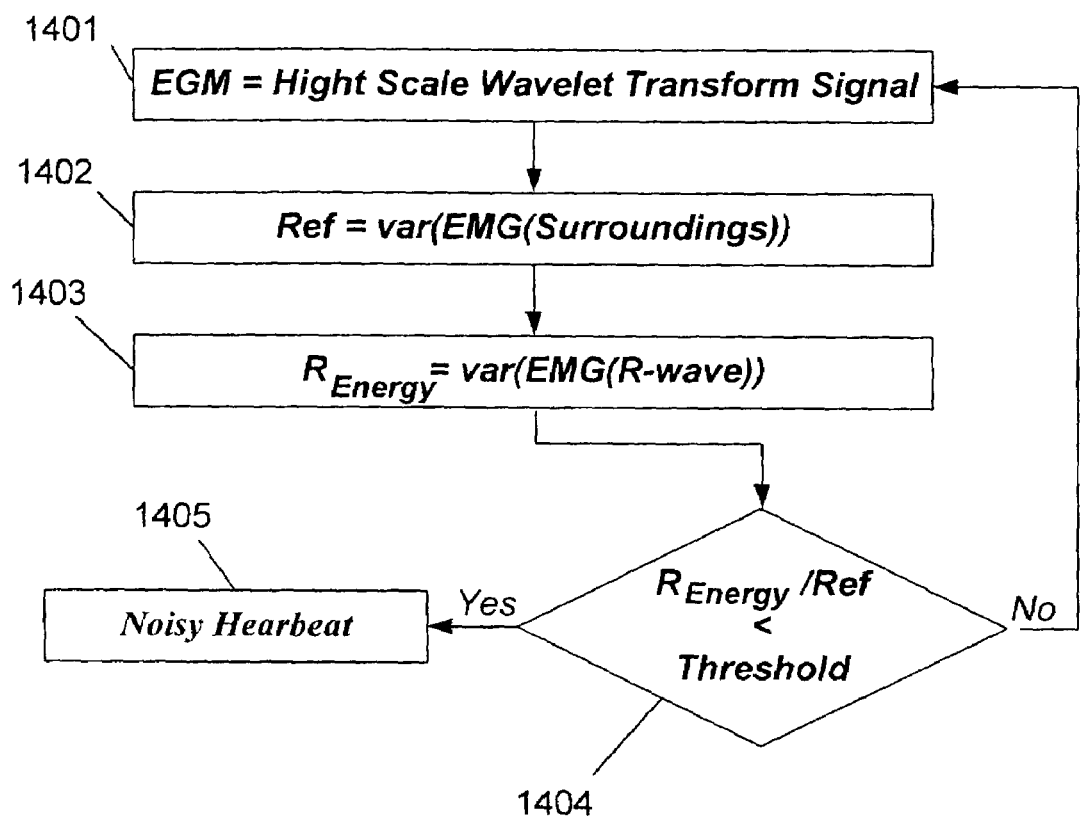
FIG. 35 schematically illustrates adaptive detection of high frequency EMG and noise signals that are superimposed on viable heartbeats, according to a preferred embodiment of the present invention.

FIG. 35 schematically illustrates adaptive detection of high frequency EMG and noise signals that are superimposed on viable heartbeats, according to a preferred embodiment of the present invention. This type of noise is characterized by having high frequency components caused by external noise and by muscle activity of the monitored person. In order to detect this type of noise, an adaptive detection algorithm was developed, which utilizes the high scale of the Wavelet Transform Algorithm (WTA) (1401). Using the WTA allows analyzing the energy of the surroundings of individual R-waves, and determining a corresponding Ref. (1402). Than, the energy of the R-wave is analyzed and a corresponding reference (i.e., $R_{Energy}$, 1403) is calculated. The ratio between the two references (i.e., $R_{Energy}$/Ref.) is calculated (1404), and if this ratio is larger than a threshold value, it indicates that the current heartbeat is noiseless (and the system continues by analyzing the next R, since in a noiseless heartbeat, as reflected in the ECG signal, the R-wave energy is much stronger than its surroundings. Otherwise, the current heartbeat is considered as noise (1405).

The analysis of the energies are analyzed, and the corresponding references (i.e., Ref. and $R_{Energy}$) recalculated, per R-wave and its surroundings, thereby allowing the system to respond very quickly to noises and EMG events, i.e., essentially immediately after their occurrences. The fast response, as described above, allows the system to utilize essentially every monitored heartbeat (i.e., BUTs) for enhancing the accuracy at which a person's cardiac condition is analyzed.

Respiratory

In connection with the Respiratory signals, the present invention utilizes Fuzzy Logic Decision Algorithm (FLDA), for obtaining more realistic decisions regarding the feasibility of Respiratory disorders.

A fuzzy logic based decision, associating Respiratory disorder with an obstructive apnea, hypoapnea, central apnea, mixed apnea and RERA, is made by the system after it considers data from at least the following data sources/channels: (1) EMG, (2) Limb movement, (3) Pressure Flow (PFlow), (4) Termistor Flow (TFlow), (5) CPAP/BPAP Flow (CFlow), (6) Chest effort, (7) Abdominal effort, (8) Blood saturation, (9) Hypnogram and (10) Arousal location.

In order to simplify the decision-making process, the ten data sources/channels have been grouped into five groups: (1) Flows, which includes the PFlow, TFlow and CFlow, (2) Effort, which includes the Chest Effort signal and the Abdominal Effort signal, (3) Movement, which includes the EMG signal and the Limb Movement signal, (4) Oxygen Saturation, which is measured by utilizing an Oximeter and (5) Sleep, which include the Hypnogram (sleep staging) and the arousal location signal. The system can differ automatically between sources the sources including sources 3 to 7 (Effort and Flow sources). The minimum sources for a full respiratory analysis are the Movement, Oxygen Saturation, Sleep, one of the Effort sources and one of the Flow sources. For a partial respiratory analysis (i.e., apnea without differing obstructive from central from mixed and without phase analysis), hypopnea, and RERA only one of the Effort or one of the Flow sources is needed in addition to the rest of the source groups. Corresponding algorithms have been developed for extracting relevant features from each of the above-described groups.

A normal breathing signal is characterized by having a low frequency signal, the frequency and magnitude of which are essentially constant. In this case, the envelope of this signal does not change with respect to time. A Respiratory Event is clinically defined as having the respiratory airflow decreasing by at least 30% from its initial value, for duration of at least 10 Seconds (a reference may be made to "Sleep Related Breathing Disorders in Adults: Recommendation for Syndrome Definition and Measurement Techniques in Clinical Research", The Report of an American Academy of Sleep Medicine Task Force. Sleep Vol. 22, No. 5, 1999 pp. 667–689).

Accordingly, in order to decide whether a Respiratory disorder is detected, the envelope of the effort signal is first analyzed, by carrying out the following steps:

(1) Detection and Smoothing of the Envelope (DSE) of the effort and flow signals. In order to produce the required envelope, the amplitude of each breathing cycle is identified, and the shape of the envelope of the breathing signal is 'smoothed' by utilizing a set of fuzzy logic rules, in order to remove irrelevant maximum points.

(2) Peak Detection and Maximum Setting (PDMS) of the envelope signal. After establishing the corresponding envelope signal, its maximal points are identified and utilized as time-wise boundaries for segmenting the effort signal into corresponding segments. If there is a group of at least two maximal points (i.e., in the envelope), which are too close (i.e., with respect to time) to one another, only the larger maximal point in that group is selected as time boundary. The identified time boundaries are also utilized for segmenting the envelope into segments that overlap the corresponding effort and flow signal segments.

(3) Segment Evaluation Process (SEP). Each segment (i.e., in the effort and flow signal) is evaluated for determining whether there is more than 30% decrease in the peak to peak and local maximum magnitude of the effort and flow signal contained within said segment. If there is a 30% and above decrease in said magnitude (i.e., for a duration larger than 10 seconds), a Fuzzy Logic Algorithm (FLA) is employed, for evaluating other relevant events, such as Oxygen de-saturation, arousal(s), movement(s), sleep staging (a reference may be made to "Fuzzy Sets and Fuzzy Logic Theory and Applications", G. J. Klir, Bo Yuan, Prentice Hall P T R, 1995).

However, if a decrease less than 30% is not evident in said magnitude, it is necessary to determine the 'direction' of the envelope of the evaluated segment, i.e., whether it tends Upwards (i.e., its time derivative is positive in each point of the corresponding envelope), Downwards (i.e., the envelope has negative time-derivative) or it maintains essentially the same magnitude. In order to determine the direction of each envelope's segment, a mathematical approximation to the envelope's segment is made by utilizing a Minimum Model Derived Distance algorithm in this case the model is a polynomial of second order (parabola). Then, mathematical manipulations are carried out for identifying the required corresponding time-derivatives of the corresponding parabola. Each envelope segment, which does not meet the '30% magnitude decrease' criteria, is assigned a corresponding parabola.

A Segment Combining Algorithm (SCA) is employed on segments that do not comply with the 30% of the EPA criteria in order to adjoin two adjacent segments to one (grand) segment. The SCA could be the Viterbi Algorithm— which will not be discussed, since it is known to those skilled in the art (Reference could be made to the web site -http://www.comp.leeds.ac.uk/scs-only/teaching-materials/HiddenMarkovModels/html_dev/viterbi_algorithm/s1_pg3.html)

Decision Making Algorithm (DMA). According to the present invention, the Respiratory system is characterized by employing a Fuzzy Logic for allowing the system to reach more realistic decisions regarding the nature of the Respiratory disorders. Accordingly, the DMA is based on a Fuzzy Logic Algorithm (FLA) (reference may be made to "Fuzzy Sets and Fuzzy Logic Theory and Applications", G. J. Klir, Bo Yuan, Prentice Hall P T R, 1995), which is utilized for estimating the probability of a Respiratory disorder detection and determine whether it is an apnea (another algorithm later described will determine whether it is an obstructive apnea, central apnea or mixed apnea), hypopnea or RERA while taking into account data from the above-described data sources/channels. The FLA gives mathematical interpretation to known clinical set of rules (according to which the known Chicago criteria and MEDICARE modifications to the Chicago criteria, and, thereby, allows the system to mimic the analysis process that is currently made manually by a clinician.

The FLA utilizes several trapezoid-shaped 'Probability-Wise Windows' (PWWs). Each PWW is associated with a corresponding event that is encountered in the corresponding data source selected from the group of data sources which are described hereinabove.

The term 'event' refers to noticeable change that is detected in the corresponding signal, such as sudden movements and/or exerted efforts. For example, in connection with the first data source, i.e., "(1) EMG", an event means that a rise in the EMG level has probably been detected. Each PWW has a duration that is relatively much larger (i.e. wider) than the duration of the corresponding event. In addition, each PWW comprises a positive slope portion (representing a gradual increase from 0.0 to 1.0 probability value), a 1.0 probability value portion and a negative slope portion (representing a gradual decrease from 1.0 back to 0.0 probability value).

The time duration of each part in each PWW has been optimized according to medical criteria, as well as its relative location (i.e., time-wise synchronization) of each PWW. For example, if the monitored person starts suffocating (i.e., the magnitude of the effort signal decreases by more than 30%), a corresponding delayed decrease in the Oxygen saturation level in the person's blood is expected to be observed. A normal delay (i.e., between suffocation and noticeable decrease in the Oxygen saturation level) is of a couple of seconds (e.g., 4–6 seconds). Accordingly, a first step will take place, according to which an Oxygen-related PWW will 'open' (i.e., placed) in a way that its (vertical) center is aligned with the ending point of the respiratory event. Then, a second step will take place, according to which the system analyzes the time location of the Oxygen event in relation to the Oxygen-related window. At the end of the latter analysis, the oxygen is assigned a probability value. For example, in an ideal hypopnea event, the delay between the Oxygen event and the suspected hypopnea event matches exactly the clinically predetermined delay, in which case the instant of the Oxygen event matches exactly the time center of the Oxygen-related PWW, in which case the Oxygen event is assigned the probability value 1.0. Accordingly, the probability that the suspected hypopnea is a 'real' hypopnea is 1.0. However, the delay may vary from one person to another and from one hypopnea to another, in which case the corresponding Oxygen event will be assigned a probability value other than 1.0. In some cases, the delay will be such that the Oxygen event will be timely located outside the Oxygen-related PWW, in which case it will be assigned the probability value 0.0. Accordingly, the suspected hypopnea will not be regarded as a 'real' hypopnea (i.e., the essential condition of a following decrease in the Oxygen saturation level—in the expected time window and time location—is not met).

Respiratory Event Classification

As described above the system detects a respiratory decrease of more than 30% and then determines if it is a respiratory event and identifies its type with the DMA. By analyzing the surroundings of the respiratory decrease in all the available sources (described above), the DMA grade the event by multiplying the grades that each event in each signal was given by the DMA. This grade, the decrease level by the maximum criteria and peak to peak criteria (described above) and if the present analyzed signal is a flow signal or an effort signal are the data for the respiratory event decision making layer to decide if the decrease is indeed a respiratory event and if it is an apnea, hypopnea or RERA. If the respiratory event was classified as apnea a Respiratory Pattern Recognition Algorithm (RPRA) is then performed on the apnea event to determine whether it is an obstructive apnea, a central apnea or mixed apnea.

Figure 45:
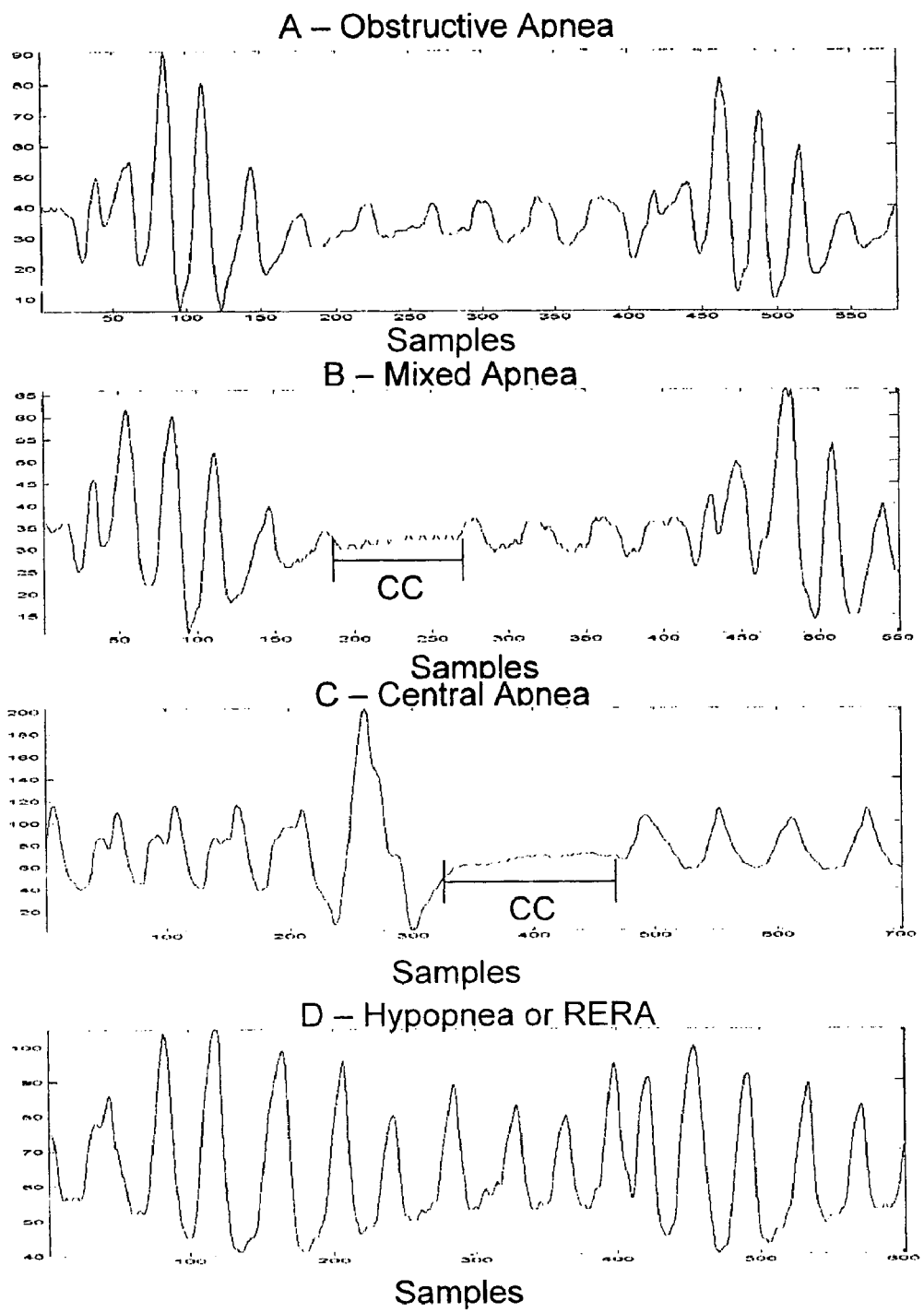
FIG. 45 depicts exemplary apnea events, according to the present invention.

An adaptive segmentation is preformed within the event boundaries in both effort channels in order to find a "Central Component" (CC), which is defined as an effortless period of time at least 2 seconds, characterized by a periodic line without viable effort (respiratory wavelets) noticeable. If a CC is detected, the RPRA checks whether the CC occupies most of the event duration, in which case the latter CC is classified as central apnea (see FIG. 45c). If the CC occupies a portion of the event, which precedes a decrease in the effort channel, which precedes a normal effort period, the CC is classified as mixed apnea (see FIG. 45b). If no CC is detected, the RPRA will classify the apnea event as obstructive apnea (see FIG. 45a).

Phase Detection Algorithm (PDA)

A change in the relative phase between the effort or flow signals or between effort and flow signals has clinical importance. The PDA performs the following steps:
a) Generating a signal that represents the phase between the two signals analyzed;
b) Whenever applicable, finding minima and maxima, the duration of which is 10 Seconds or more; and
c) Whenever applicable, finding adjoining events.

Movement Detecting Algorithm (MDA)

A movement is characterized by a noticeable increase in the signal energy. The task of the MDA is to allow distinguishing relatively large movements from the surrounding environment interference. The MDA performs the following steps:
a) Calculating the energy in overlapping windows with length L;
b) In each segment, finding the points with maximum values;
c) Calculating the normalized distance between each two of the points found in step (b); and
d) Finding the Maximal Normalized Distance (MND) in the normalized distances calculated in step (c).

Oxygen Saturation Event Algorithm (BSEA)

A blood saturation is defined as an 'event' whenever there is at least 4% decrease from the last steady level (according to MEDICARE modifications from the Chicago criteria were a blood saturation event is whenever there is 3% decrease from the last steady level). The BSEA performs the following steps:
a) Smoothing the signal with an averaging window of length L.
b) Finding local minima points in the smoothed signal.
c) Comparing the level of the minimum point to the level of the minimum's base.
d) Classifying events into one of two categories, according to a threshold level being lower than 4%: (1) events in which a magnitude decrease has been detected, which is less than the threshold, and (2) events in which a magnitude decrease has been detected, which is more than the threshold. Events associated with the second category are assigned a higher weight in the final decision making algorithm than the first category's events.

Respiratory Rate Signal Extraction

The system automatically extracts the Respiratory Rate signal (RR) and the Respiratory Rate Variability (RRV). This extraction may be implemented in two different ways:
a) Wavelet Transform RRV Extraction—like the R-wave detection in the ECG signal, the respiratory flow and effort signals are processed by a corresponding Wavelet algorithm, in order to obtain there from corresponding wavelet scales (the number of scales are determined according to the sampling rate), then the absolute values of the three highest scales are summed, thereby generating an absolute summation wavelet signal, in which the peaks are emphasized and easily detected. After detecting the peaks, the system detects the peak location on the source signal (effort or flow). The duration between two peaks is a sample in the RRV signal and 60/RRV is the sample rate of the RR signal. As with the ECG signal, not all the peaks will take part in the RRV and RR calculation. Using the prior knowledge of when each respiratory event ends and when there are movements, a noise cancellation algorithm will exclude peaks that are a consequence of artifacts.
b) Temporal RRV Extraction—using the maxima points detected to extract the envelope of the respiratory channels (described hereinabove), the respiratory peaks are detected. From this point, the same manipulations are preformed as with the Wavelet Transform RRV Extraction.

Flow Limitation

Figure 46:
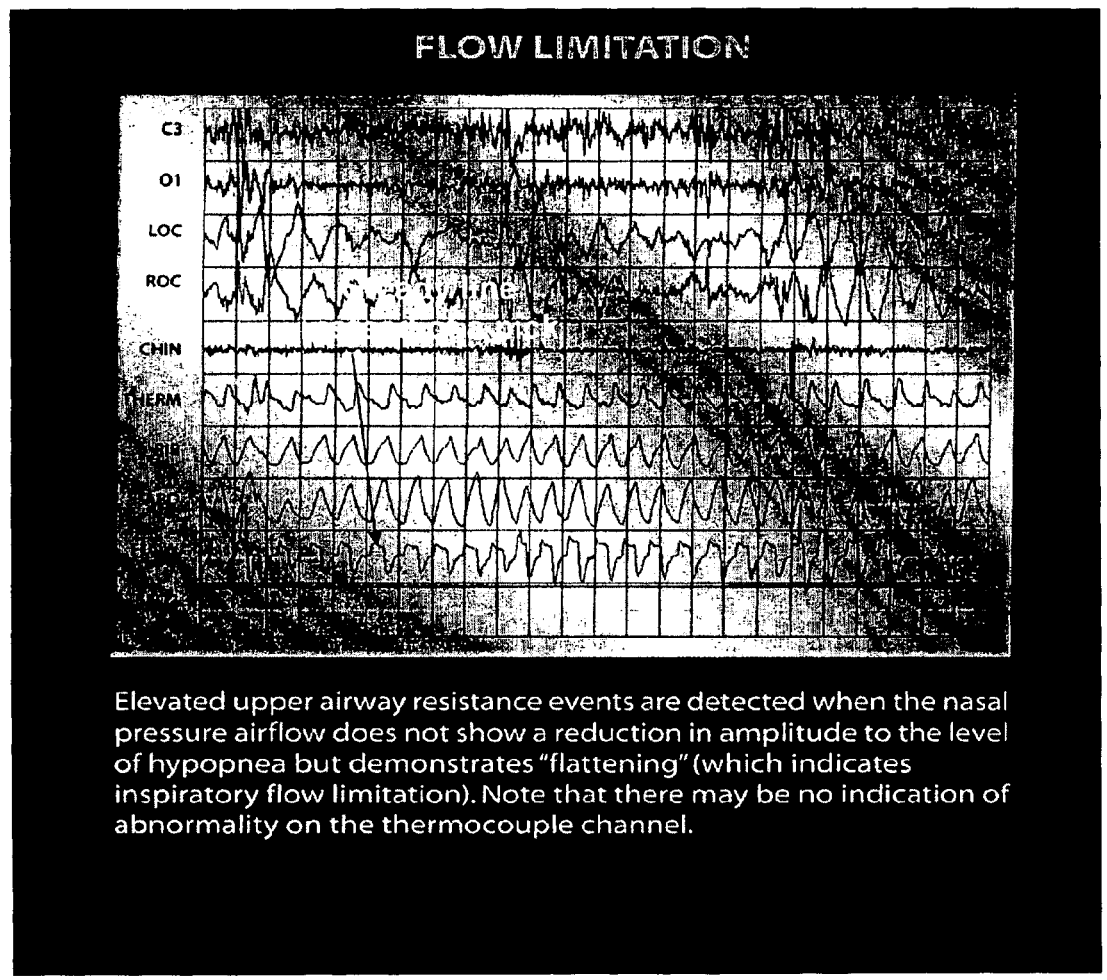
FIG. 46 depicts exemplary flow limitation.

Flow limitation is characterized by a steady line in the respiratory airflow (pressure sensor) signal wavelet instead of a peak (see FIG. 46).

To detect the flow limitation, respiratory peak detection is performed (one of the described peak detection algorithms in the Respiratory Rate Signal Extraction section). Once the peaks are detected, the system detects whether the peak is an absolute one in the separated respiration or it is part of a steady line in the central of the respiration, if it is then this respiration will be classified as a flow limitation.

Figure 36:
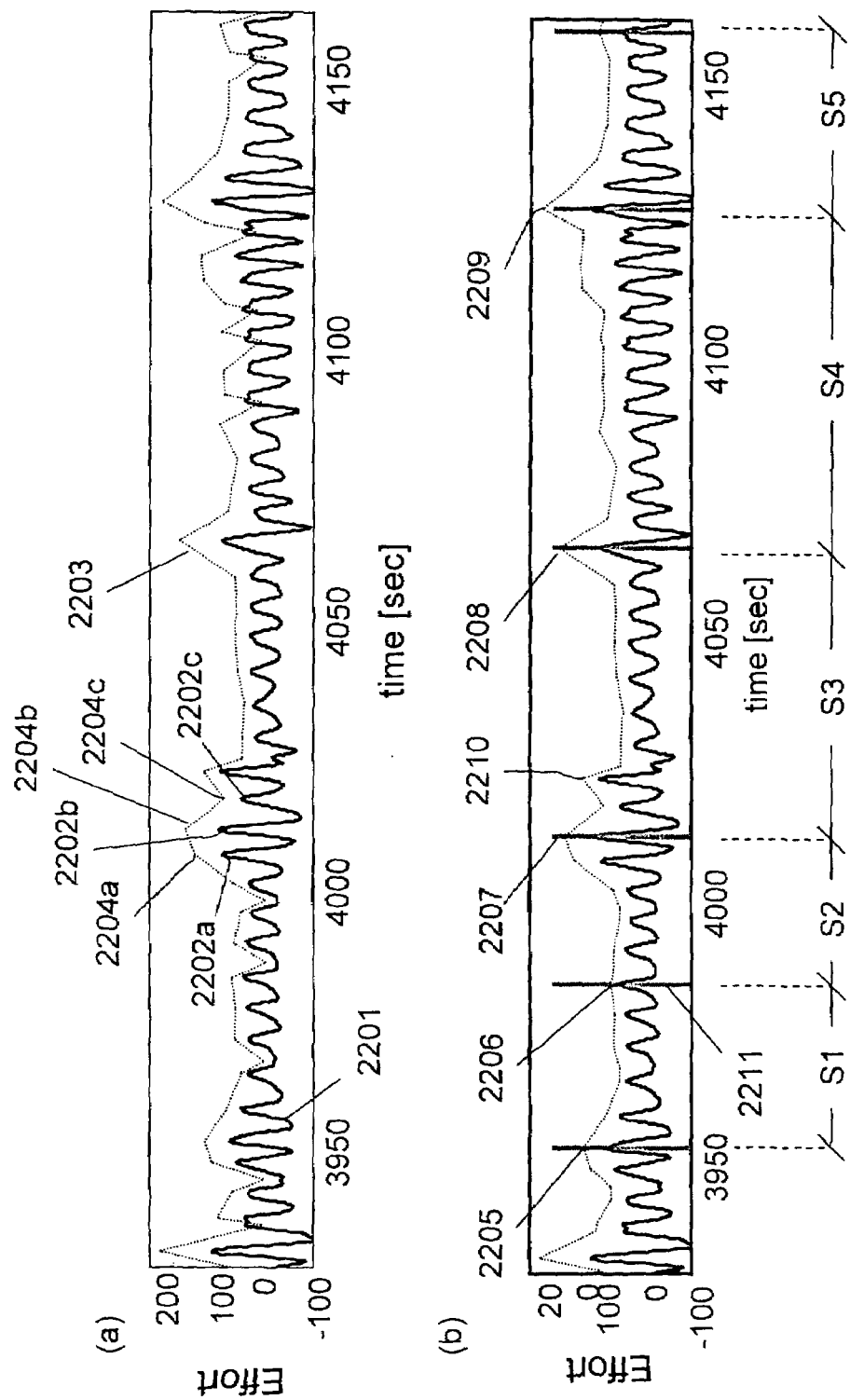
FIGS. 36a and 36b schematically illustrate envelope detection of Respiratory signal, according to the second embodiment of the invention.

FIGS. 36a and 36b are exemplary results showing the envelope of an effort signal and the corresponding segmentation of the effort signal, according to a preferred embodiment of the present invention. In FIG. 36a, the frequency and amplitude of effort signal 2201 change according to the Respiratory rhythm and the physiological/pathological status of the monitored person (not shown). Each peak-point in effort signal 2201 is identified, and its amplitude is represented by a corresponding point. For example, the peak-points 2202a, 2202b and 2202c are represented by Amplitude Points (APs) 2204a, 2204b and 2204c, respectively. Envelope 2203 comprises all the APs. The next step is smoothing the signal according to fuzzy logic rules and finding APs that are global maxima, after which their corresponding instants will be utilized as time-boundaries for segmenting effort signal 2203.

In FIG. 36b, APs 2205 to 2209 are global maxima and are indicated by corresponding vertical lines, such as line 2211. AP 2210 is also a global maximum. However, since it is too close (according to a certain criteria) to AP 2207 and smaller than AP 2207, it is not utilized as time-boundary. Accordingly, effort signal 2201 is segmented into segments S1 to S6, and each segment is evaluated.

FIG. 37 shows one exemplary segment of the effort signal, according to a preferred embodiment of the present invention. Segment 2300 is evaluated in order to decide whether it reflects a respiratory event. Accordingly, the magnitude of the mean value of points close to minimal point 2302 is compared to the magnitude of the mean value of points close to the magnitude of maximal point 2301, for evaluating the probability of a magnitude decrease of more than 30%. Another criteria is implemented, according to which it is decided whether the trend of the segment is Up, Down or Even (i.e., 'flat'). If the segment is flat, a corresponding PWW (not shown) is utilized by the FLA, for evaluating the correctness of the assumption e.g. if a respiratory event occurred.

Figure 38:
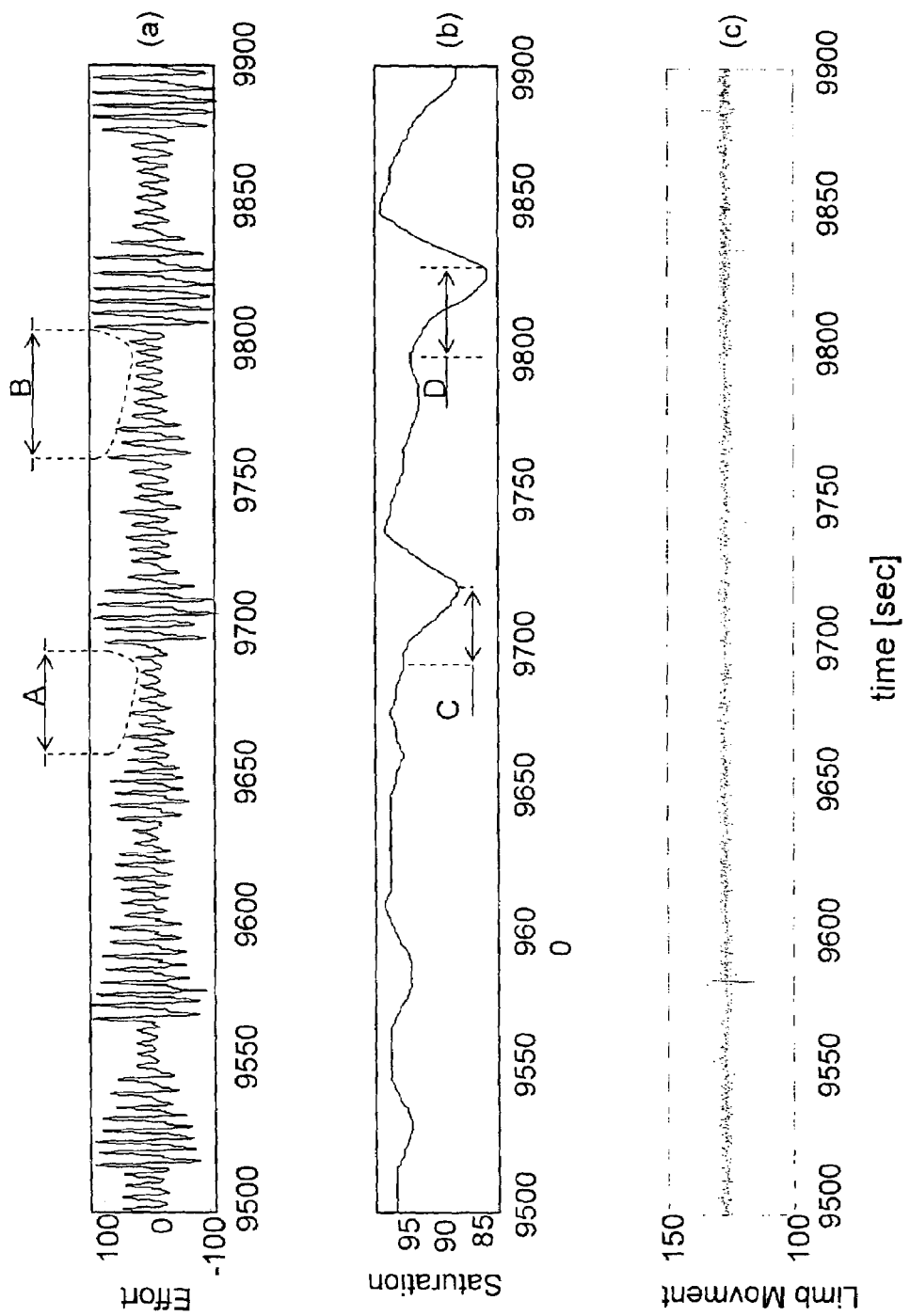
FIG. 38a and 38b illustrate apnea events and corresponding decrease in Oxygen saturation level, according to a preferred embodiment of the present invention.

FIGS. 38a and 38b show exemplary correlation between an effort signal that contains segments in which magnitude decrease of more than 30% and for duration of more than 10 seconds were detected, and Oxygen Saturation. As can be seen in FIG. 38a, significant Respiratory (i.e., effort) deterioration in, e.g., sections A and B (i.e., obstructive apneas) caused significant deterioration in the Oxygen Saturation, as reflected in sections C and D, respectively.

Figure 39:
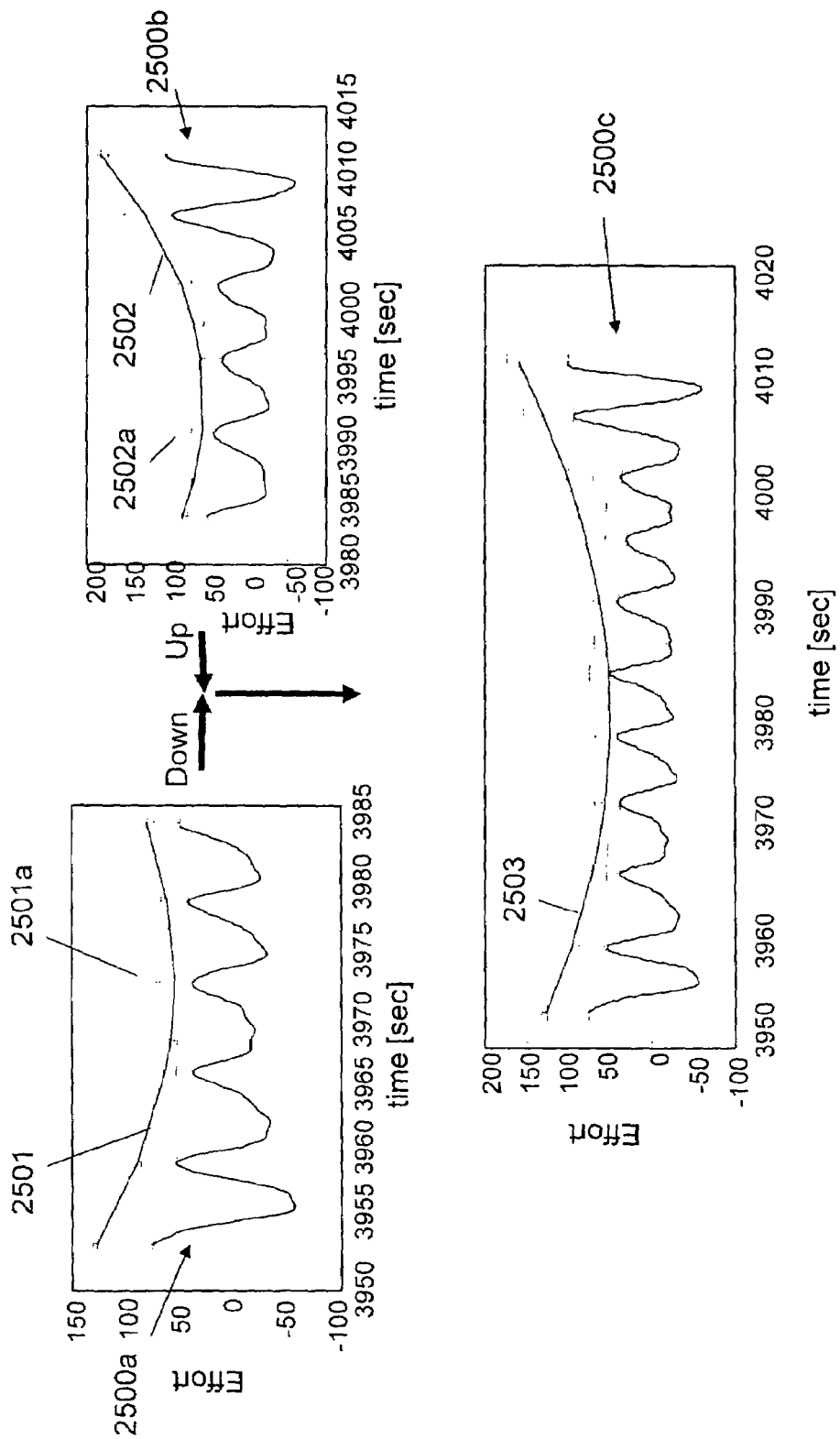
FIG. 39 illustrates adjoining Down parabola and Up parabola to one parabola, according to a preferred embodiment of the present invention.

FIG. 39 schematically illustrates adjoining Downwards-trend segments and Upwards-trend segments, according to a preferred embodiment of the present invention. After finding parabola 2501, which approximates the envelope of segment 2500a, and parabola 2502, which approximates the envelope of segment 2500b, the Segment Combining algorithm (SCA) is employed, after which a new segment 2500c is obtained. The 30% reduction feature is searched for in the new (grand) segment 2500c.

Figure 40:
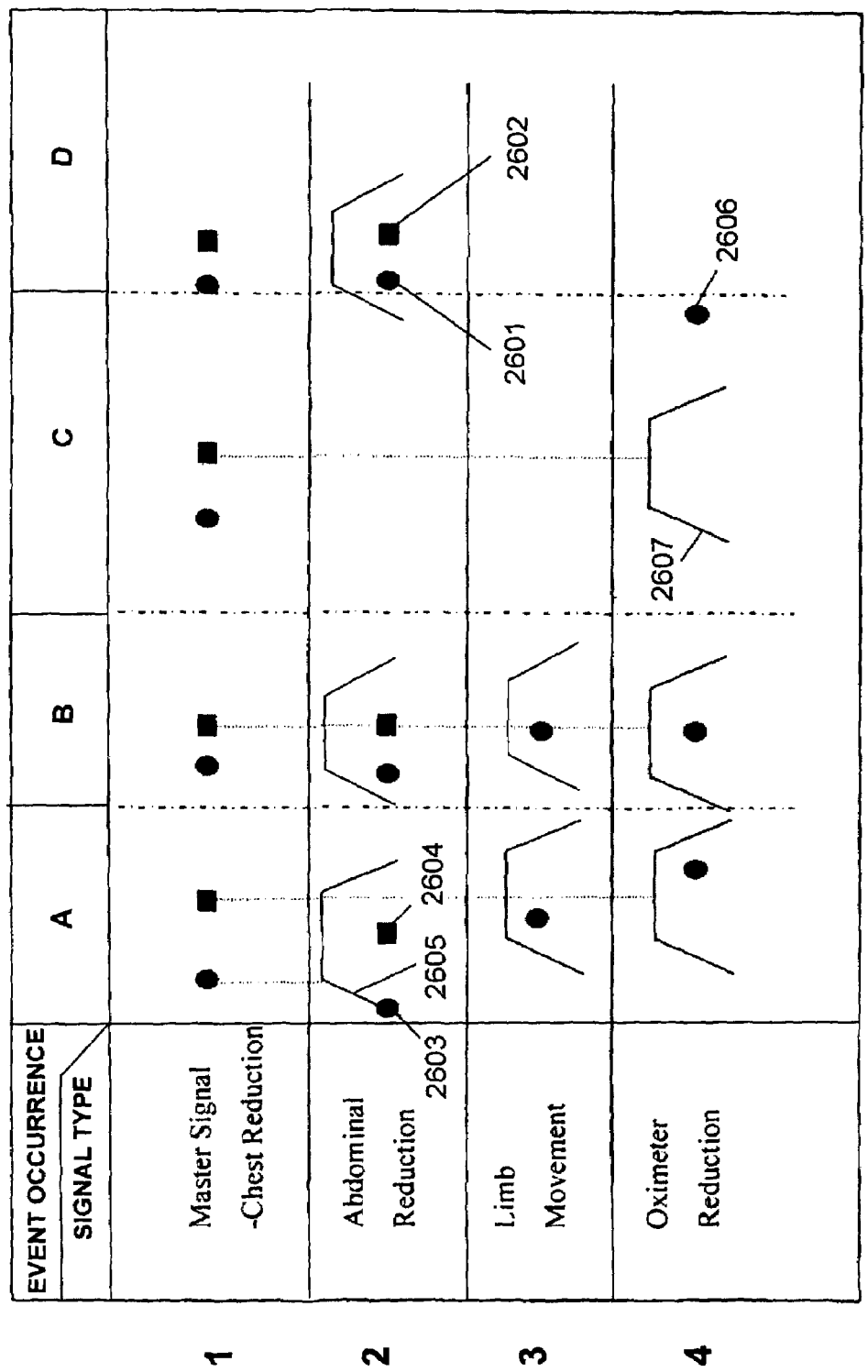
FIG. 40 schematically illustrates exemplary combinations of different events, on which the Decision-Making Process (DMA) is employed, according to a preferred embodiment of the present invention.

FIG. 40 schematically illustrates exemplary combinations of different events, on which the Decision-Making Algorithm (DMA) is employed, according to a preferred embodiment of the present invention. The chest signal reflects the effort signal. The mark '●' indicates the beginning of an event, and the mark '■' indicates its ending. In this example, four apnea events were identified, i.e., 1A, 1B, 1C and 1D. The duration (i.e., time between '●' and corresponding '■') of each of the apnea events 1A to 1D is random. Since a decrease in the abdominal effort is expected to overlap the chest effort, a PWW that is associated with the abdominal event is located in relation to the apnea event in a way that the '1.0 probability' (horizontal) line of the abdominal event starts and ends essentially at the starting point (i.e., ●) and ending point (i.e., '■') of the apnea, respectively. For example, the starting and ending points of abdominal event 2D (i.e., 2601 and 2602) essentially overlap the starting and ending points of chest event 1D, respectively. Accordingly, abdominal event 2D is assigned the largest weight (i.e., probability value 1). Abdominal event 2A is assigned a smaller weight, because its starting point 2603 is almost outside the limits of the PWW window 2605. Likewise, limb events 3A and 3B, Oximeter events 4A and 4B will be assigned the maximum weight.

Regarding chest event 1C, an Oximeter event 2606 has been detected. However, since it is completely outside PWW 2607, it is assigned a zero weight (value). Namely, Oximeter event 2606 can not be logically related to any other event. Consequently, Oximeter event 2606 is ignored and therefore all D event.

Figure 41:
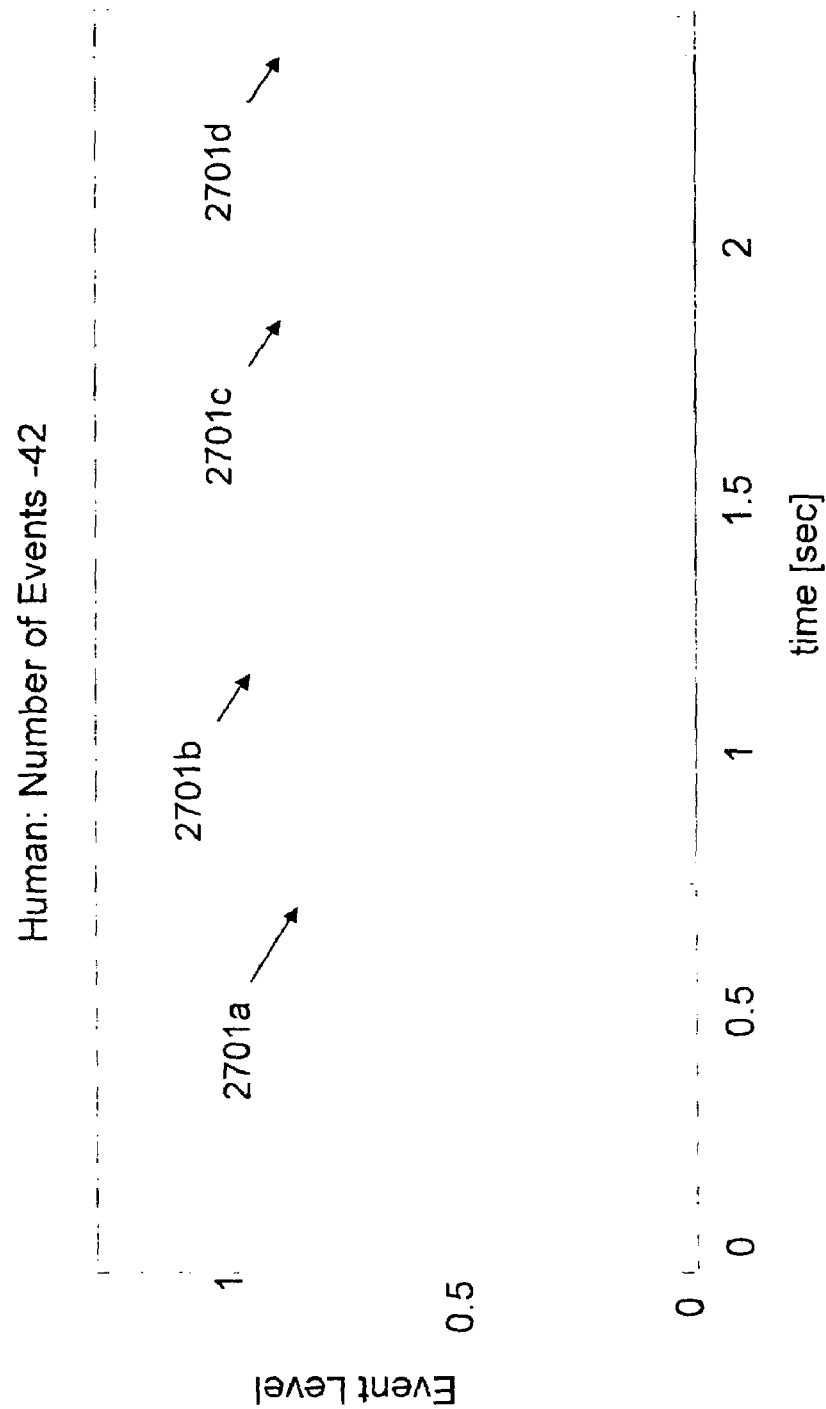
FIG. 41 illustrates exemplary resulting apnea events according to a human scorer.

FIG. 41 is a graph illustrating resulting apnea events according to manual scoring. Reference numerals 2701a to 2701d represent aggregations of apnea events. Because conventional systems are incapable of deciding the probability of occurrence of an apnea event, each event is assigned either a unity value or a zero value.

Figure 42:
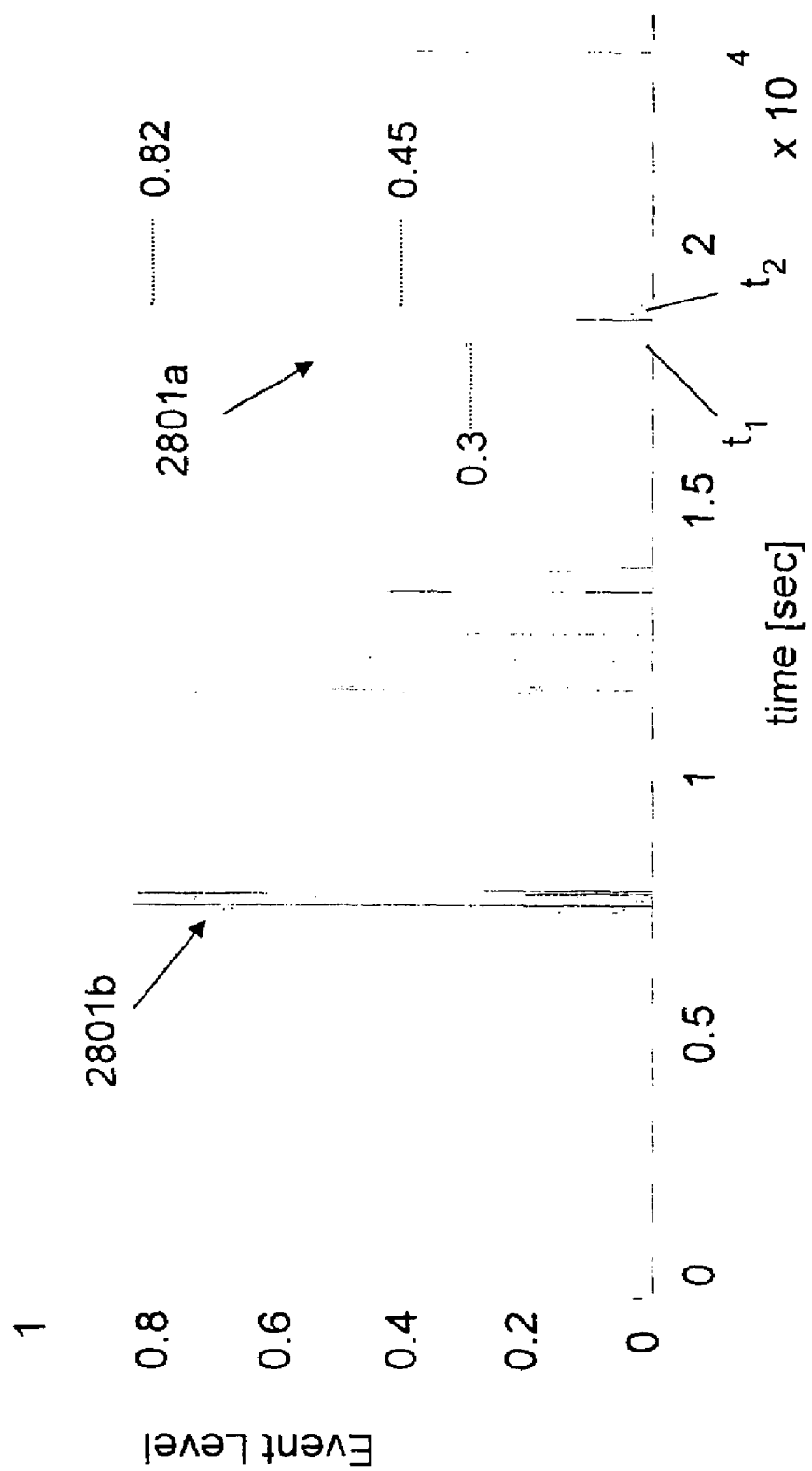
FIG. 42 illustrates exemplary resulting apnea events according to the present invention.
Figure 43:
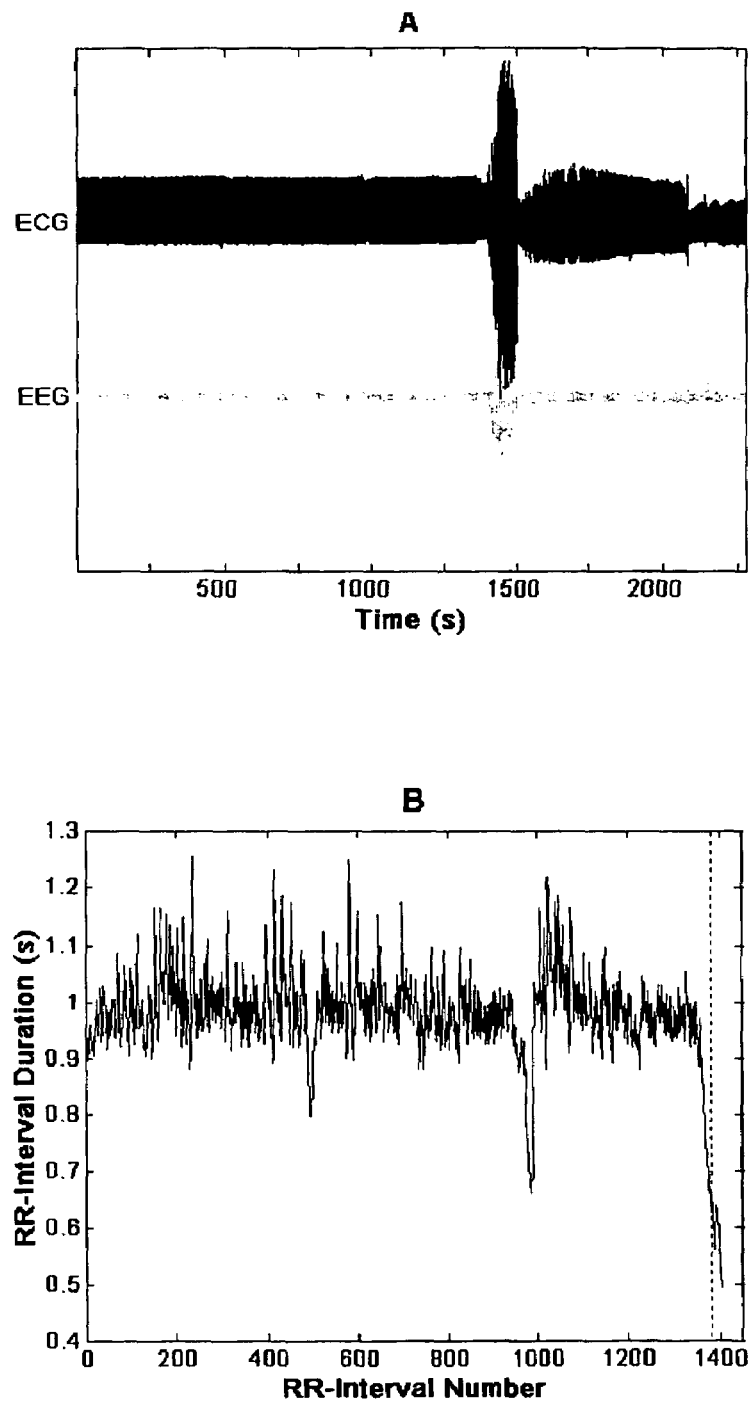
FIG. 43a depicts an exemplary ECG and left temporal EEG signals.
FIG. 43b depicts an RRI series which were extracted from the ECG record shown in FIG. 43A.

FIG. 42 is a graph illustrating resulting respiratory events, as affected by other factors, according to a preferred embodiment of the present invention. Reference numeral 2801a is an aggregation of several events that are suspected as hypopnea. In these aggregated events, additional two types of events were also considered in order to evaluate the probability of an event being an hypopnea. One type of these events is the Oxygen saturation level in the blood (i.e., as measured by the Oximeter channel), and the second type is the probability that the monitored person was sleeping (i.e., measured by the EEG signal). For example, at time t1 the resulting probability for an hypopnea is 0.3. A low-probability hypopnea may be obtained as a result of having: (1) very low probability value that the detected corresponding decrease in the Oxygen saturation level is associated with a hypopnea, and/or (2) very low probability value that the monitored person was fully asleep. At time t2, however, the resulting probability of an hypopnea is much higher (i.e., 0.82), because at that time the probability that the monitored person was sleeping was relatively high, and/or the corresponding decrease in Oxygen saturation level was more closely related to the event that was suspected as hypopnea.

Reference numeral 2801b refers to another aggregation of events. In these aggregated events, only one additional type of event was also considered in order to evaluate the probability of an event being a hypopnea, namely, the Oxygen saturation level in the blood. In general, in this aggregation, hypopnea events were assigned relatively high probability values.

In general, the more event types (e.g., Oxygen saturation, Sleep status) are considered when evaluating the probability of an hypopnea, the more 'realistic' is the decision regarding such hypopnea.

Of course, the features mentioned herein before for predicting physiological/pathological event or states are only illustrative, as future studies may teach new features that would contribute to, or enhance the, prediction process.

In addition, exemplary systems for forwarding aspects of medical data, as described herein, between several computerized stations, are illustrated in a former Patent of the present applicants (i.e., Patent application No. IL 147502).

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. Method for predicting changes of physiological/pathological states in a patient, based on sampling, processing and analyzing a plurality of aggregated noisy biomedical signals, comprising:
   a) generating a reference database of raw data streams or features, derived from said raw data streams, representing physiological/pathological states, by aggregating one or more raw data streams, each of which consisting of biomedical signals of a plurality of patients, at least several of which having one or more of said physiological/pathological states, wherein said features are obtained by performing, for each type of biomedical signal, adaptive segmentation of its corresponding raw data streams, and assigning, to each segment, individual attributes being represented by attribute values, thereby obtaining data related to each physiological/pathological states;

b) generating additional data streams using said attributes;

c) Repeating steps a), b) if needed;

d) determining an attribute domain, in which each segment being represented by a point that corresponds to the attribute values of said segment;

e) for each physiological/pathological state, generating a set of clusters in said attribute domain, each of which consisting of a combination of points determined by their relative location to other points, by assigning a set of property values to each point, each property value corresponding to the degree of association of said point with one of the clusters;

f) associating each point, in time, to a corresponding state;

g) determining the probabilities of transitions between states by obtaining the frequency and the order of appearance of each point, in time;

h) repeating steps d) to f) above while in each time, varying the combination of points included in each cluster according to their most updated property value and by including points derived from said probability until said updated property values remain essentially unchanged, thereby updating each cluster and said probabilities of transitions;

i) generating prior knowledge data, consisting of a plurality of feasible paths between states according to said probabilities of transitions, by associating each feasible path with a corresponding dynamics of transitions between physiological/pathological states;

j) associating at least one updated cluster with a normal/abnormal physiological state of said patient by using former knowledge, regarding normal/abnormal physiological/pathological states;

k) For each patient, l) aggregating one or more individual data streams or features, derived from said individual data streams, each of which consisting of biomedical signals of said patient, wherein said features are obtained by performing, for each type of biomedical signal, adaptive segmentation of its corresponding raw data streams, and assigning, to each segment, individual attributes being represented by attribute values;

m) Forming additional data streams out of said attributes;

n) Repetition of stages k), l) if needed;

o) assigning each individual attribute to a corresponding state, or to a new state, according to the probability to belong to each existing cluster or to a new cluster associated with said new or existing state and said probabilities of transitions;

p) adaptively updating each existing or new cluster and said probabilities of transitions according to said individual data streams;

q) obtaining a path, being an individual dynamics, between physiological/pathological states according to their order of appearance; and r) obtaining a prediction of being in, or transitions to, physiological/pathological states in said patient, by comparing said individual dynamics with known dynamics, obtained from prior knowledge.

2. A method according to claim 1, further comprising:

a) Whenever new individual attributes do not belong to an existing cluster, defining one or more new states and transition probabilities between existing states or new states;

b) Obtaining an updated path between said existing states or new states according to their order of appearance;

c) Associating said updated path with an updated individual dynamics of transitions between physiological/pathological states; and d) Obtaining an updated prediction of physiological/pathological states in said patient, according to said updated individual dynamics and the prior knowledge.

3. A method according to claim 1, further comprising:

Whenever the updated path is a new path reflecting transition between existing states:

a) associating said new path with a new individual dynamics of transitions between physiological/pathological states; and b) Obtaining a new prediction of physiological/pathological states in said patient, according to said new individual dynamics and the prior knowledge.

4. A method according to claims 2 or 3, further comprising Updating the reference database, the existing or new clusters, the transition probabilities between existing or new states, and the dynamics of transitions between existing or new physiological/pathological states.

5. A method according to claim 1, wherein the types of biomedical signals are selected from the group: EGG signal; EEG signal; Respiratory signal; EGG signals; Acoustic signals; Oximetry; Blood pressure; EMG; CO2; and Body movement/position.

6. Method according to claim 1, wherein the features are selected from the groups of:

Spectrum analysis features:
Zero crossing;
Estimated AR power spectrum;
Relative peak level of each frequency band;
Relative energy level of each frequency band;
Fundamental frequency;
Number of substantial frequencies; and
Membership level in each frequency group;

Temporal analysis features:
Maximum and minimum amplitude;
Maximum and minimum energy;
Number of substantial peaks;
Mean, variance and High order statistical moments;
Duration in seconds and in samples;
Transient level (derived from the adaptive segmentation algorithm);
Peak to peak maximum amplitude and duration;
First derivative (Slope);
Second derivative;
Wavelets coefficient calculation;
PCA coefficient calculation; and
Matching pursuit based segment decomposition;

Non-linear dynamics features:
The Lempel-Ziv complexity measure
Fractal dimension;
Lyapunov exponent; and
Density estimation of phase space derived features.

7. A method according to claim 5, wherein the adaptive segmentation of an ECG signal comprises:

a) generating several signals from the raw ECG signal, wherein in each signal a different frequency content being emphasized;
b) summating the corresponding absolute values of said signals;
c) filtering the resulting summation; and
d) employing local maxima detection method, for identifying the R-peaks, P-peaks and T-peaks in said filtered resulting summation, said R, P and T peaks being utilized for characterizing the corresponding heartBeats Under Test (BUTs), said P and T peaks being utilized also for further segmentation of heartbeats.

8. A method according to claim 7, wherein, obtaining features from an ECG signal comprises the steps:
a) detecting 'R—R' time-intervals between each two consecutive R-peaks; and
b) identifying characterizing points 'P', 'Q', 'S' and 'T' of the corresponding BUTs, by utilizing said 'R—R' time-intervals, at least some of said points being utilized for obtaining features related thereto.

9. A method according to claim 8, wherein identifying the R-peaks in the ECG signal is carried out by utilizing the Wavelet Transform Process with several scales associated with said R-peaks.

10. A method according to claim 8, wherein the features that are obtained from the ECG signal are:
a) The general shape of PQRST complex, which is obtained by utilizing pattern recognition technique, the Wavelets algorithm, and PCA;
b) Intervals, which relate to consecutive P, Q, R, S and T points of heartbeats;
c) Interval differences, which relate to differences of the intervals of b);
d) Interval ratios, which relate to ration between intervals of b);
e) Differentials of 'nth' order (n=1,2, . . . ) of consecutive intervals; and
f) Absolute values of the differentials mentioned in e).

11. A method according to claim 10, wherein the features of e) and f) are obtained with respect to:
(1) Single heartbeats; or
(2) Heartbeat ensemble averages, variance and RMS of differences; or
(3) Heartbeat ensemble distributions.

12. A method according to claim 1, wherein the adaptive segmentation of an all physiological and derived signals comprises utilization of a first and a second time-windows, the time-width and relative location being varied until a decision, regarding the optimized location of the boundaries of each EEG segment, is determined, based on the comparison between the statistical properties of a first signal portion contained in the first time-window to the statistical properties of a second signal portion contained in the second time-window.

13. A method according to claim 12, wherein the comparison is implemented using the Generalized Likelihood Ratio Test (GLRT) and KullBack Leibler Divergence (KLD) measures.

14. A method according to claim 5, wherein the adaptive segmentation of the Respiratory signal comprises:
a) Detection and Smoothing of the envelope of a corresponding chest and abdomen effort signals, air pressure flow signal, and thermistor flow signal;
b) Peak Detection and Maximum Setting of the envelope signal; and
c) Identifying two consecutive global maxima points, said points defining the temporal boundaries of a corresponding segment of said envelope.

15. A method according to claim 5, wherein features that are obtained from acoustic signals are related to spectral features and peak velocities, which are obtained from beat-induced intra-cardiac sounds and Doppler-shift effect of intra-vascular (coronary) blood flow, respectively.

16. A method according to claim 1, wherein the set of clusters is generated by employing un-supervised fuzzy clustering algorithm on the points residing within the corresponding attribute domain.

17. A method according to claim 1, wherein the classification of the extracted features is implemented by utilization of one or more Hidden Markov Models (HMM) models, each of which could be characterized by having different number of states and free parameters.

18. A method according to claim 17, wherein different HMM models are trained to characterize different global physiological/pathological behavior, which may be associated with specific group of population, sleep stage or any health condition.

19. A method according to claim 17 or 18, wherein the prediction process utilizes one or more HMM models and one or more sets of fuzzy logic rules that are employed on the factors/features: (1) pathological heartbeats, (2) patient's weight or height or general health/condition, (3) blood pressure, (4) sleep stage, and (5) oxygen in the blood, in order to obtain a more reliable prediction result.

20. A method according to claims 17 or 18, wherein different mixtures of HMM models are utilized, each of which is optimal with respect to different monitoring stage, time epoch and biomedical signal.

21. A method according to claim 1, further comprising:
Generating, in real-time, alert indications representing abnormal physiological events;
and Automatically transmitting said indications to a physician over a data network, for determining/providing the required medical treatment.

22. A method according to claim 1, further comprising dynamically controlling the operation of a medical apparatus used for providing medical treatment to a patient being monitored, in response to identified pre-pathological state(s) in said patient, for preventing the occurrence of the pathological state(s).

23. A method according to claim 22, wherein the medical apparatus is an apparatus that is selected from the following group of apparatuses, or an apparatus operable using combined principles of several of these apparatuses:
Controllable drug dosage devices;
Controllable gas/air delivery devices;
Continuous Positive Airway Pressure (CPAP);
Bi-level positive airway pressure (BPAP);
Implantable/non-implantable Respiratory Stimulator;
Implantable/non-implantable Brain/Nerve Stimulator/Pacers;
Implantable/non-implantable cardiac defibrillators (ICD)/cardiac pacers/Cardiac Resynchronization Therapy (CRT).

24. System for predicting changes of physiological/pathological states in a patient, based on sampling, processing and analyzing a plurality of aggregated noisy biomedical signals, comprising:
a) Data acquisition means for collecting biomedical signals of one or more patients;
b) A database of data streams or features, derived from said data streams, representing physiological/pathological states, said database aggregates one or more raw data streams, each of which consisting of said biomedical signals of a plurality of patients, at least several of which having one or more of said physiological/pathological states, said database being capable of storing data streams or features which are used as reference data streams or features for characterizing further individual patients and for storing data streams or features of individual patients;

c) First processing means for obtaining said features by performing, for each type of biomedical signal, adaptive segmentation of its corresponding raw data streams, and assigning, to each segment, individual attributes being represented by attribute values, and for obtaining data related to each physiological/pathological states; and d) Second processing means for determining an attribute domain, in which each segment being represented by a point that corresponds to the attribute values of said segment; for generating a set of clusters in said attribute domain for each physiological/pathological state wherein each of which consisting of a combination of points determined by their relative location to other points, for assigning a set of property values to each point, wherein each property value corresponding to the degree of association of said point with one of the clusters; for associating each point, in time, to a corresponding state; for determining the probabilities of transitions between states by obtaining the frequency and the order of appearance of each point, in time; for varying the combination of points included in each cluster according to their most updated property value and for including points derived from said probability until said updated property values remain essentially unchanged, so as to update each cluster and said probabilities of transitions; for generating prior knowledge data, consisting of a plurality of feasible paths between states according to said probabilities of transitions, by, and for associating each feasible path with a corresponding dynamics of transitions between physiological/pathological states; for associating at least one updated cluster with a normal/abnormal physiological state of said patient by using former knowledge, regarding normal/abnormal physiological/pathological states; for performing, for each type of biomedical signal, adaptive segmentation of its corresponding raw data streams, and for assigning, to each segment, individual attributes being represented by attribute values, for assigning each individual attribute to a corresponding state, or to a new state, according to the probability to belong to each existing cluster or to a new cluster associated with said new or existing state and said probabilities of transitions; for adaptively updating each existing or new cluster and said probabilities of transitions according to said individual data streams; for obtaining a path, being an individual dynamics, between physiological/pathological states according to their order of appearance, and associating said most feasible path with an individual dynamics of transitions between physiological/pathological states; and for obtaining a prediction of being in, or transitions to, physiological/pathological states in said patient, by comparing said individual dynamics with known dynamics, obtained from prior knowledge.

25. System according to claim 24, further comprising third processing means for defining one or more new states and transition probabilities between existing states or new states whenever new individual attributes do not belong to an existing cluster; obtaining an updated path between said existing states or new states according to their order of appearance; for associating said updated path with an updated individual dynamics of transitions between physiological/pathological states; and for obtaining an updated prediction of physiological/pathological states in said patient, according to said updated individual dynamics and the prior knowledge.

26. System according to claim 24, further comprising fourth processing means for associating the new path with a new individual dynamics of transitions between physiological/pathological states; and for obtaining a new prediction of physiological/pathological states in said patient, according to said new individual dynamics and the prior knowledge, whenever the updated path is a new path reflecting transition between existing states.

27. System according claims 25 or 26, further comprising fifth processing means for updating the reference database, the existing or new clusters, the transition probabilities between existing or new states, and the dynamics of transitions between existing or new physiological/pathological states.

28. System according to claim 24, in which the types of biomedical signals are selected from the group:
 ECG signal;
 EEG signal;
 Respiratory signal;
 EOG signals;
 Acoustic signals;
 Oximetry; and
 Blood pressure;
 EMG;
 CO2; and
 Body movement/position.

29. System according to claim 24, in which the features are selected from the groups of:
 Spectrum analysis features:
  Zero crossing;
  Estimated AR power spectrum;
  Relative peak level of each frequency band;
  Relative energy level of each frequency band;
  Fundamental frequency;
  Number of substantial frequencies; and
  Membership level in each frequency group;
 Temporal analysis features:
  Maximum and minimum amplitude;
  Maximum and minimum energy;
  Number of substantial peaks;
  Mean, variance and skewness;
  Duration in seconds and in samples;
  Transient level (derived from the adaptive segmentation algorithm);
  Peak to peak maximum amplitude and duration
  First derivative (Slope);
  Second derivative;
  Wavelets coefficient calculation;
  PCA coefficient calculation; and
  Matching pursuit based segment decomposition;
 Non-linear dynamics features:
  The Lempel-Ziv complexity measure
  Fractal dimension;
  Lyapunov exponent; and
  Density estimation of phase space derived features.

30. System according to claim 28, in which the adaptive segmentation of an ECG signal comprises:

a) Circuitry for generating several signals from the raw ECG signal, wherein in each signal a different frequency content being emphasized;
b) Circuitry for summating the corresponding absolute values of said signals;
c) Circuitry for filtering the resulting summation; and
d) Sixth Processing means for identifying the R-peaks, P-peaks and T-peaks in said filtered resulting summation, said R, P and T peaks being utilized for characterizing the corresponding heart Beats Under Test (BUTs), said P and T peaks being utilized also for further segmentation of heartbeats, by employing local maxima detection method.

31. System according to claim 30, comprising seventh processing means for obtaining features from an ECG signal, by detecting 'R—R' time-intervals between each two consecutive R-peaks; and identifying characterizing points 'P', 'Q', 'S' and 'T' of the corresponding BUTs, by utilizing said 'R—R' time-intervals, at least some of said points being utilized for obtaining features related thereto.

32. System according to claim 31, comprising eighth processing means for identifying the R-peaks in the ECG signal by utilizing the Wavelet Transform Process with several scales associated with said R-peaks.

33. System according to claim 31, in which the features that are obtained from the ECG signal are:
a) The general shape of PQRST complex, which is obtained by utilizing pattern recognition technique, the Wavelets algorithm, and PCA;
b) Intervals, which relate to consecutive P, Q, R, S and T points of heartbeats;
c) Interval differences, which relate to differences of the intervals of b);
d) Interval ratios, which relate to ration between intervals of b);
e) Differentials of 'nth' order (n=1,2, . . . ) of consecutive intervals; and
f) Absolute values of the differentials mentioned in e).

34. System according to claim 33, in which the Differentials of 'nth' order (n=1,2, . . . ) of consecutive intervals and the absolute values of said differentials are obtained with respect to:
a) Single heartbeats; or
b) Heartbeat ensemble averages, variance and RMS of differences; or
c) Heartbeat ensemble distributions.

35. System according to claim 28, in which the adaptive segmentation of an EEG signals comprises utilization of a first and a second time-windows, the time-width and relative location being varied until a decision, regarding the optimized location of the boundaries of each EEG segment, is determined, based on the comparison between the statistical properties of a first EEG signal portion contained in the first time-window to the statistical properties of a second EEG signal portion contained in the second time-window.

36. System according to claim 35, in which the comparison is implemented using the GLRT and KLD measures.

37. System according to claim 28, comprising processing means for adaptive segmentation of the Respiratory signal by detection and Smoothing of the envelope of a corresponding chest effort, abdomen effort signals, air pressure flow signal, and thermistor flow signal; Peak Detection and Maximum Setting of the envelope signal; and identifying two consecutive global maxima points, said points defining the temporal boundaries of a corresponding segment of said envelope.

38. System according to claim 28, in which features that are obtained from acoustic signals are related to spectral features and peak velocities, which are obtained from beat-induced intra-cardiac sounds and Doppler-shift effect of intra-vascular (coronary) blood flow, respectively.

39. System according to claim 24, in which the set of clusters is generated by employing un-supervised fuzzy clustering algorithm on the points residing within the corresponding attribute domain.

40. System according to claim 24, in which the classification of the extracted features is implemented by utilization of one or more HMM models, each of which could be characterized by having different number of states and free parameters.

41. System according to claim 40, in which different HMM models are trained to characterize different global physiological/pathological behavior, which may be associated with specific group of population, sleep stage or any health condition.

42. System according to claim 40 or 41, in which the prediction process utilizes one or more HMM models and one or more sets of fuzzy logic rules that are employed on the factors: (1) pathological heartbeats, (2) patient's weight or height or general health/condition, (3) blood pressure, (4) sleep stage, and (5) oxygen in the blood, in order to obtain a more reliable prediction result.

43. System according to claims 40 or 41, in which different mixtures of HMM models are utilized, each of which is optimal with respect to different monitoring stage, time epoch and biomedical signal.

44. System according to claim 24, further comprising ninth processing means for generating, in real-time, alert indications representing abnormal physiological events; and for automatically transmitting said indications to a physician over a data network, for determining/providing the required medical treatment.

45. System according to claim 24, further comprising tenth processing means for dynamically controlling the operation of a medical apparatus used for providing medical treatment to a patient being monitored, in response to identified pre-pathological state(s) in said patient, for preventing the occurrence of the pathological state(s).

46. System according to claim 45, in which the medical apparatus is an apparatus that is selected from the following group of apparatuses, or an apparatus operable using combined principles of several of these apparatuses:
Controllable drug dosage devices;
Controllable gas/air delivery devices;
Continuous Positive Airway Pressure (CPAP);
Bi-level positive airway pressure (BPAP);
Implantable/non-implantable Respiratory Stimulator;
Implantable/non-implantable Brain/Nerve Stimulator/Pacers;
Implantable/non-implantable cardiac defibrillators (ICD)/cardiac pacers/Cardiac Resynchronization Therapy (CRT).

* * * * *